US010545142B2

(12) United States Patent
Fahmy et al.

(10) Patent No.: US 10,545,142 B2
(45) Date of Patent: Jan. 28, 2020

(54) CALIBRATION OF NANOSTRUCTURE SENSORS

(71) Applicant: Yale University, New Haven, CT (US)

(72) Inventors: Tarek M. Fahmy, New Haven, CT (US); Aleksandar Vacic, Cambridge, MA (US); Mark A. Reed, Monroe, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 15/455,945

(22) Filed: Mar. 10, 2017

(65) Prior Publication Data

US 2017/0242000 A1 Aug. 24, 2017

Related U.S. Application Data

(63) Continuation of application No. 14/005,056, filed as application No. PCT/US2012/029080 on Mar. 14, 2012, now Pat. No. 9,599,614.

(Continued)

(51) Int. Cl.
*G01N 33/543* (2006.01)
*G01N 27/414* (2006.01)

(52) U.S. Cl.
CPC ... *G01N 33/54373* (2013.01); *G01N 27/4145* (2013.01); *G01N 27/4146* (2013.01); *G01N 33/5438* (2013.01)

(58) Field of Classification Search
CPC ......... G01N 33/54373; G01N 27/4145; G01N 27/4146; G01N 33/5438
See application file for complete search history.

(56) References Cited

U.S. PATENT DOCUMENTS 4,713,347 A * 12/1987 Mitchell ............ G01N 33/5302
204/403.06
2005/0053524 A1* 3/2005 Keersmaecker ....... B82Y 10/00
422/88

(Continued)

FOREIGN PATENT DOCUMENTS

WO 2010099318 9/2010

OTHER PUBLICATIONS

Abdolvand, et al., "An advanced reactive ion etching process for very high aspect-ratio sub-micron wide trenches in silicon", Sens and Actuators A, 144, pp. 109-116(2008).

(Continued)

*Primary Examiner* — Melanie Brown
(74) *Attorney, Agent, or Firm* — Pabst Patent Group LLP

(57) ABSTRACT

The present invention relates to uniform nanostructure biosensors and methods of calibrating the response of nanostructure biosensors. The invention overcomes device to device variability that has made quantitative detection difficult. The described biosensors have uniform characteristics that allow for more reliable comparison across devices. The methods of the invention comprise normalizing the initial current rate, as measured by the nanostructure biosensor following the addition of an analyte, to device characteristics of the biosensor. The device characteristics of the biosensor which can be used to normalize the response include baseline current and transconductance. Calibration of responses allows for the generation of calibration curves for use in all devices to quantitatively detect an analyte, without the need for individual device calibration.

23 Claims, 44 Drawing Sheets

Related U.S. Application Data

(60) Provisional application No. 61/452,212, filed on Mar. 14, 2011.

(56) References Cited

U.S. PATENT DOCUMENTS

| | | | | |
|---|---|---|---|---|
| 2007/0048181 | A1* | 3/2007 | Chang | B82Y 15/00 422/400 |
| 2007/0080060 | A1 | 4/2007 | Frey | G01R 19/252 204/403.01 |
| 2008/0185295 | A1* | 8/2008 | Briman | G01N 33/5438 205/777.5 |
| 2010/0184104 | A1 | 7/2010 | Fahmy | |
| 2010/0260745 | A1 | 10/2010 | Zhou | |
| 2010/0297608 | A1 | 11/2010 | Stern | |
| 2010/0327847 | A1* | 12/2010 | Leiber | B82Y 15/00 324/71.1 |
| 2011/0215002 | A1 | 9/2011 | Martinez | G01N 27/4146 205/777.5 |
| 2011/0237000 | A1* | 9/2011 | Tey | B82Y 15/00 436/518 |
| 2011/0237012 | A1 | 9/2011 | Jang | G01N 33/5438 438/49 |

OTHER PUBLICATIONS

Bergveld, "The operation of an isfet as an electronic device", Sens Actuators, 1: 17-29 (1981).
Bunimovitch, et al., "Quantitative real-time measurements of DNA hybridization with alkylated nonoxidized silicon nanowires in electrolyte solution", J Am Chem Soc. 128: 16323-31 (2006).
Cui, et al., Nanowire nanosensors for highly sensitive and selective detection of biological and chemical species, Science, 293: 1289-92 (2001).
Elfstrom, et al., "Silicon nanoribbons for electrical detection of biomolecules", Nano Lett. 8:945-949 (2008).
Habicht, et al., "Hole mobillties and electrical characteristic of ©-gated silicon nanowire array FETs with 110- and 100-channel orientation",Solid-State Device Research Conference (ESSDERC), Sevilla, pp. 372-375 (2010).
Henschel, et al., "Study of a high contrast process for hydrogen silsesquioxane as a negative tone electron beam resist", J Vac Sci Technol B, 21: 2018-2025 (2003).
Homola, "Present and future of surface plasmon resonance biosensors", Anal Bioanal Chem, 377: 528-39 (2003).
Ishikawa, et al., "A Calibration Method for Nanowire Biosensors to Suppress Device-to-device Variation", ACS Nano, 3(12): 3969-76 (2009).
Jamasb, et al., "A physical model for drift in pH ISFETs", Sens Actuators B: Chemical, 49: 146-55 (1998).
Patolsky, et al., "Electrical detection of single viruses", PNAS, 101(39): 14017-22 (2004).
Selo, et al., "Preferential labeling of alpha-amino N-terminal groups in peptides by biotin: application to the detection of specific anti-peptide antibodies by enzyme immunoassays", J Immunol Methods, 199: 127-38 (1995).
Stern, et al, "Label-free electronic detection of the antigen-specific T-cell immune response", Nano Lett, 8(10): 3310-14 (2008).
Stern, et al, "Label-free immunodetection with CMOS-compatible semiconducting nanowires", Nature, 445: 519-22 (2007).
Stern, et al., "Label-free biomarker detection from whole blood", Nat Nanotechnol, 5: 138-42 (2010a).
Stern, et al., "A nanoelectronic-enzyme linked immunosorbent assay (ne-ELISA) for detection of proteins in physiological solutions", Small, 6(2): 232-8 (2010).
Stern, et al., A capture-release separation approach for electronic detection of biomarkers from whole blood, Nature nanotechnology, doi: 10.1038/nnano.2009.353 pp. 1-19 (2009).
Sun, et al., "Electron Mobility in Inversion and Accumulation Layers on Thermally Oxidized Silicon Surfaces", IEEE Journal of Solid-State Currents, 15: 562-573 (1980).
Tabata, et al., "Anisotropic etching of silicon in TMAH solutions", Sens Actuators A: Physical, 34: 51-57 (1992).
Vacic, et al., "Multiplexed SOI BioFETs", Biosens Bioelectron, 28(1):239-42 (2011).
Zhang, et al., "DNA sensing by silicon nanowire: charge layer distance dependance", Nano Lett, 8(4): 1066-70 (2008).

* cited by examiner

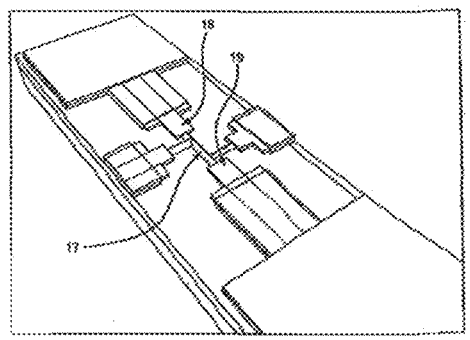
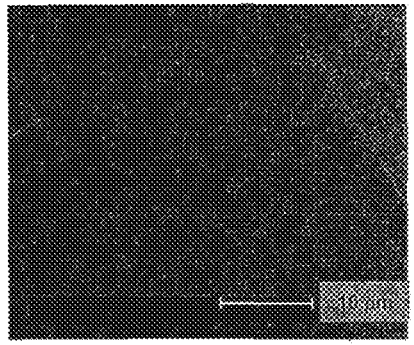
FIG. 3A　　　　　　　　　FIG. 3B
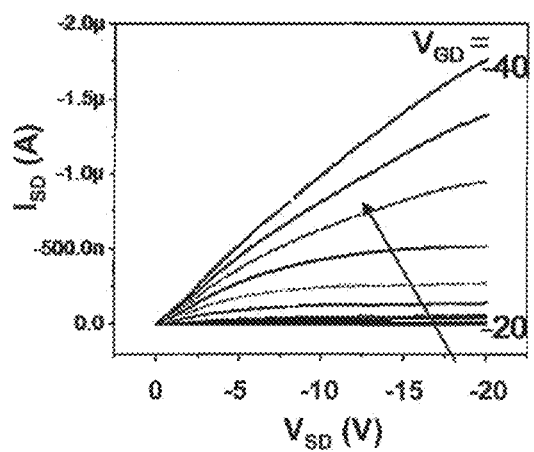
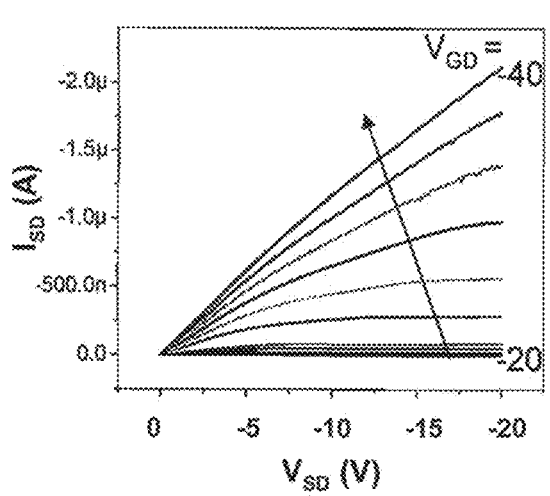
FIG. 3C　　　　　　　　　FIG. 3D

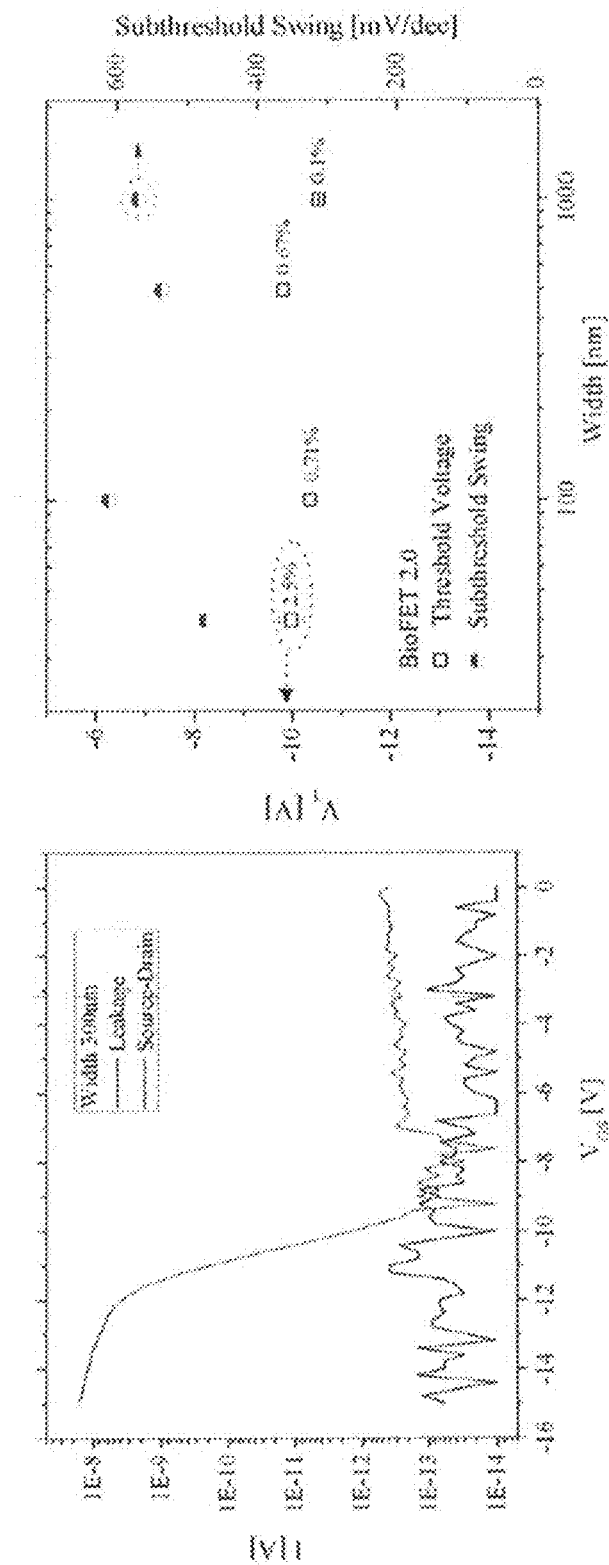

CALIBRATION OF NANOSTRUCTURE SENSORS

CROSS-REFERENCE TO RELATED APPLICATIONS

This application is a continuation of pending U.S. application Ser. No. 14/005,056, which is a § 371 application of the International Application No. PCT/US2012/029080 entitled "Calibration of Nanostructure Sensors", filed in the United States Receiving Office for the PCT on Mar. 14, 2012, which claims the benefit of and priority to U.S. Provisional Application No. 61/452,212, filed Mar. 14, 2011.

STATEMENT REGARDING FEDERALLY SPONSORED RESEARCH OR DEVELOPMENT

This invention was made with government support under R01 EB008260 awarded by National Institute of Heath. The government has certain rights in the invention.

BACKGROUND

Nanowire Field Effect Transistor (FET) sensor technology has demonstrated tremendous potential for point-of-care (POC) applications and has been successfully used for detection of proteins (Cui et al., 2001, Science, 293: 1289-1292), oligonucleotide sequences (Zhang et al., 2008, Nano Lett, 8(4): 1066-1070), cellular function (Stern et al, 2008, Nano Lett, 8(10): 3310-3314), virus detection (Patolsky et al., 2004, Proc Natl Acad Sci, 101(39): 14017-14022) and enzymatic activity (Stern et al., 2010, Small, 6(2): 232-238). Nanowire FET sensors have been used in numerous applications, and have been incorporated into label-free detection systems.

Electronic label-free detection is based on nanosensor surface modification with specific receptors capable of recognizing and binding the desired target molecules. Upon binding, the nanosensor surface potential is changed due to the electric charge present on the bound molecule, which modulates the nanosensor surface potential and thus causes an increase or decrease of carriers and device current (Bergveld, 1981, Sens Actuators, 1: 17-29).

While several qualitative studies have demonstrated the true power of this detection method, the lack of quantitative results diminishes the competitiveness of the BioFET technology with the existing state-of-the-art techniques. A number of previous experiments have been performed on "bottom-up" or chemical vapour deposition (CVD) grown nanowires, but this method suffers from large device-to-device variation in electrical parameters such as threshold voltage, mobility and transconductance (Ishikawa et al., 2009, ACS Nano, 3(12): 3969-3976). Given these fluctuations, individual device calibration is thus required for quantitative analysis, thus eliminating one of the primary advantages of a microfabrication approach, i.e. multiplexing.

Thus, there is a need in the art for biosensors with uniform characteristics and for methods of calibrating the response of biosensors to provide quantitative detection and analysis. The present invention satisfies this unmet need.

SUMMARY OF THE INVENTION

In one aspect, the present invention relates to a sensor having uniform characteristics suitable for quantitative detection of an analyte in a sample. The sensor comprises a nanostructure fabricated on a substrate and forming an electrically conducting pathway between at least a first contact and a second contact. At least one of the baseline current, transconductance, and threshold voltage, are uniform in the sensors of the invention.

In one embodiment, the substrate is either a semiconductor substrate or a semiconductor-on-insulator (SOI) substrate.

In one embodiment, the nanostructure of the sensor includes a nanowire, a nanoribbon, or a combination thereof.

In one embodiment, the first and second contacts of the sensor form a source and drain contact. In one embodiment, a gate contact is applied to the sensor. In one embodiment, the gate sensor is a solution gate.

In one embodiment, a solution chamber is coupled to the sensor for mixing a plurality of fluids and supplying the mixed fluids to the sensor for liquid-phase electrical response characterization.

In one embodiment, the uniform characteristics of the sensor can be the baseline current, transconductance, or threshold voltage.

In one embodiment, the sensor detects the presence of an analyte and the surface of the nanostructure of the sensor is functionalized with receptor molecules that specifically bind to the analyte. In one embodiment, the current conducted by the nanostructure is altered by the presence of a parameter to be sensed. In one embodiment, the Initial current rate of the current conducted by the nanostructure is indicative of the presence of a parameter to be sensed. In one embodiment, the response of the sensor is calibrated by normalizing the initial current rate by a characteristic of the sensor. In one embodiment, the characteristic of the sensor is either the baseline current or transconductance. In one embodiment, the transconductance is the solution transconductance. In one embodiment, calibration of the response allows quantification of the parameter to be sensed.

In another aspect, the present invention relates to methods of calibrating the response of a sensor from the application of a test sample. The method includes obtaining a characteristic of the sensor, applying the test sample to the sensor, measuring the initial current rate conducted by a nanostructure of the sensor in response to application of the test sample, and normalizing the measured initial current rate by the obtained characteristic.

In one embodiment, the sensor of the method detects the presence of a specific analyte and the surface of the nanostructure of the sensor is functionalized with receptor molecules that bind the specific analyte. In one embodiment, the nanostructure of the sensor includes a nanowire, nanoribbon, or combination thereof.

In one embodiment, the obtained characteristic of the sensor is either baseline current or transconductance. In one embodiment, the transconductance is solution transconductance. In one embodiment, the method of calibrating the response of the sensor allows quantification of a parameter to be sensed.

In another aspect, the present invention relates to method of generating a calibration curve for an analyte to be detected by a sensor. The method includes obtaining at least one characteristic of the sensor, applying a first sample having a first known concentration of the analyte to the sensor, measuring the initial current rate conducted by a nanostructure of the sensor in response to the application of the first sample, and normalizing the measured initial current rate by the obtained characteristic, thereby providing a first known normalized device signal. The method further includes applying a second sample having a second known concentration of the analyte to the sensor, measuring the initial current rate conducted by a nanostructure of the sensor in response to the application of the second sample, and normalizing the measured initial current rate by the obtained characteristic, thereby providing a second known normalized device signal. The method further includes plotting a first known data point, where the first known data point includes the first known concentration and the first known normalized device signal, and plotting a second known data point, where the second known data point includes the second known concentration and the second known normalized device signal on a graph. The method also includes fitting a calibration curve between the first known data point and the second known data point.

In one embodiment, the surface of the nanostructure is functionalized with receptor molecules that bind the analyte. In one embodiment, the nanostructure includes a nanowire, a nanoribbon, or combination thereof.

In one embodiment, the obtained characteristic of the sensor is either baseline current or transconductance. In one embodiment, transconductance is solution transconductance. In one embodiment, the calibration curve allows quantification of the concentration of the analyte in any test sample detected by any sensor.

In another aspect, the present invention relates to a method of quantitatively detecting the concentration of an analyte in a test sample. The method includes obtaining at least one characteristic of a sensor, applying the test sample to the sensor, measuring the initial current rate conducted by a nanostructure of the sensor in response to the application of the test sample, normalizing the measured initial current rate by the obtained characteristic, thereby providing a measured normalized device signal, and calculating the concentration of the analyte using the measured normalized device signal and a calibration curve specific for the analyte.

In one embodiment, the surface of the nanostructure is functionalized with receptor molecules that bind the analyte. In one embodiment, the nanostructure includes a nanowire, a nanoribbon, or combination thereof.

In one embodiment, the obtained characteristic of the sensor is either baseline current or transconductance. In one embodiment, transconductance is solution transconductance.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 3A shows a schematic diagram (not to scale) of an exemplary four-point NW-FET device with source S, drain D, and gate G defined for a two-point sensing configuration. The TMAH-etched active sensing region 17 is shown.

FIG. 3B shows a scanning electron micrograph of an exemplary 4-point NW-FET device having a in-line lead length of 30 μm.

FIG. 3C shows $I_{sd}$ (Vsd) dependence for Vgd varied in −2V steps for a representative device in air before APTS functionalization.

FIG. 3D shows $I_{sd}$ (Vsd) dependence for Vgd varied in −2V steps for a representative device in air after functionalization with APTS.

FIG. 22, comprising FIG. 22C illustrates the expansion of the region encompassed by the broken line box in FIG. 22B. FIG. 22D illustrates the expansion of the region encompassed by the broken line box in FIG. 22C.

FIG. 23, comprising FIG. 23A is an optical image of devices outfitted with sensing reservoirs. The inset shows an optical micrograph of a completed device. Only the central region of the device (black arrow) is exposed to the solution. Metal leads contact the device source and drain and fan out to larger contacts (not shown). The 25 nm thick silicon device appears light gray. FIG. 23B is a $I_{DS}$ ($V_{DS}$) graph for $V_G$ varied from 0 to −20V (arrow shows direction of increasing negative $V_G$) for a representative device illustrating p-type accumulation mode behavior. FIG. 23C is a $I_{DS}$ ($V_G$) plot ($V_{DS}$=1 V) for the device used in FIG. 23B. The Inset highlights $I_{DS}$ (nA) around the operating point ($V_G$=−5V). FIG. 23D is a plot demonstrating the effect of varying solution gate voltage ($V_{G,SOLN}$) on device current ($I_{DS}$, solid line) and device-to-solution leakage current ($I_{LEAK}$, broken line) for $V_{DS}$=1 V.

FIG. 24, comprising FIG. 24A illustrates response of an anti-PSA functionalized sensor to a microfluidic purification chip-purified blood sample initially containing 2.5 ng/ml PSA (and also 30 U/ml CA15.3), marked as (ii), or a control sample containing neither, marked as (i). FIG. 24B illustrates response of an anti-CA15.3 functionalized sensor to a microfluidic purification chip-purified blood sample initially containing 30 U/ml CA15.3 (and also 2.5 ng/ml PSA), marked as (ii), or a control sample containing neither, marked as (i). FIGS. 24C and 24D illustrate the normalized response of two anti-PSA (FIG. 24C) and two anti-CA15.3 (FIG. 24D) functionalized devices to microfluidic purification chip-purified blood containing both PSA and CA15.3, with concentrations labeled. A least-squares fit is represented by a solid black line over the selected region (line endpoints).

FIG. 25, comprising FIG. 25A illustrates the anti-PSA functionalized device backgating (using the handle wafer). FIG. 25B illustrates the anti-CA15.3 functionalized device backgating (using the handle wafer). FIG. 25C illustrates the solution gating.

FIG. 39, comprising FIG. 39A and FIG. 39B, are graphs that depict the characteristics of exemplary devices. FIG. 39A demonstrate the typical device I-$V_G$ characteristics, for leakage current and source drain current. FIG. 39B demonstrates the size dependence of bioFET threshold voltages and subthreshold swings.

FIG. 40, comprising FIG. 40A depicts a device schematic. FIG. 40B depicts the electrical characteristics, $I_{ds}$-$V_{gs}$, and $g_m$-$V_{gs}$, of a typical nanoribbon device, FIG. 40C depicts the threshold voltage distribution of nanoribbon devices across a 4" wafer. Each data point is a 5 mm×5 mm die containing up to 8 devices. The inset shows approximate die positions on the wafer. Notation (a) and (b) in the die label refers to the lower and the upper half of a 10 mm×5 mm die. (10,3) is a center column die.

FIG. 43, comprising FIG. 43A depicts a calibration curve for PSA. FIG. 43B depicts a calibration curve for CA15.3. Calibration curves for (a) PSA and (b) CA15.3 show linear device response in the clinically relevant range of analytes. Circular data point represents a blind measurement.

DETAILED DESCRIPTION OF THE INVENTION

Figure 1:
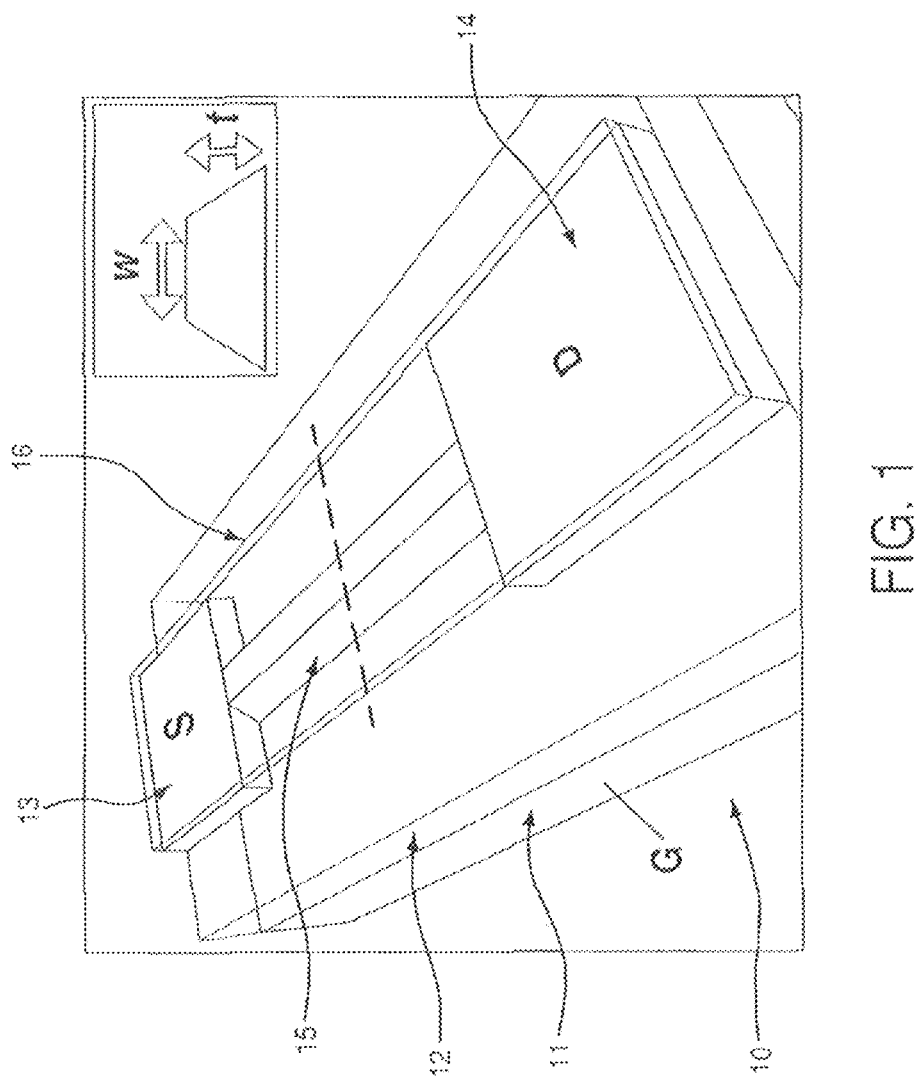
FIG. 1 shows a schematic diagram of an exemplary nanowire device, according to one embodiment of the invention, after anisotropic etching and before removal of the 600 nm wide masking oxide.

The present invention relates to nanostructure biosensors of uniform characteristics that can quantitatively detect or sense biological or chemical processes. The uniformity of the devices described herein, reduce device to device variability which has made quantitative sensing problematic for nanostructure biosensor devices. In one embodiment the uniform nanostructure biosensors of the present invention quantitatively detect the amount or concentration of a specific biomarker, for example cancer biomarkers.

The present invention also describes methods to calibrate or normalize the response of a nanostructure biosensor, such that responses can be reliably compared across devices. Fabrication of nanostructure biosensors often results in devices that vary in their electrical parameters. The present invention is based upon the finding that the initial current rate following the addition of a test sample, scales linearly with baseline current and transconductance. In one embodiment, the initial current rate is indicative of the initial kinetic reaction rates of an analyte binding to a receptor, and is an accurate determinant of analyte concentration. The methods of the invention allow for the calculation of a normalized device signal that can be used as the output of nanostructure biosensors, which can thus be compared across devices, regardless of device to device variability.

Further, the invention provides methods of using normalized device signals to generate a universal calibration curve for a given analyte. The universal calibration curve can then be used to reliably quantitatively detect a parameter in a test sample, for example, the unknown concentration of an analyte. The methods of the invention account for the device to device variability that can plague nanostructure biosensors thereby allowing comparison of responses across devices.

Definitions

As used herein, each of the following terms has the meaning associated with it in this section.

As used herein, unless defined otherwise, all technical and scientific terms generally have the same meaning as commonly understood by one of ordinary skill in the art to which this invention belongs. Generally, the nomenclature used herein and the laboratory procedures in cell culture, molecular genetics, organic chemistry, and peptide chemistry are those well known and commonly employed in the art.

As used herein, the articles "a" and "an" refer to one or to more than one (i.e. to at least one) of the grammatical object of the article. By way of example, "an element" means one element or more than one element.

As used herein, the term "about" will be understood by persons of ordinary skill in the art and will vary to some extent on the context in which it is used. As used herein, "about" when referring to a measurable value such as an amount, a temporal duration, and the like, is meant to encompass variations of ±20% or ±10%, more preferably +5%, even more preferably ±1%, and still more preferably ±0.1% from the specified value, as such variations are appropriate to perform the disclosed methods.

As used herein, the term "physiological solution" refers to any solution comprising physiological material isolated from a living organism. Non-limiting examples of physiological materials contemplated within the invention are blood, blood subfractions, serum, lymphatic fluid, saliva, urine, sweat, vaginal fluid and sperm. In one embodiment, the physiological solution comprises material selected from the group consisting of blood, blood subfractions, serum, lymphatic fluid, saliva, urine, sweat, vaginal fluid and sperm. In another embodiment, the physiological solution comprises blood.

As used herein, the term "sample" or "test sample" refers to a material to be analyzed by the sensors of the invention. For example, the sample contains some property that is to be detected by the sensor. In one embodiment, a sample comprises a physiological solution. In another embodiment, a sample can be derived from physiological material isolated from a living organism. The sample may contain any material suitable for detecting the desired analytes, and may comprise cellular and/or non-cellular material obtained from an organism.

An "analyte", as used herein refers to any substance or chemical constituent that is undergoing analysis. For example, an "analyte" can refer to any atom and/or molecule; including their complexes and fragment ions. The term may refer to a single component or a set of components. In the case of biological molecules/macromolecules, such analytes include but are not limited to: polypeptides, polynucleotides, proteins, peptides, antibodies, DNA, RNA, carbohydrates, steroids, and lipids, and any detectable moiety thereof, e.g. immunologically detectable fragments. In one embodiment, the analyte is contained within the sample applied to the sensors of the invention. In one embodiment, the sensors determine the amount, concentration, or presence of an analyte in a sample. An analyte can be a biomarker.

As used herein, "biomarker" in the context of the present invention encompasses, without limitation, proteins, nucleic acids, and metabolites, together with their polymorphisms, mutations, variants, modifications, subunits, fragments, protein-ligand complexes, and degradation products, protein-ligand complexes, elements, related metabolites, and other analytes or sample-derived measures. Biomarkers can also include mutated proteins or mutated nucleic acids. Biomarkers also encompass non-blood borne factors or non-analyte physiological markers of health status, such as clinical parameters, as well as traditional laboratory risk factors. Biomarkers also include any calculated indices created mathematically or combinations of any one or more of the foregoing measurements, including temporal so trends and differences.

As used herein, the term "polypeptide" refers to a polymer composed of amino acid residues, related naturally occurring structural variants, and synthetic non-naturally occurring analogs thereof linked via peptide bonds. Synthetic polypeptides may be synthesized, for example, using an automated polypeptide synthesizer. As used herein, the term "protein" typically refers to large polypeptides. As used herein, the term "peptide" typically refers to short polypeptides. Conventional notation is used herein to represent polypeptide sequences: the left-hand end of a polypeptide sequence is the amino-terminus, and the right-hand end of a polypeptide sequence is the carboxyl-terminus.

As used herein, the polypeptides include natural peptides, recombinant peptides, synthetic peptides or a combination thereof. A peptide that is not cyclic has an N-terminus and a C-terminus. The N-terminus has an amino group, which may be free (i.e., as a $NH_2$ group) or appropriately protected (for example, with a BOC or a Fmoc group). The C-terminus has a carboxylic group, which may be free (i.e., as a COOH group) or appropriately protected (for example, as a benzyl or a methyl ester). A cyclic peptide does not necessarily have free N- or C-termini, since they are covalently bonded through an amide bond to form the cyclic structure. The term "peptide bond" means a covalent amide linkage formed by loss of a molecule of water between the carboxyl group of one amino acid and the amino group of a second amino acid.

As used herein, amino acids are represented by the full name thereof, by the three letter code corresponding thereto, or by the one-letter code corresponding thereto, as indicated below:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |

-continued

| Full Name | Three-Letter Code | One-Letter Code |
|---|---|---|
| Phenylalanine | Phe | F |
| Tryptophan | Trp | W |

As used herein, the term "antibody" refers to an immunoglobulin, whether natural or partly or wholly synthetically produced. The term also covers any polypeptide, protein or peptide having a binding domain that is, or is homologous to, an antibody binding domain. These may be isolated from natural sources, or may be partly or wholly synthetically produced. Examples of antibodies are intact immunoglobulin molecules, as well as fragments thereof, such as Fab, F(ab')2, Fv fragments, and single chain variable fragments (scFv), which are capable of binding an epitopic determinant. Antibody fragments refer to antigen-binding immunoglobulin peptides that are at least about 5 to about 15 amino acids or more in length, and that retain some biological activity or immunological activity of an immunoglobulin. Antibody as used herein includes polyclonal and monoclonal antibodies, hybrid, single chain, and humanized antibodies, as well as Fab fragments, including the products of a Fab or other immunoglobulin expression library, and suitable derivatives.

As used herein, the "first antibody" and the "second antibody" are distinct antibodies that are raised against the antigenic target of interest (for example, a protein, peptide, carbohydrate, nucleotide, deoxynucleotide, or other small molecule). The second antibody binds to a different biomarker epitope than the first antibody conjugated to the biotinylated-photocleavable crosslinker, and therefore binding of the primary antibody to the biomarker does not prevent binding of the secondary antibody to the biomarker. Antibodies that recognize and bind with high affinity and specificity to unique epitopes across a broad spectrum of biomolecules are available as high specificity monoclonal antibodies and/or as polyclonal antibodies. These antibodies are useful not only to detect specific biomolecules but also to measure changes in their level and specificity of modification by processes such as phosphorylation, methylation, or glycosylation.

As used herein, the term "specifically binds," referring to a receptor molecule binding to an analyte of choice, means that the receptor molecule binds the analyte of choice, or portion thereof, but does not bind to a molecule that is not the analyte of choice. Receptor molecules that specifically bind to an analyte of choice, or portions thereof, do not substantially cross-react with molecules outside the analyte of choice. Receptor molecules can include antibodies, antibody fragments, proteins, nucleotide sequences, and the like.

As used herein, the term "monoclonal antibody" includes antibodies that display a single binding specificity and affinity for a particular epitope. These antibodies are mammalian-derived antibodies, including murine, human and humanized antibodies. As used herein, an "antibody heavy chain" refers to the larger of the two types of polypeptide chains present in all antibody molecules in their naturally occurring conformations. As used herein, an "antibody light chain" refers to the smaller of the two types of polypeptide chains present in all antibody molecules in their naturally occurring conformations.

As used herein, a "polynucleotide" means a single strand or parallel and anti-parallel strands of a nucleic acid. Thus, a polynucleotide may be either a single-stranded or a double-stranded nucleic acid.

As used herein, the term "nucleic acid" typically refers to large polynucleotides.

As used herein, the term "oligonucleotide" typically refers to short polynucleotides, which are generally not greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

As used herein, a "portion" of a polynucleotide means at least about twenty sequential nucleotide residues of the polynucleotide. It is understood that a portion of a polynucleotide may include every nucleotide residue of the polynucleotide.

As used herein, a "probe" refers to a polynucleotide that is capable of specifically hybridizing to a designated sequence of another polynucleotide. A probe specifically hybridizes to a target complementary polynucleotide, but need not reflect the exact complementary sequence of the template. In such a case, specific hybridization of the probe to the target depends on the stringency of the hybridization conditions. Probes can be labeled with, e.g., chromogenic, radioactive, or fluorescent moieties and used as detectable moieties.

As used herein, an "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g, as a cDNA or a genomic or cDNA fragment produced by PCR or restriction enzyme digestion) independent of other sequences. It also includes a recombinant DNA which is part of a hybrid gene encoding additional polypeptide sequence.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range and, when appropriate, partial integers of the numerical values within ranges. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Nanosensors

Certain embodiments of the present invention provide devices, methods for their production, and methods of use, especially suited to sense a variety of molecular species, biological species, or cellular responses. In this manner, the species and/or substances of-interest may be detected and/or monitored. These species or substances can be present in solid, liquid or gaseous state in the ambient or can be applied to the device. Sensors of the present invention, for example, are especially suited for detecting, measuring, or both, of proteins, DNA and intrinsic cellular changes or cellular changes due to extrinsic stimuli. Still further, sensors, as described and provided herein, may also be suitable for sensing cellular interactions due to paracrine, autocrine, or endocrine signaling, or combinations thereof. Sensors of the present invention have uniform electrical characteristics thereby reducing device to device variability. Further, sensors of the invention can be internally calibrated to produce normalized device signals that can be reliably compared across multiple sensors. Therefore, sensors of the present invention allow for quantitative detection. Sensors and methods of fabrication have been previously described in U.S. patent application Ser. Nos. 12/517,230; 12/535,396; and Ser. No. 12/680,833; and in International Patent so Application PCT/US10/25412, the entire contents of which are incorporated by reference in their entirety.

For example, the detection device is implemented as an elongated nanostructure, for example, a nanowire, and has an exposed surface that is substantially smooth and well defined. The nanostructure may be fabricated on a semiconductor substrate or on a semiconductor-on-insulator (SOI) substrate. Fabrication can comprise any techniques known in the art including but not limited to TMAH wet etching, plasma etching, sputter etching, reactive-ion etching (RIE), and the like. The exposed surface of the device used for detection may or may not be functionalized depending on the device's applications.

FIG. 1 shows a schematic diagram of an exemplary nanostructure sensor according to one embodiment of the invention. In this embodiment, the device is fabricated on a (100) silicon-on-insulator (SOI) wafer 10 which includes a silicon substrate 11, a thin $SiO_2$ layer 12 on the Si substrate 11 and a top Si layer on the $SiO_2$ layer 12, in which the source (S) contact 13, the drain (D) contact 14 and the actual nanostructure device 15, subsequently also referred to as nanowire 15, are defined. Also shown is a $SiO_2$ layer 16 overlaying the contact 13, 14 and the device 15. The $SiO_2$ layer 16 in the illustrated example has a width of about 600 nm, from which the nanowire device with a final width w (see inset) is then etched. The term "nanowire" is not meant to imply that all lateral surfaces of the nanowire are accessible from the outside. In the illustrated embodiment, the nanowire 15 is prepared from the top Si layer and the bottom surface of the nanowire 15 is therefore in direct material contact with the $SiO_2$ layer 12 and thus inaccessible.

The inset in FIG. 1 shows a cross-sectional view of the nanowire 15 with a trapezoidal shape of thickness t and width w defined by the processing steps, which will be described in detail below. The sloped surfaces of the trapezoid represent the natural Si (111) planes, or cleavage planes, and, in one embodiment, may have an angle of about 54.7° between the (100) plane and the (111) plane.

Figure 2:
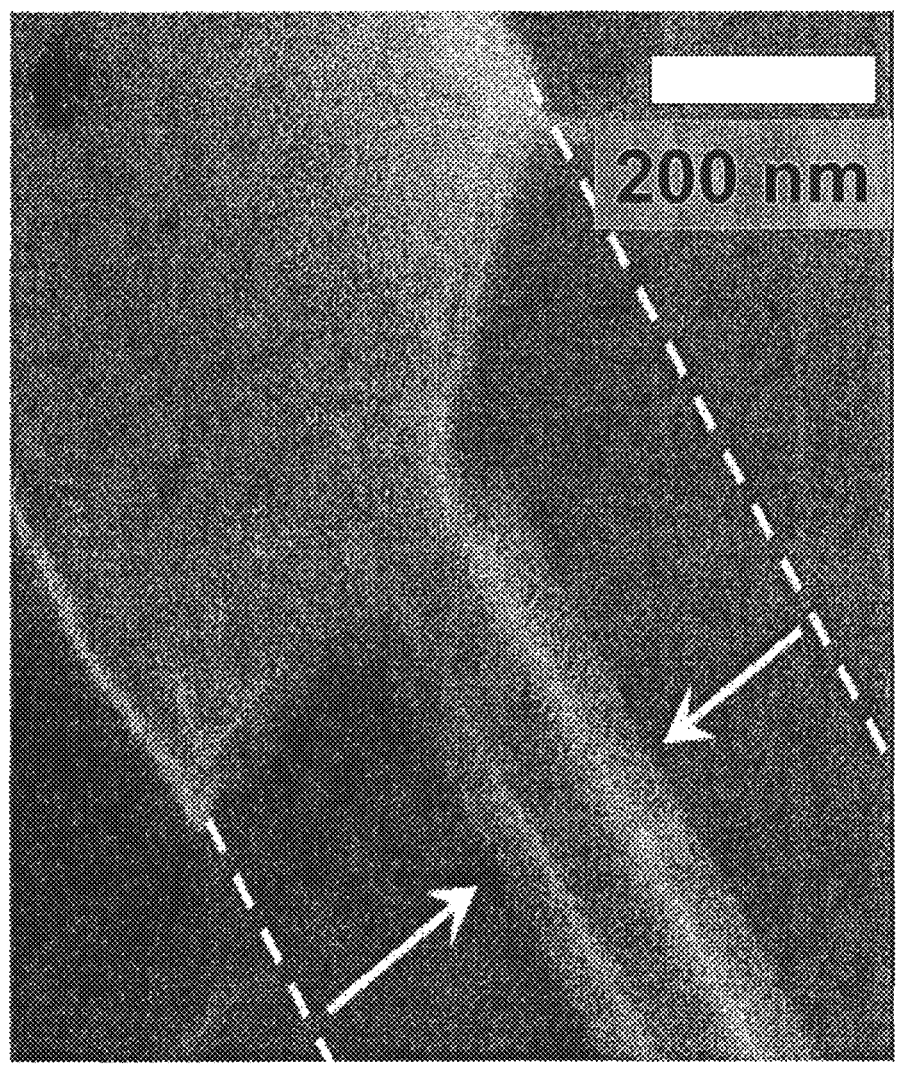
FIG. 2 shows a scanning electron micrograph (SEM) of a completed exemplary device illustrating the x≈200 nm undercut etched from the sides of the masking oxide. The final device is 80 nm wide.

FIG. 2 shows a scanning electron micrograph (SEM) of a detail near the source contact 13 of a finished device, where the top $SiO_2$ layer 16 has been removed. Although pattern-defined roughness is discernible near the contact regions, the sides of the device (i.e., the etched (111) silicon planes) appear substantially smooth without any visible surface roughness. Nanowires with a controlled width of between about 50 nm and about 200 nm have been successfully prepared.

The width of the devices may be selected to optimize device sensitivity. As those skilled in the art will appreciate, the exemplary nanowires form a conductive pathway between the contact regions 13 and 14 which, in the sensing operation, is affected by surface charges formed or deposited on or near the exposed lateral surfaces. These surface charges induce the greatest changes in the conductive pathway if they affect a substantial portion of the trapezoidal cross section of the device. The depth by which the surface charges extend from the exposed lateral surfaces inward is governed by the depletion width that in turn depends on the Debye length ($L_D$) of the semiconductor material from which the nanowire is formed. The semiconductor characteristic Debye length may be presented as:

$$L_D \equiv \sqrt{\frac{\varepsilon_s kT}{q^2 N_B}} \quad (1)$$

wherein q is the electron or hole charge, $N_B$ is the doping density, T is the absolute temperature, and $\varepsilon_s$ is the dielectric constant of the semiconductor material. Exemplary values for $L_D$ at room temperature are $L_D \approx 100$ nm for $N_B \approx 10^{15}$ cm$^{-3}$, and $L_D \approx 10$ nm for $N_B = 10^{17}$ cm$^{-3}$. The values for $L_D$ of GaAs are identical to those of Si, whereas the values for Ge are greater by a factor of 1.16 due to the larger dielectric constant. The depletion width of the conduction nanowire pathway, which depends on the Debye length ($L_D$) of the semiconductor material, can be changed by applying a gate voltage to a gate contact. The gate contact may be the silicon layer 11, operating as a back gate, or another contact layer disposed above the nanowire 15, operating as a top gate (not shown). In another embodiment, gate voltage is applied by solution gating. In this case, the electrical potential of the solution serves to modify the carrier density in the device, which gives a transconductance value of the device that can be used to accurately determine the change in surface potential due to absorbed species of interest.

In further detail, the charge of solution-based molecules and macromolecules is screened by dissolved solution counterions: a negative species such as streptavidin or DNA will be surrounded by positively charged ions due to electrostatic interactions. Accordingly, molecular charge screening by dissolved solution counterions—Debye screening—on sensor response can be evaluated. At a characteristic Debye length ($\lambda_D$), the number of not positive charges approaches the number of negative charges on the protein or DNA. The result is a screening effect such that the electrostatic potential arising from charges on the protein or DNA decays exponentially toward zero with distance. For aqueous solutions at room temperature, this Deybe length ($\lambda_D$) may be re-written from its previously described equation and now presented as:

$$\lambda_D = \frac{1}{\sqrt{4\pi l_B \sum_i \rho_i z_i^2}}, \quad (2)$$

where $l_B$ is the Bjerrum length=0.7 nm, $\Sigma_i$ is the sum over all ion species, and $\rho_i$ and $z_i$ are the density and valence, respectively, of ion species i. Thus, for optimized sensing, the Debye length must be carefully selected for NW-FET measurements since molecules binding to the devices are likely removed from the sensor surface by approximately 2-12 nm (the size of the receptor proteins or DNA linkers bound to the sensor surface). Debye length considerations, such as those now discussed, should likely be considered when designing preferred optimized protocols for label-free sensing, and such considerations may facilitate improved label-free sensing using NW-FETs. Indeed, proper consideration and optimization of Debye length selection ($\lambda_D$) may facilitate selective label-free sensing of macromolecules.

In one preferred aspect of the present invention, nanowire-FET devices may be fabricated from silicon-on-insulator (SOI) wafers. For example, in one embodiment, the NW-FET device regions may be defined with a wet chemical etch (tetramethylammonium hydroxide, TMAH), which etches Si (111) planes at approximately $\frac{1}{100}$ the rate of all other planes and thereby eliminates edge imperfections not aligned to this plane. Electron-beam lithography and subsequent reactive-ion etching may be used to define the device dimensions in a thermally grown masking oxide, and TMAH etching to subsequently transfer the pattern to the active silicon layer. It should be noted that this etch produces trapezoidal devices due to the (100) orientation of the SOI wafers. As illustrated in the schematic in FIG. 3A, the etching causes undercutting of the masking oxide into the lightly-doped region (boron, $10^{15}$ cm$^{-3}$) 17, which in turn facilitates devices with significantly smaller dimensions than originally defined. The doped source contact 18 and drain contact 19 (each doped to $>10^{20}$ cm$^{-3}$ with boron by ion implantation) extend under the metal contact pads and are not appreciably etched by the TMAH. A scanning electron micrograph of such an NW-FET device is shown in FIG. 3B. Four-point measurements showed that such devices exhibit negligible contact resistance such that sensing measurements can be made in a two-point configuration, as depicted in FIG. 3A.

The transport characteristics of such device were measured before and after surface functionalization since surface chemistry interactions have been shown to have a deleterious effect on sensing properties. The dependence of source-drain current ($I_{SD}$) on source-drain voltage ($V_{SD}$) for varying gate-drain voltage ($V_{GD}$) for a representative device is shown in FIG. 3C. In one embodiment, sensing measurements used direct current having $V_{SD}=-2V$ and $V_{GD}=-35V$. The large $V_{GD}$ required to turn on the device is consistent with SOI accumulation-mode operation. FIG. 3D shows that device functionalization with 3-aminopropyltriethoxysilane (APTS) to convert silanol (Si—OH) groups to free amines did not significantly affect the $I_{SD}$ ($V_{SD}$) of the device. The relatively minute increase in $I_{SD}$ for large $V_{GD}$ suggests the presence of a small parallel current path through the surface. However, this path was not shown to appreciably alter the electronic characteristics when the device is fully depleted ($V_{GD} \geq -20V$).

As mentioned above, the device structure, including the nanowire 15, the contact regions 13, 14 and the contact to silicon layer 11, which may operate as a back gate, are fabricated on 4" diameter SOI wafers 10. In one embodiment, the active Si layers are thinned to about 25 nm, about 40 nm, and about 80 nm by oxidation followed by wet etching.

Figure 4:
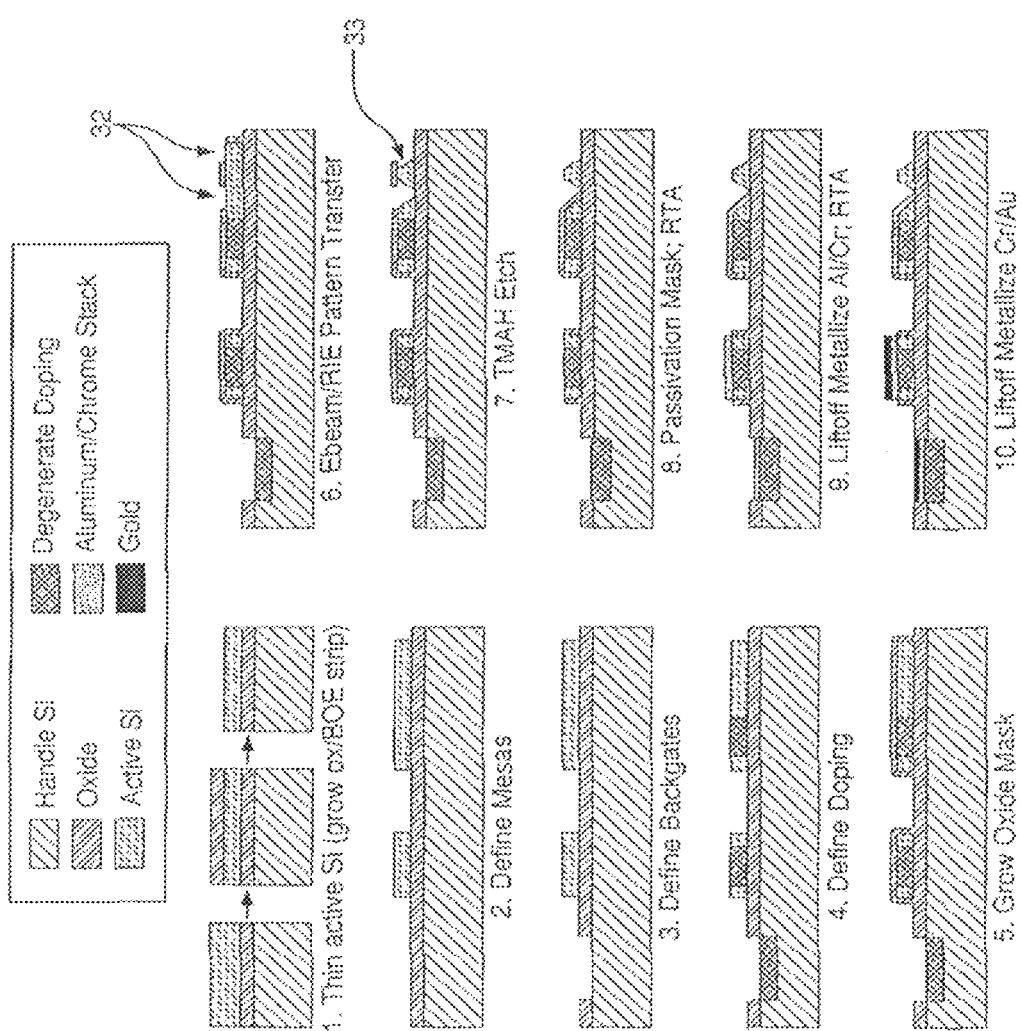
FIG. 4 shows exemplary processing steps for fabricating the nanowire sensor device according to the invention.

An exemplary process for fabrication of the nanowires according to one embodiment of the Invention is depicted in FIG. 4. Step 1 shows the formation of an oxide by thermal oxidation of the top (active) Si layer of the wafer; the thermal oxide is then removed in a buffered oxide etch (BOE), leaving an active Si layer with a reduced thickness. In Step 2, those areas on the wafer 10 which will later define the source and drain contacts 13, 14 (as referenced by FIG.

1) and the region where the actual nanowire 15 is formed, are delineated by contact lithography, and the top silicon layer outside the delineated areas is etched off by RIE to form mesas. Because the nanowire is formed in a later process step (Step 7) by exposing the Si (111) surfaces, the silicon wafer is aligned at this point with the <110> wafer flat perpendicular to the orientation of the nanowire. In Step 3, optical lithography and a two-step RIE are used to define a contact area for access to the back gate 11 (FIG. 1) and alignment marks in the handle wafer. In Step 4, the degenerate contact areas for the source contact 13 and the drain contact 14 are defined by optical lithography and formed by ion implantation. Arsenic ions are implanted for n-type conducting nanowires (inversion-mode devices), and boron ions are implanted for p-type conducting nanowires (accumulation-mode devices).

In Step 5, a thermal masking oxide (see layer 16 in FIG. 1) is grown over the implanted mesas and the gate contact area. In Step 6, the nanowire pattern is transferred to the masking oxide by e-beam lithography and the masking oxide is removed in the unexposed areas, as indicated by the arrows 32. The areas outside the pattern shown in FIG. 1 with the reference symbol 16 are then etched down to the $SiO_2$ layer 12 by RIE, leaving the mesa defined by the area under the masking oxide 16 (see FIG. 1).

In Step 7, the wafer is etched in an anisotropic wet etch, in the present embodiment tetramethyl ammonium hydroxide (TMAH), which etches the Si (111) planes about 100 times more slowly than other Si planes. Etching in TMAH retains the pattern defined by the masking oxide layer, but smooths edge imperfections not aligned with the Si (111) plane.

Figure 5:
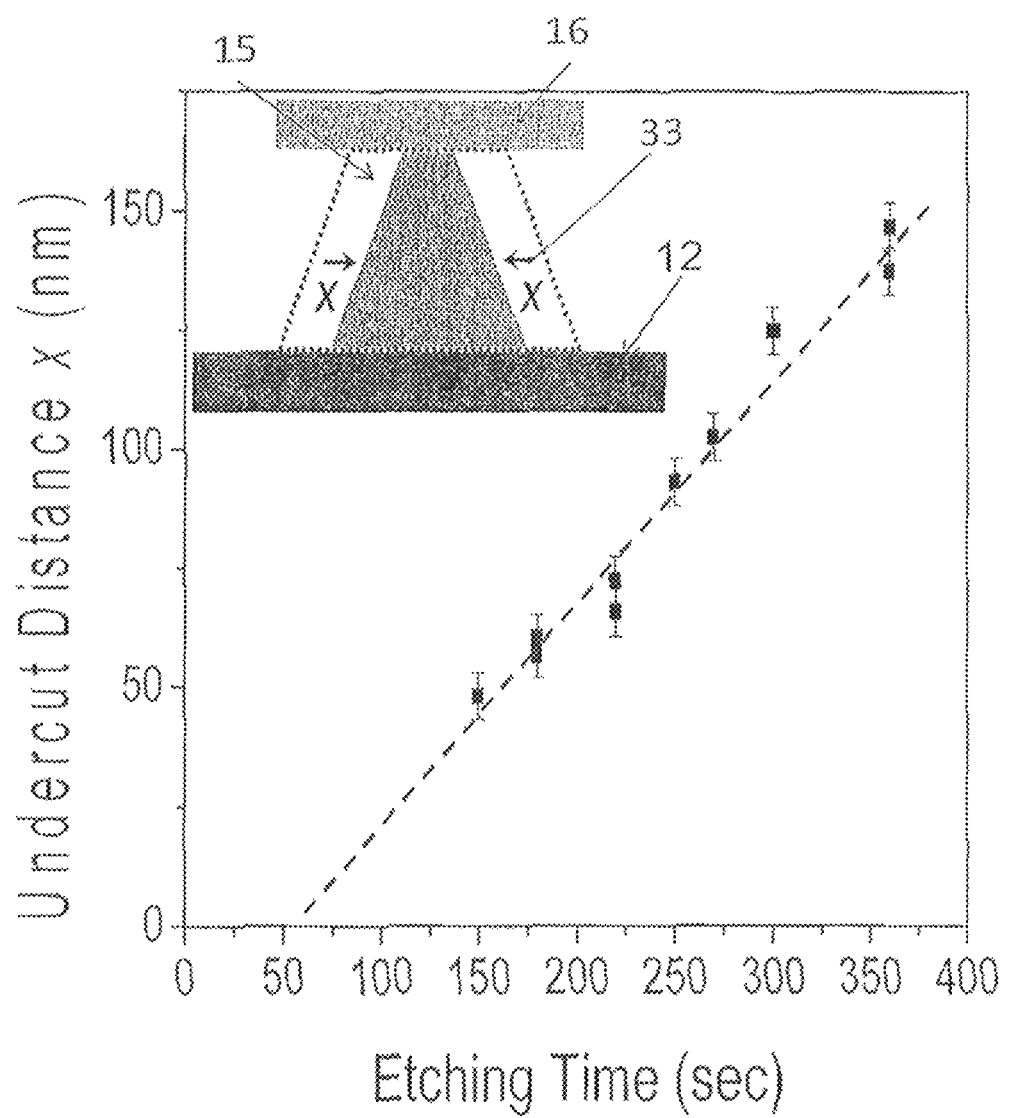
FIG. 5 demonstrates control of the lateral undercut distance as a function of the etching time for a TMAH etch.

FIG. 5 demonstrates the feature size control achieved with the TMAH etch. Plotted is the undercut distance x (in nm) as a function of the etch time (in sec). The thickness of the active Si layer was t=80 nm and four devices are investigated. At each etch time, an average laterally TMAH-etched distance x is shown for four devices, with the error bars representing one standard deviation, indicating a feature size control of better than about 10 nm.

Returning now to FIG. 4, in Step 8, optical lithography and BOE are used to remove the masking oxide from the contact pads and the active nanowire device, leaving the nanowire exposed, as shown in FIG. 2. The samples are then annealed in forming gas in a Rapid Thermal Annealing (RTA) step. In Step 9, the contact area is delineated by optical lithography and metal contact pads are deposited on the source and drain contact pads 13, 14 and the gate contact area. The metal contacts pads are fabricated by conventional lift-off Aluminum (99.999%, Kurt J. Lesker Co.)/Chromium (99.998%, Kurt J. Lesker Co.) metallization followed in Step 10 by optical lithography and a Chromium/Gold metal stack deposited by lift-off. Those skilled in the art will appreciate that other metals compatible with silicon processing technology, in particular CMOS processing, may be employed.

The afore-described fabrication process is flexible, allowing the configuration of a variety of sophisticated nanowire geometries; for example, a 6-terminal Hall sensor, a 4-terminal device for accurate resistance characterization, and the described 2-terminal sensor. Sensor arrays and integrated signal processing electronics may be readily fabricated as well.

Figure 6A:
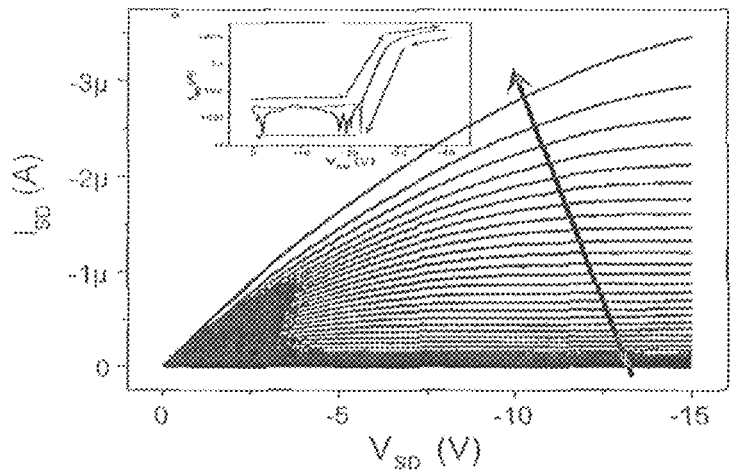
FIG. 6A shows the electrical device characteristics of an exemplary p-type sensor.

FIG. 6A shows the source-drain current ($I_{SD}$) as a function of the source-drain voltage ($V_{SD}$) of a p-type device (boron-doped silicon active layer) for various gate-drain voltages ($V_{GD}$) between 0 V to −40V in −1V steps (indicated by the bold arrow). The exemplary device has a width w≈50 nm, a thickness t≈25 nm and a length of 20 μm. The characteristics show p-type accumulation mode behavior. The inset in FIG. 6A shows for the same p-type devices the source-drain current ($I_{SD}$) as a function of the gate-drain voltage ($V_{GD}$) for constant source-drain voltage ($V_{SD}$) of =−1V for a forward and reverse sweep, indicated by the arrows. The slope of this curve is commonly referred to as transconductance ($g_m$). The device hysteresis is seen to be minimal.

Figure 6B:
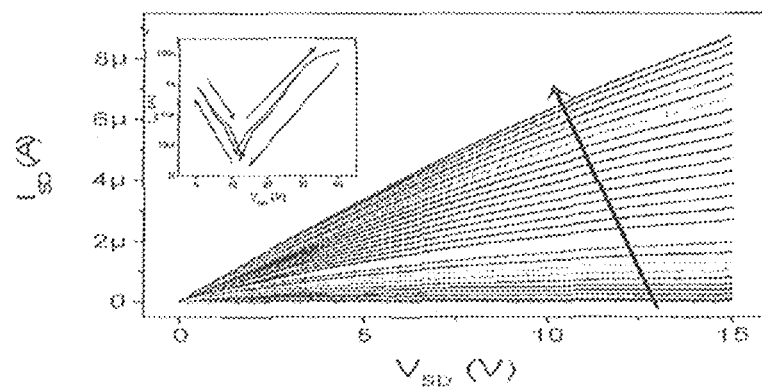
FIG. 6B shows the electrical device characteristics of an exemplary n-type sensor.

FIG. 6B shows the corresponding curves for n-type devices (arsenic-doped silicon active layer). The device has a width w≈50 nm, a thickness t≈40 nm and a length of 20 μm. The gate-drain voltage ($V_{GD}$) is varied between 0 V and +40V in steps of −+1V (indicated by the bold arrow). The characteristics show n-type inversion mode behavior. The almost imperceptible hysteresis between forward and reverse $I_{SD}$ ($V_{GD}$) in the region of maximum transconductance (steepest slope; see inset) suggest minimal defect-induced charge trapping.

Figure 6C:
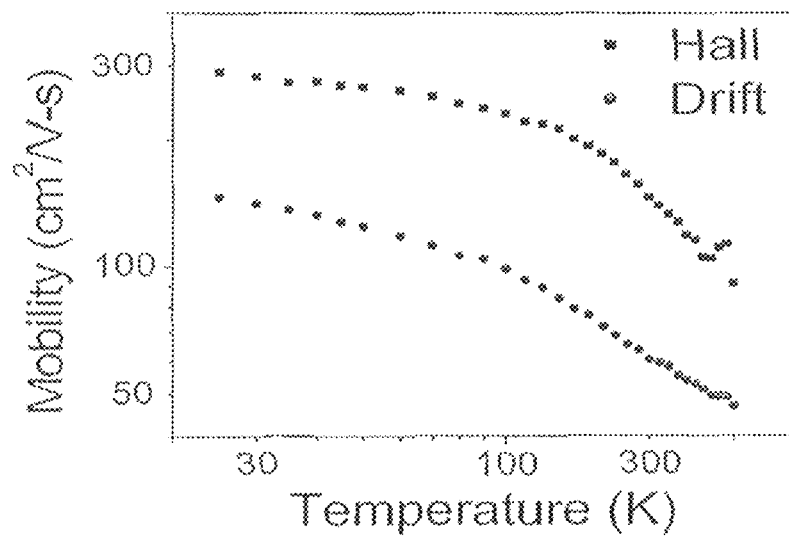
FIG. 6C shows the drift and Hall mobilities for an exemplary p-type test structure.

In one embodiment, the Hall bar configuration of a silicon nanowire makes it possible for the first time to measure the Hall mobility in the nanowire, as shown in FIG. 6C. The peak drift mobilities may be calculated from the measured $I_{SD}$ ($V_{GD}$) dependence and a self-consistent device simulation (Silvaco®). As depicted in FIG. 6C, an approximate average drift mobility of about 54 cm²/Vs is obtained, with a maximum value of 139 cm²/Vs. The device had a width w≈300 nm, and a thickness t≈25 nm. These results compare favorably with mobility data for bulk p-type silicon doped to $10^{15}$ cm$^{-3}$, which has a bulk mobility of 450 cm²/Vs. Hole mobilities are typically smaller than electron mobilities by about a factor of 2. The bulk mobility is known to decrease for anisotropically defined Si (111) planes.

This described device fabrication process provides inherent backgating capability of the nanowire channel, which permits the sensitivity of a device to be tuned through operation in different transconductance ($g_m$) regions, which is important for applications requiring a high dynamic range. Transconductance is a measure of the dependence of the source-drain current $I_{SD}$ on the gate voltage $V_{GD}$ and may be presented as:

$$g_m = \left(\frac{\partial I_{SD}}{\partial V_{GD}}\right)_{V_{SD}=const} \quad (3)$$

The sensor response to changes in the surface charge will occur at the maximum transconductance value ($g_{m,max}$). This maximum value is reached between the linear region and the saturation region of an FET transfer characteristic.

The useful gate voltage $V_{GD}$ for optimized device performance depends on the actual device parameters, for example, the electric field induced by the gate in the conductive channel of the nanowire, i.e., the thickness of the $SiO_2$ layer 12 (FIG. 1). In the described exemplary embodiments, this $SiO_2$ layer 12 is quite thick, typically about 100 nm, so that large gate voltages $V_{GD}$ are required. A decrease of the gate voltage can be expected with a thinner $SiO_2$ layer 12.

As mentioned above, both boron-doped p-type devices and arsenic-doped n-type devices can be prepared. Fabrication of these complementary devices is compatible with conventional silicon CMOS processing. The nanowire sensor devices can therefore become part of an integrated system with on-chip signal processing, error detection, and complementary detection to avoid false positives. Complementary devices are useful for detecting, for example, small concentrations of antibodies, which will be described in detail below.

The active region of the nanowire devices may be between about 1 µm to about 100 µm long, with a thickness between about 25 nm to about 100 nm. A width at the top of the trapezoidal cross-section may be etched down to about 10 nm. In general, the thinner the active region of the nanowire, the larger its surface area-to-volume ratio.

Although the illustrated nanowire devices in the exemplary embodiments are fabricated on an SOI wafer with the underlying silicon substrate operating as a back gate, a gate electrode can also be applied on top of the nanowire. In another embodiment, the gate electrode can also be inserted into a solution surrounding the device, thereby serving as a solution gate. Alternatively, the top silicon active layer can be insulated from the substrate by a reverse biased p-n junction. In an alternative embodiment, the nanowires may be formed in compound semiconductors, such as GaAs, GaAlAs, GaAlInAsP and other III-V compound semiconductors, or in any other materials that exhibit a low intrinsic surface state density that can be altered by an externally applied surface charge. As compound semiconductor layers with different composition respond differently to chemical etchants, the fabrication of devices in compound semiconductor materials may include the formation of etch stop layers which may be used to define the narrow dimensions of nanowires.

Figure 7:
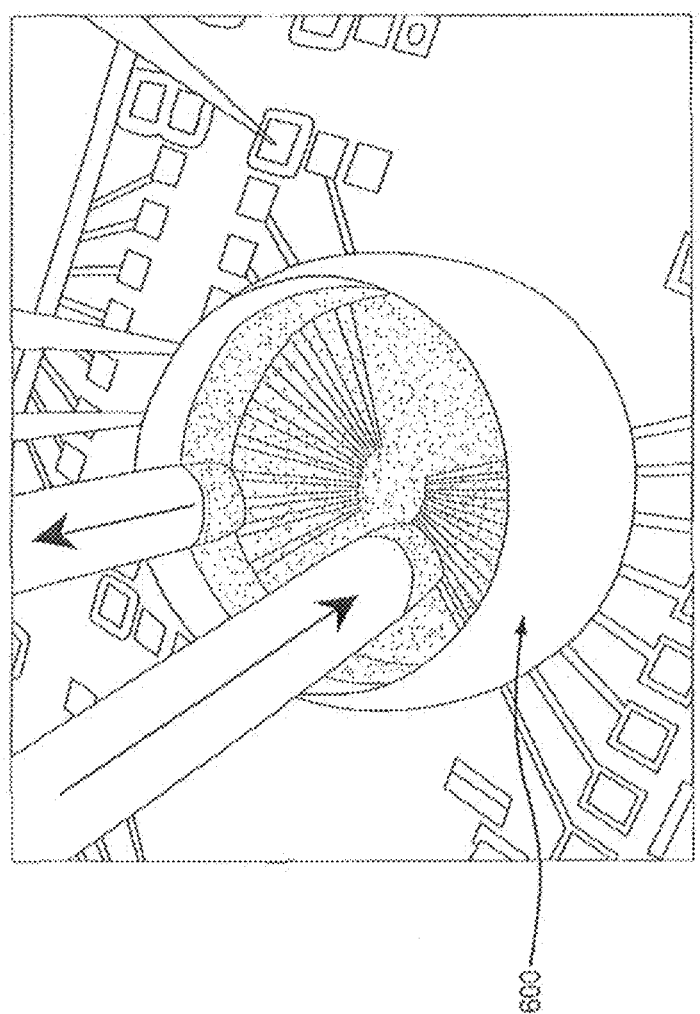
FIG. 7 illustrates a solution chamber according to one embodiment of the invention.

In certain embodiments, a macro-scale solution chamber 600 is provided to facilitate the characterization of liquid-phase sensor response by the nanowire device. FIG. 7 illustrates an exemplary solution chamber 600 configured to induce mixing of fluids that are continuously supplied to the nanowire structure for solution-based electrical response measurement. These fluids may be specific media that are conducive to cellular growth or homeostasis. In a preferred configuration, this solution chamber 600 is designed to avoid the well-characterized limits on sensitivity and response time inherent in diffusion-limited systems, such as in microchannels.

According to one aspect of the invention, the nanowire structure of FIG. 1 acts as a sensor for monitoring ionic changes of various substances. More specifically, substances of varying ion compositions, when introduced onto the native oxide surface of the nanowire device, are adapted to alter the nanowire's surface potential and effectively gating the underlying device. Hence, the nanowire structure provides a sensitive and measurable means by which ionic changes of various substances may be accurately monitored in real-time. For example, given a p-type nanowire device, if the pH of a solution introduced to the surface of the nanosensor is lower than pH of the device's native oxide coating, then the absorption of the solution onto the oxide coating results in the protonation of the oxide surface, thus depleting the hole-carriers in the device, resulting in an increase in its surface charge density, and causing a decrease in its source-drain conductivity. Conversely, when a solution having a higher pH level is introduced to the p-type nanosensor, the sensor's oxide surface is adapted to deprotonate, causing a subsequent decrease in its surface charge density and an increase in its conductivity. In addition, n-type nanowires are equally operable as miniaturized sensors for the screening of real-time molecular responses. N-type nanowire structures will be described below in greater detail. In certain implementations, the unfunctionalized nanosensors show enhanced device sensitivity towards interaction-dependent conductivity responses when the device surface area is reduced. In certain implementations, the nanosensors display favorable characteristics such as small hystereses and high reproducibility, where the average detected current levels are repeatable to less than about 15% error.

Figure 8:
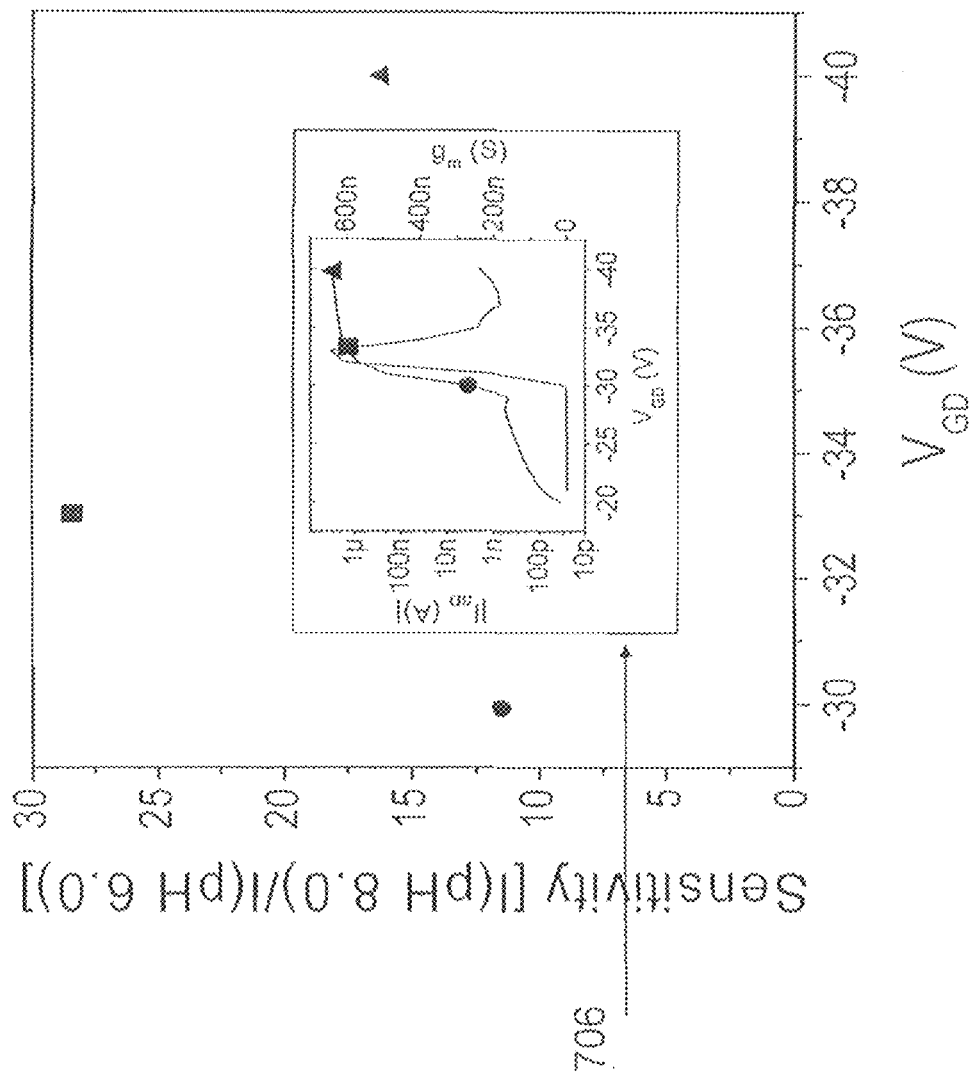
FIG. 8 illustrates sensitivity and transconductance responses, both as functions of gate-drain voltage, in an unfunctionalized p-type nanowire sensor.

In one embodiment, the unfunctionalized nanosensors of the present invention is implemented into an architecture containing a back-gate for tuning the sensitivity of the device to operate within a specific transconductance ($g_m$) region. In general, transconductance is a measure of current response with respect to gate voltage. Thus, transconductance measurements provide a quantifiable approach for a user to tune the sensitivity of the nanosensor to sense specific substances whose detection is desirable to the user. Inset 706 of FIG. 8 provides an exemplary plot of a sensor's source-drain current $I_{SD}$ and transconductance $g_m$ dependencies on gate-drain voltage $V_{GD}$ at a constant source-drain voltage $V_{SD}$ of −1V. With reference to FIG. 1, in one embodiment, the sensor has a cross-sectional thickness of about 40 nm and a cross-sectional width of about 150 nm, where this cross-sectional width refers to the smaller of the trapezoidal widths characterizing the device's cross section. FIG. 8 also illustrates a plot of the sensor's sensitivity ratio as a function of $V_{GD}$. As depicted, the sensor's measured sensitivity tracks with its measured transconductance over the range of $V_{GD}$ values. In particular, FIG. 8 shows that the most sensitive sensor response to additional surface charge occurs at the maximum transconductance state $g_{m,max}$, which is between the linear and saturation regions of the device's transfer characteristic. Hence, the sensitivity of a nanosensor may be optimized by applying appropriate voltages to the back-gate such that the sensor device is operating at $g_{m,max}$. Due to the dynamic range of sensitivities provided by gating, a nanosensor may also be tuned to a sensitivity level as specified by a user. For example, the back-gate is used to tune chemical potential of the nanosensor to a particular reaction such that only the signal from that reaction is electronically recognized by the sensor. Furthermore, a dynamic feedback loop may be coupled to the tunable nanosensor device to perform automatic and optimized sensitivity correction. In addition, one or more top-gates, lateral-gates, side-gates or any combination thereof are used to tune the nanosensor to operate within a specific transconductance, and hence sensitivity, state.

In one embodiment of the present invention, the nanostructure of the sensors is a nanoribbon. Nanoribbons are devices with nanoscale thicknesses and microscale lateral dimensions (Elfstrom et al., Nano Lett. 8:945-949). In one embodiment, nanoribbons are less sensitive than nanowire sensors. However, in one embodiment, nanoribbons have significant fabrication and cost advantages. Fabricated from ultra-thin silicon-on-insulator (UT-SOI) wafers using conventional lithographic techniques, these devices have been demonstrated to detect streptavidin in the 0.0318-53 ng/ml, range (Elfstrom et al., 2008, Nano Lett. 8:945-949), a sensitivity range ideally suited for cancer antigen detection. Nanoribbon fabrication has been described in International Patent Application PCT/US10/25412, the entire contents of which are incorporated by reference in their entirety.

Figure 21:
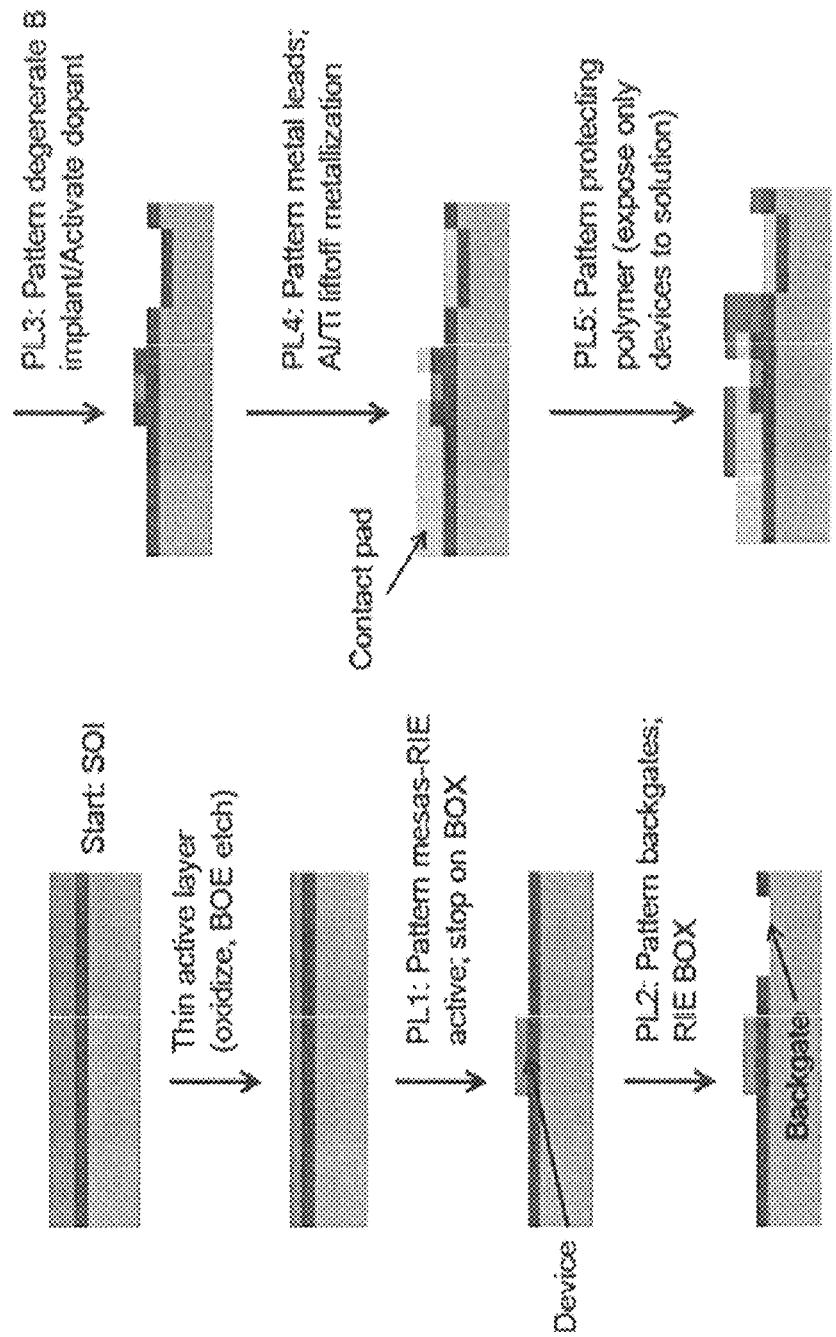
FIG. 21 is a schematic representation of an exemplary fabrication method of a nanoribbon sensor.

An exemplary method of nanoribbon fabrication is provided and illustrated in FIG. 21. Eight inch silicon-on-insulator wafers with a 70 nm active and 145 nm buried oxide (BOX) layer were purchased from SOITEC (Bernin, France) and are illustrated in FIG. 21. The doping in the active and handle wafers was boron (p-type) at $10^{15}$ cm$^{-3}$. The wafers were laser-cut to 4-inch diameters by Silicon Quest International (Santa Clara, Calif.). All photolithography steps were performed using Shipley S1808, S1813, or S1827 photoresist (Rohm & Haas, Philadelphia, Pa.) and an EV Group 620 maskaligner. All masks were 5" and were purchased from PhotoSciences, Inc. (Torrance, Calif.). The active layer was thinned to 25 nm by thermal growth of a ~98 nm oxide at 1000° C. using a MRL Industries furnace after MOS cleaning (Muller and Kamins, In "Device Electronics for integrated circuits", 2nd Ed., John Wiley & Sons, NY, N.Y., 1986). Oxide thickness was determined using a Woollam Variable Angle Spectroscopic Ellipsometer (Lincoln, Nebr.).

The silicon mesas were patterned in the first photolithographic (PL) step and chlorine reactive-ion etching (RIE) was performed using an Oxford PlasmaLab 100 RIE. This chemistry did not etch oxide, thus the BOX served as an etch-stop. Photoresist was stripped by ashing using a Mercator Control System Inc. HF-6 barrel asher.

The second PL step patterned contacted to the silicon handle wafer to serve as electronic backgates for device characterization. Vias through the BOX to the backgate were etched using 10:1 buffered oxide etch (BrandNu Labs, Meriden, Conn.) and photoresist was stripped using acetone and isopropanol (BrandNu Labs, Meriden, Conn.).

The third PL step patterned degenerate doping regions for contacts to device and backgate contacts. A boron implant dose of $5 \times 10^{15}$ cm$^{-2}$ at 8 KeV was performed at a 7° tilt by Core Systems. Photoresist was stripped by ashing, followed by wafer exposure to piranha solution. The dopant was activated by annealing the wafers at 900° C. in nitrogen in a MRL Industries furnace after MOS cleaning.

The fourth PL step patterned metal leads, pads, and contacts. A 75 nm Al (99.99%, Kurt J. Lesker Co.)/75 nm Ti (99.9%, Kurt J. Lesker Co.) liftoff evaporation was performed by electron-beam deposition in a Kurt J. Lesker EJ1800 Thin Film Deposition System. After liftoff, achieved by wafer sonication in acetone, the wafers were rapid-thermal annealed (RTA) for 1 min at 650° C. in a Surface Sciences Integration Solaris 150 RTA. Sequential RTA/electrical characterization steps (see below) dictated that these conditions were required in order to form Ohmic contacts to devices (Muller and Kamins, In "Device Electronics for integrated circuits", 2nd Ed., John Wiley & Sons, NY, N.Y., 1986).

The fifth PL step patterned S1808 photoresist as a passivating layer across the chip to prevent leakage. Exposed surfaces included contacts and active device regions (black arrow, FIG. 22D). The photoresist was hardbaked for 1 hour at 140° C. This step was performed after APTS functionalization as resist was dissolved by the organic solvents required for that process. Optical micrographs of completed devices are shown in FIG. 22. In FIG. 22, consecutive zooms are shown corresponding to dashed boxes.

Figure 9:
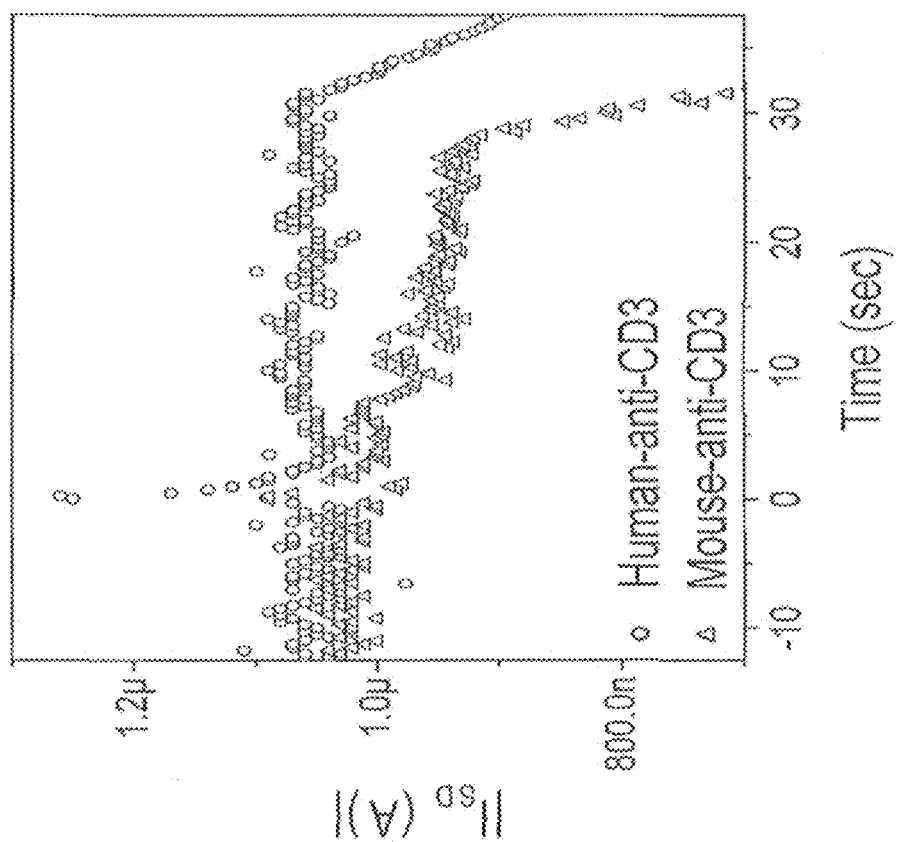
FIG. 9 illustrates conduction current responses in biotin-functionalized p-type nanowire sensors to the addition of human-α-3 and mouse-α-3 stimulants.

As described above, unfunctionalized nanostructure devices may act as ion sensors for sensing pH and other ionic changes of substances disposed on its native oxide surface. In one embodiment, such unfunctionalized nanostructure devices are used to monitor real-time cellular responses of activation-induced changes in extracellular pH. For example, real-time T-lymphocyte activation may be monitored using a nanostructure sensor, where the T-cell activation may be triggered by antibody-mediated crosslinking of cell-surface CD3, which induces intracellular signaling and, subsequently, engages effector mechanisms. One consequence of such so activation includes the release of acid that alters the surface charge density of the sensor. In one illustrative implementation, a species-specific antibody directed against mouse CD3 complex (mouse-α-3) is added to a suspension of mouse splenocytes containing about 6000 mouse-derived T-cells. This solution is then introduced to a nanosensor, having a cross-sectional width of about 100 nm and a cross-sectional thickness of about 40 nm, to detect T-cell activation by the mouse-α-3 stimulant. As illustrated in FIG. 9, the subsequent decrease in extracellular pH caused by the T-cell activation corresponds to an approximate 7.3% decrease in average current measured by the nanosensor after a current baseline is established for about 10 seconds. This current continues to decrease until current instability occurs after about 30 seconds of sensing.

In another illustrative implementation, an antibody specific to human CD3 (human-α-3-CD3) complex, which does not bind to mouse CD3, is added to the same suspension of mouse splenocytes as described above. Hence no mouse-derived T-cell activation is expected to take place. This is confirmed by electrical current measurements taken from the sensor device, as shown in FIG. 9, which indicates that minimal change in current has resulted from the addition of the human-α-3-CD3 stimulant.

Figure 10A:
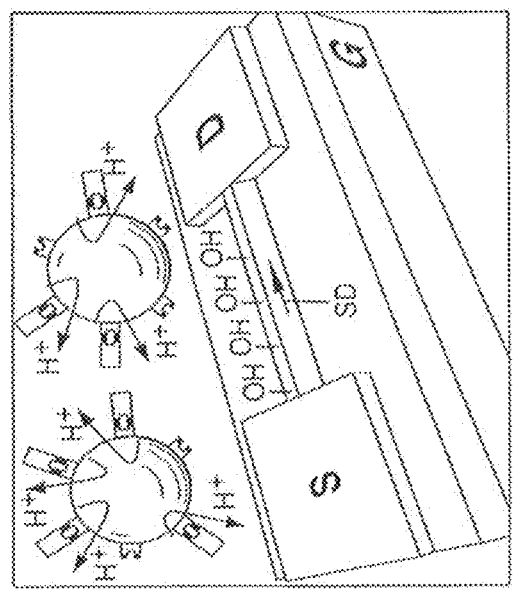
FIG. 10A depicts a sensing schematic prior to T cell stimulation. Prior to T cell activation, a majority of the nanowire's silanol groups (active region colored black) are deprotonated.
Figure 10B:
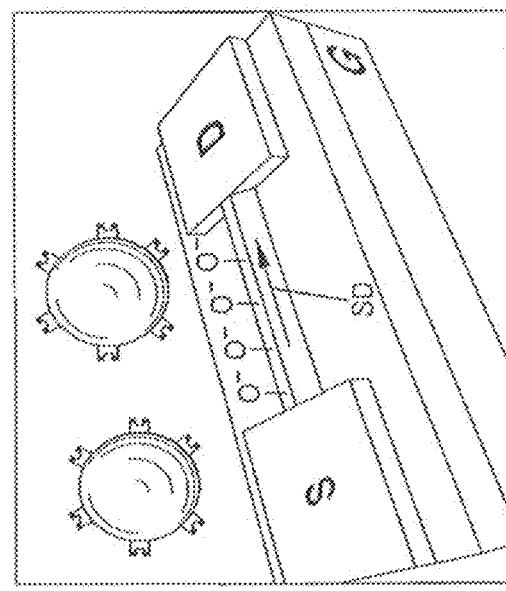
FIG. 10B depicts a sensing schematic post T-cell stimulation. After stimulation+activation, extracellular acidification results in increased protonation of the surface silanol groups, which decreases $I_{SD}$.

Yet other illustrative embodiments may be useful for sensing certain aspects of proton secretion due to activation-induced polyclonal T-cell signaling. FIGS. 10A and 10B show a sensing schematic: pre-T cell stimulation and post-stimulation+activation, respectively. Prior to T cell activation, a majority of the nanowire 20 silanol groups are deprotonated. After activation, extracellular acidification results in increased protonation of the surface silanol groups, which would decrease $I_{SD}$. The time required for T cell activation after stimulant addition can be quantified.

Figure 11A:
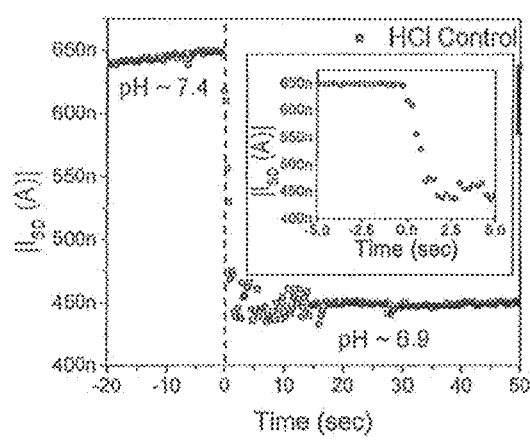
FIG. 11A shows device response to the addition of 1 mL of dilute hydrochloric acid to a cell-free buffer, demonstrating system response of approximately 1.5 sec.; Solution pH values are also provided.
Figure 11B:
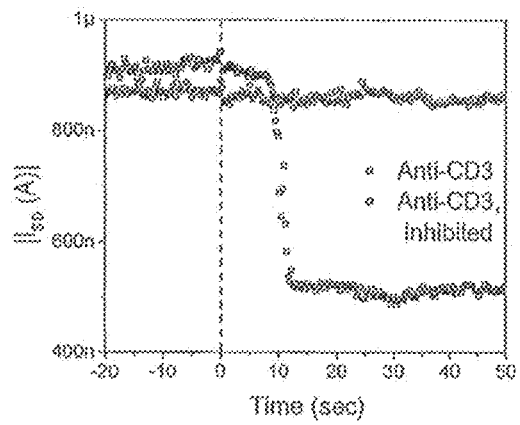
FIG. 11B shows measurement of extracellular acidification upon stimulation of B6 splenocytes with anti-CD3. The T cell response time is approximately 8 sec. Pre-treatment of splenocytes with genistein (50 mg/mL), which inhibits cell signaling, eliminates anti-CD3 induced cellular metabolic activity.

For example, splenocytes isolated from a C57BL/6 (B6) mouse were suspended in a low-buffered solution and stimulated with anti-CD3 antibody. FIG. 11B shows that extracellular acidification was observed to begin approximately 8 sec alter injection. Without being limited by theory, approximately 8 sec delay observed in FIG. 11B was believed to be primarily due to intrinsic cellular processes. To ensure that extracellular pH changes were due to stimulation-induced cellular metabolic activity, splenocytes derived from the same mouse were treated with genistein, an antibiotic that inhibits the induced intracellular signaling cascade, without affecting cellular viability. FIG. 11A shows that the presence of genistein, addition of anti-CD3 antibody resulted in no change in solution pH. This confirmed that the positive response observed in untreated cells was due to anti-CD3 antibody-Initiated proton secretion from splenocytes.

Figure 12A:
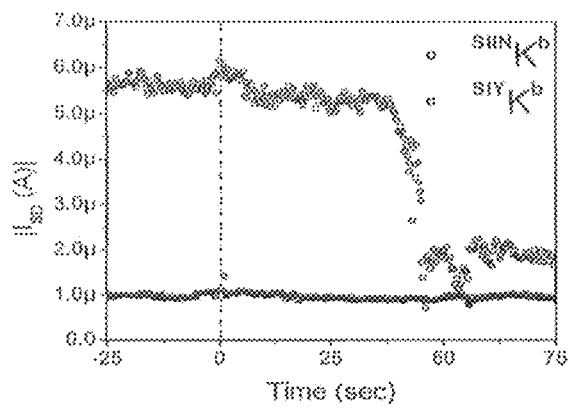
FIG. 12A shows OT-1 stimulated with $^{SIIN}K^b$ and $^{SIY}K^b$ dimeric constructs. Extracellular acidification began at approximately 40 sec for the positively-stimulated splenocyte population.

Still other embodiments are suitable for discriminating between well-established peptide-specific MHC restricted responses of T-cell clones. For example, murine splenocytes isolated from 2C and OT-1 transgenic mice were stimulated with dimeric MHC ligands presenting their cognate and non-cognate peptides. 2C and OT-1 CD8$^+$ T-cells (cytotoxic T-lymphocytes, CTLs) react against a broad range of defined peptides presented by syngeneic MHC Class 1, H-2K$^b$. OT-1 mice, expressing a transgene for the T-cell antigen receptor, are reactive with the complex of H-2K$^b$ and the ovalbumin octapeptide SIINFEKL ($^{SIIN}K^b$). As a negative control for this system, the inventors used a non-cognate peptide derived from a peptide library, SIYRYYGL ($^{SIY}K^b$). Cytotoxic T-lymphocytes from 2C transgenic mice should be reactive to $^{SIY}K^b$ but exhibit a null response to $^{SIIN}K^b$). Using a NW-FET sensor of the present invention, a drop in solution pH beginning approximately 40 sec after addition of $^{SIIN}K^b$ dimer to OT-1 splenocytes was observed; no response was observed after addition of $^{SIY}K^b$ (FIG. 12A). Conversely, 2C CTLs reacted to the presence of the $^{SIY}K^b$, with proton secretion beginning approximately 40 sec after peptide/

Figure 12B:
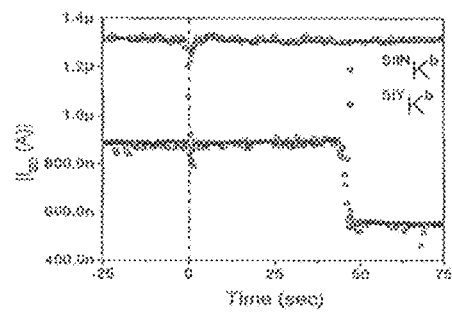
FIG. 12B shows 2C splenocytes stimulated with $^{SIIN}K^b$ and $^{SIY}K^b$ dimeric constructs. Extracellular acidification began at approximately 40 sec. for positively-stimulated splenocyte population.

MHC addition. The device showed no discernable changes in conductance when $^{SIIN}K^b$ was added to 2C splenocytes (FIG. 12B).

The observed onset of extracellular acidification of T-cells upon stimulation with peptide/MHC, after a lag of approximately 40 sec, was longer than that measured for anti-CD3 antibody stimulation, the approximately 8 sec. There were believed two candidate mechanisms potentially responsible for the observed delay: 1) the kinetics of T-cell activation are strongly affected by the dwell time of the T-cell receptor-activating stimulus. Antibodies that trigger the CD3 complex bind with higher affinities ($K_d$ approximately 1-10 nM) than peptide/MHC complexes ($K_d$ approximately 1-100 μM), which may lead to faster intracellular signaling, resulting in earlier acid release. 2) A smaller population of responsive cells (typically approximately 20-30% of all transgenic splenocytes are reactive to the specific antigen) may require a longer time for accumulation of the signaling molecules needed to achieve sufficient extracellular acidification.

Figure 12C:
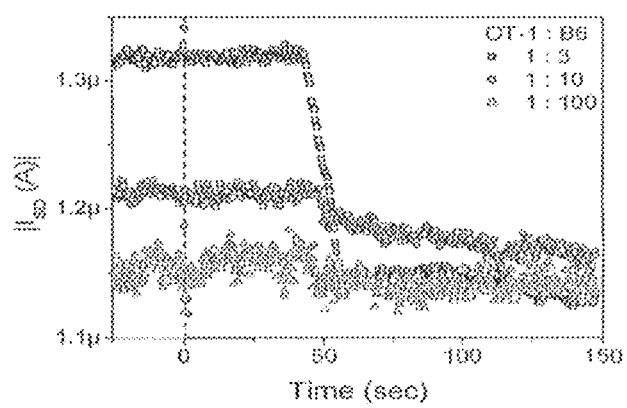
FIG. 12C shows OT-1 splenocytes diluted to various ratios with wild-type B6 splenocytes; CTL. The response to stimulation with $^{SIIN}K^b$ was measured.

Stimulating dilutions of OT-1 cells mixed with background splenocytes derived from B6 mice was used to distinguished between these possible mechanisms. Upon stimulation with cognate antigen ($^{SIIN}K^b$), FIG. 12C shows a decrease in device signal intensity with decreasing numbers of OT-1 cells. The observed responses were produced by OT-1 splenocyte populations of approximately 28000, 7000, and 700 cells for the 1:3, 1:10, and 1:100 dilutions, respectively. The onset of stimulus-induced extracellular acidification began approximately 45-49 sec for all dilutions, indicating that the strength of the stimulus, rather than changes in the cell density, was responsible for the delay. These data are consistent with previous studies that monitored the dynamics of intracellular calcium flux (which had similar response times) after stimulation with different agonists and showed that the apparent lag time after antigen-specific T-cell triggering correlated with signal strength.

These, and still other, exemplary embodiments illustrate that the nanosensors of the present invention are suitable for the accurate and efficient monitoring of real-time cellular responses based on sensing activation-induced changes without tagging or labeling the pertinent reagents involved in the reactions. The enhanced device sensitivity also contributes to the efficiency with which detections are enabled. Indeed, such illustrative nanosensor are suitable for label-free detection of stimulus-induced extracellular acidification within seconds after stimulation of a small number of cells, <210 (30% of 700). Illustrative NW-FET sensor sensitivity, rapid response time, low required sample volume, and suitability for high-throughput analysis show great applicability towards a variety of clinical and diagnostic applications.

Nanosensors of the present invention, and their associated methods of use, may be used in diagnostic applications that require the accurate discrimination among cells primed against different pathogens. For example, HIV infected cells (lymphocytes) respond to HIV antigens via activation-induced changes in T-cell functions. Thus, lymphocytes isolated from healthy and diseased donors who are non-responsive and responsive, respectively, to HIV antigens can be easily and quickly screened in a label-free manner using the sensor device of the present invention.

Unfunctionalized nanosensors may also be used to monitor other real-time cellular responses based on the sensing of activation-induced extracellular ionic changes. For example, the nanosensor devices may be used to detect the stimulation of T-cells, neutorphi, basophil, dendritic, macrophage, regulatory and natural killers, and other cells of the immune system. In these applications, stimuli of the respective cells are used to discriminate among the cells primed against specific antigens. Each interaction is likely to trigger extracellular changes in ions that are detectable by the sensor device due to a correlated change of the device conduction current. Exemplary ionic changes include changes related to hydrogen ions, calcium ions, ATP ions, and other ions that tend to propagate during cellular responses. Exemplary stimuli include antibodies, peptide or major histocompatibility complexes, carbohydrates, nucleotides, synthetic polymers and monomers, and other ligands that tend to trigger cellular functions.

In yet another application, unfunctionalized nanosensor devices may be used to ascertain protein and macromolecule stability and aggregation potential because as these molecules unfold, for example, upon exposure to a denaturant, the molecules tend to change the electrical properties of the nanosensor whereon the molecules are applied. The resulting change in device conduction current can be used to deduce a stability measurement for each molecule, hence providing a facilitated approach to assess the propensity of the molecule towards aggregation which potentially leads to one or more diseased states. For example, detection of unfolding and aggregation of amyloid peptides may be a warning sign for Alzheimer's. Detection of crytallin peptide aggregation may be a warning sign for cataracts.

In another application, the nanostructure sensors may be used to detect exocytosis, which is essential to normal cell functions and forms the basis of intercellular communication in multi-cellular organisms. Exocytosis involves the intracellular and intercellular transport of membrane-bound vesicles that tend to release their content upon fusion with other cells. Hence, the sensor device of the present invention may be used to detect exocytosis by sensing changes in the device's electrical properties in correlation to degranulation, or the release of substances, from the vesicles. Secreted substances include proteins, carbohydrates, ions, nucleotides or other macromolecules with a net surface charge that impacts the charge of the sensor. More specifically, the sensor device is able to detect pathological cells in connection to two known types of exocytosis. Constitutive exocytosis occurs independent of extracellular stimuli. Often, this type of exocytosis is dysfunctional in diseased or infected cells. Therefore, the ability to monitor constitutive exocytosis is important to differentiating between normal and pathological cells without the presence of a stimulus. Regulated exocytosis occurs when cells are triggered by a stimulus which may lead to secretion of hormones, acidic granules, second messengers, digestive enzymes and other molecules. Again, dysfunction in regulated exocytosis may be indicative of pathology. Often, pathological cells secrete granules in response to external stimuli such as the way HIV-infected cells respond to HIV antigens or autoimmune cells respond to autoimmune antigens. The sensor device is able to measure exocytic secretion of granules resulted from both constitutive and regulated exocytosis. In addition, the sensor device is able to distinguish between cells capable and incapable of secreting granules. In certain exemplary applications, exocytosis in neurons, endocrine neurons, neuroendocrine/endocrine cells, exocrine cells and hemopoietic cells are detected by the sensor devices based on their secreted granules which tend to alter the electrical properties of the devices. These secreted granules include, for example, dense-core vesicles, chromaffin granules, secretory granules, mucin granules, lamellar body, zymogen granules, casein vesicles, lysosome-related granules and other molecules.

In yet another application area, the nanostructure device of the invention is able to distinguish between apoptotic and non-apoptotic cells, which is critical to discriminating between pathological and non-pathological states in many types of cancer as well as to the detection of autoimmune and alloimmune disease states. In general, dying cells that undergo the final stages of apoptosis rearrange the cell surface and certain phospholipids on the cell surface. For example, phosphatidylserine that are normally found on cytosolic (inner) surface of a plasma membrane are redistributed during apoptosis to the membrane's extracellular surface. Because cell membranes are typically negatively charged, apoptosis results in a reduction of the overall charge which impacts device electrical properties upon the introduction of the cells onto the device surface. In many cases, this reduction of charge is in addition to an overall degranulation and secretion of cytoplasmic factors that take place during the apoptotic process.

According to another aspect of the invention, in addition to using unfunctionalized sensor devices to monitor real-time cellular responses, the detection capability of the nanosensor may be expanded via selective sensor surface functionalization which permits sensing of desired ions in addition to protons as well as sensing of disparate indicators for a variety of cellular assays. For example, a nanosensor may be functionalized by receptor molecules that bind to specific reagents, in which case a conductance change occurs in the corresponding sensor device. Given a p-type nanostructure, its conductance is adapted to increase when a macromolecule with negative surface charge binds to a nanostructure surface functionalized with receptor molecules, whereas the opposite response occurs when a positively-charged molecular binding occurs on a functionalized device surface. Hence functionalized nanostructures are well suited for performing selective label-free sensing of macromolecules. In addition to p-type nanostructure functionalization, selective n-type nanostructure functionalization is equally viable for performing label-free sensing. Details regarding n-type nanostructure sensors will be described below.

Some functionalization methods, such as hydroxyl-reactive schemes, require the functionalization of the entire sensor surface, including the underlying oxide, which diminishes sensitivity of the nanosensor due to binding competition. Thus, selective device functionalization is critical to the retention of sensitivity. A selective device functionalization process is provided according to an embodiment of the present invention, according to which nanostructures are introduced into an inert $N_2$ atmosphere, etched for about 5 seconds in 10:1 buffered oxide etch, rinsed and dried, coated with a functionalizing solution, and subjected to about a 2 hour UV treatment. Deprotection may be performed with 25% TFA in methylene chloride utilizing any prior art procedure. After washing and deprotecting, the yield of the device for effective selective functionalization is less than about 2%.

Dec-9-enyl carbamic acid tert-butyl ester may be used to functionalize nanosensor devices because this substance has been shown to confer amine functionality. Dec-9-enyl carbamic acid tert-butyl ester may be synthesized using any prior art procedure. This molecule is the same as 10-N-boc-amino-dec-1-ene, which has been shown to selectively functionalize silicon-over-oxide. All chemicals required for synthesizing dec-9-enyl carbamic acid tert-butyl ester may be purchased from Sigma-Aldrich. H NMR (500 MHz, CDCl$_3$) δ 5.79 (1H, ddt, J=17, 10.2, 6.7 Hz, CH), 4.98 (1H, dd, J=17, 1.7 Hz, CH), 4.91 (1H, dd, J=10.2, 1.7 Hz, CH), 4.88 (1H, s, NH), 3.09 (2H, m, CH$_2$), 2.03 (2H, m, CH$_2$), 1.47-1.29 (12H, m, CH$_2$), 1.44 (9H, s, CH$_3$); $_{13}$C NMR (500 MHz, CDCl$_3$) δ 156.06, 138.98, 114.20, 78.68, 40.62, 33.80, 30.12, 29.43, 29.29, 29.06, 28.92, 28.46, 26.83.

Figure 13:
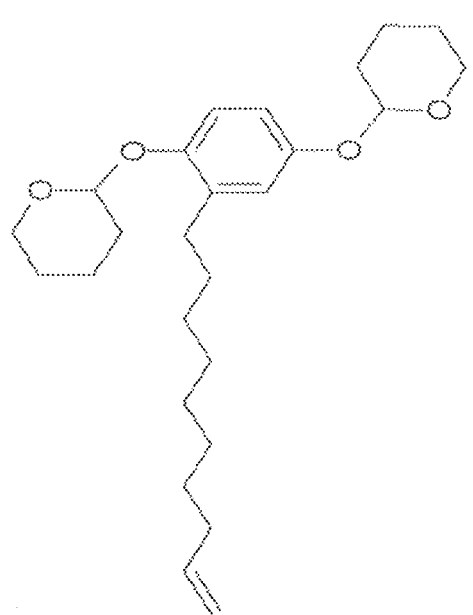
FIG. 13 illustrates an exemplary 2-[4-(tetrahydro-2H-pyran-2-yloxy) phenoxy]tetrahydro-2H-pyran molecule.

Another functionalization substance may be 2-[2-(undec-10-enyl)-4-(tetrahydro-2H-pyran-2-yloxy) phenoxy]tetrahydro-H-pyran. This molecule, whose structure is shown in FIG. 13, may be synthesized from 2-[4-(tetrahydro-2H-pyran-2-yloxy) phenoxy]tetrahydro-2H-pyran using any prior art processes. The intermediate may be synthesized by first adding dihydropyran (0.83 mL, 9.1 mmol) and pyridinium p-toluenesulfonate (0.11 g, 0.45 mmol) to a solution of hydroquinone (0.25 g, 2.3 mmol) in CH$_2$Cl$_2$ (3 mL). This reaction mixture is then stirred for about 12 hours and diluted with 10 mL of CH$_2$Cl$_2$. The mixture is subsequently washed by 3×5 mL of NaHCO$_3$ and 1×5 mL brine, dried over MgSO$_4$, and concentrated to a white solid. Silica gel chromatography (4:1 hexane/ethyl acetate) provides the di-tetrahydropyran hydroquinone as a white solid (0.48 mg, 75%).

In another embodiment, sensor functionalization may be performed using N-hydroxysulfosuccinimide/1-ethyl-3-(3-dimethylaminopropyl) carbodiimide hydrochloride (NHS/EDC) chemistry in 1×PBS, pH 7.4.

Figure 14A:
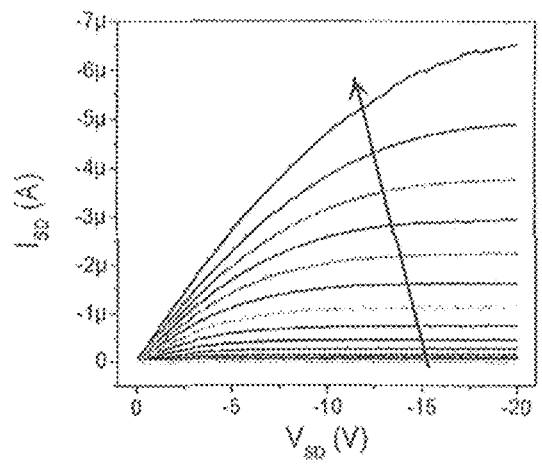
FIG. 14A and FIG. 14B illustrate source-drain current ($I_{sd}$) versus source-drain voltage (Vsd) for various gate-drain voltages (Vgd) applied to an unfunctionalized p-type nanowire sensor and a p-type nanowire sensor functionalized with dec-9-enyl carbamic acid tert-butyl ester.
Figure 14B:
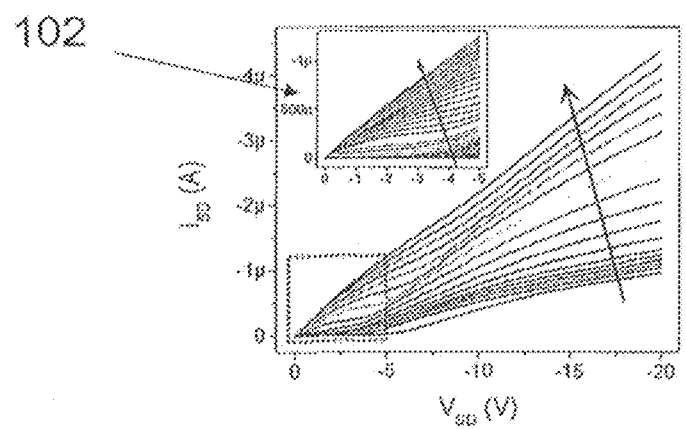
Figure 14C:
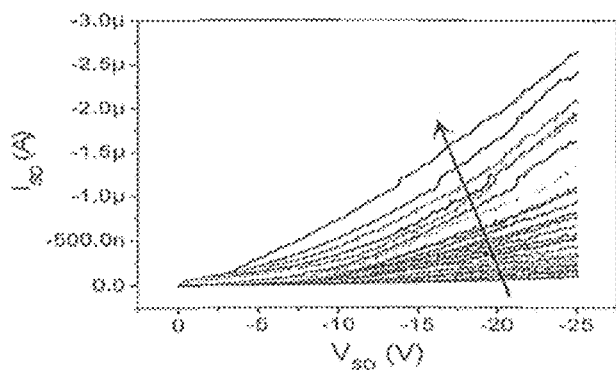
FIG. 14C illustrates $I_{sd}$ versus Vsd for various Vgd applied to a p-type nanowire sensor functionalized with 1-decene.

In certain embodiments, optimal device operation regions are determined for nanosensors selectively functionalized with each of the aforementioned substances. After device functionalization and deprotection with dec-9-enyl-carbamic acid tert-butyl ester, as shown in FIGS. 14A and 14B, respectively, absence of device pinch-off is observed for source-drain voltages $V_{SD}$ that are less than about −5V, hence suggesting a possible occurrence of parallel conduction at high bias through the functionalization layer which induces the creation of alternative conduction paths. However, at $V_{SD}$ greater than about −5V, the current leakage is negligible and the device is well suited for sensing. Thus, for certain functionalized nanosensor operations, the $V_{SD}$ is maintained at −2V or above for optimal sensing. Similar device operation regions may be applied to devices functionalized with 1-decene, whose conductivity response is shown in FIG. 14C. In certain implementations, dec-9-enyl-carbamic acid tert-butyl ester and 1-decene are preferred as functionalization substances over 2-[2-(undec-10-enyl)-4-(tetrahydro-2H-pyran-2-yloxy) phenoxy]tetrahydro-H-pyran because the latter substance may destroy the gating behavior of some nanostructure devices.

Functionalized nanosensors may be used to detect certain macromolecules based on selective protein binding. For example, nanosensors of the present invention can be used to detect protein biomarkers in a sample. In the detection of biomarkers, the nanostructure surface is functionalized with receptor molecules that specifically bind to the biomarker. For example, receptor molecules can include antibodies, antibody fragments, binding proteins, receptors, nucleotide sequences, and the like. In one example, nanostructure surfaces are functionalized with antibodies that specifically bind prostate-specific antigen (PSA) to allow the detection of PSA in a sample. In another example, nanostructure surfaces of CA15.3 in a sample. PSA and CA15.3 are both biomarkers associated with cancer. Other cancer biomarkers include, but are not limited to CA27.29, CEA, CA125, CA19.9, AFP, b-hCG, HER-2, KRAS, IL-6, IL-8, TRAIL, VEGF, TNF alpha, TGF alpha, Leptin, Prolactin, and the like. As would be understood by those skilled in the art, the type of biomarker detected by exemplary nanosensors of the present invention is not limited. Rather, any biomarker, in which a biomarker-specific receptor molecule can be functionalized to the nanostructure surface, can be detected.

Figure 15A:
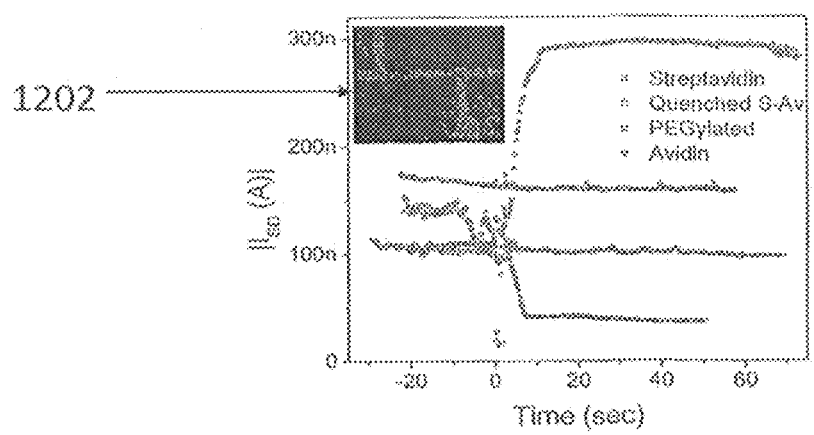
FIG. 15A illustrates conduction current responses in biotin-functionalized p-type nanowire sensors to the addition of streptavadin, quenched streptavidin, and avidin. Current response is also shown for a poly(ethylene glycol) (PEG) functionalized sensor device to the addition of streptavidin.

According to one example, electrical responses of biotin-functionalized device to the addition of 1 nM streptavidin, 1 nM biotin-quenched streptavidin, which is streptavidin pre-treated with 5 equivalents of biotin, and 1 nM avidin are determined. In order to avoid the problem of Debye screening, the salt concentrations in the buffers used for macromolecular sensing are chosen such that the Debye screening length ($\lambda_D$) is long enough not to impede sensing, but short enough that unbound macromolecules are screened. As shown in FIG. 15A, addition of a streptavidin solution results in a current increase in the nanosensor due to the protein's negative charge, hence demonstrating selective protein recognition and the dependence of device electrical signal on protein charge. The inset 1202 of FIG. 15A depicts an exemplary fluorescence micrograph image of a biontin-functionalized device having a width of about 500 nm and a thickness of about 40 nm that is treated with 1 nM of AlexFluor 655-linked streptavidin. However, addition of biotin-quenched streptavidin to a biotin-functionalized nanowire sensor elicits no response as demonstrated by the minimal fluctuation observed in the measured current shown in FIG. 15A. However, device current noticeably drops upon introduction of avidin, having an isoelectric point (pI) of about 0.5, due to avidin's positive charge. In additional examples of selective functionalization, a poly(ethylene glycol) (PEG) functionalized device yields no conduction response to an addition of 1 nM streptavidin (pI about 5.6), which is also illustrated in FIG. 15A.

Figure 15B:
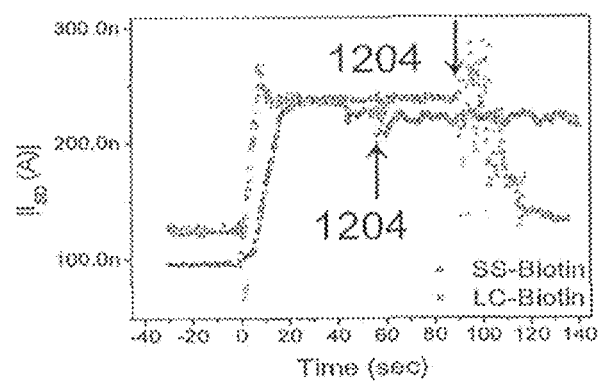
FIG. 15B demonstrates the reversibility of p-type nanowire sensor response to streptavidin addition and removal.

According to another embodiment, functionalized nanosensors are capable of reversing sensor responses to the addition or removal of reagents. In one exemplary implementation, the reversibility of sensor response to streptavidin addition and removal is demonstrated. Biotinylation, or biotin functionalization, of a single sensor is performed with a cleavable molecule SS-biotin, which may be processed from sulfo-NHS-biotin with a 2.4-nm linker having a dithiol bond. A second sensor is biotinylated with a noncleaving molecule LC-biotin that may be processed from sulfo-NHS-biotin with a 2.2-nm PEG linker. The response of each sensor to 1 nM streptavidin addition is similar, as illustrated in FIG. 15B. Subsequently, a reducing agent, tris(2-carboxyethyl)phosphine (TCEP), is added to the nanosensor, as shown by the arrow 1204 of FIG. 15B. The addition of the reducing agent cleaves the disulfide bond between the SS-biotin and the streptavidin which subsequently reverses the sensor response to baseline current. However, the LC-biotin control, which does not cleave disulfide bonds, is insensitive to the reducing agent and produced minimal response.

Molecular charge screening by dissolved solution counterions—Debye screening—on sensor response may be evaluated. Certain embodiments of the present invention were functionalized with APTS to effect amine-modified surfaces in high yield (>90%). Conventional shortcomings of the APTS technique—that essentially the entire NW-FET would be functionalized with amines—are thought to dramatically decrease sensing device sensitivity. Accordingly, certain preferred functionalized embodiments of the present invention were patterned to provide a final photoresist layer that exposed only a small region around the active devices as depicted by FIG. 3A.

Figure 16:
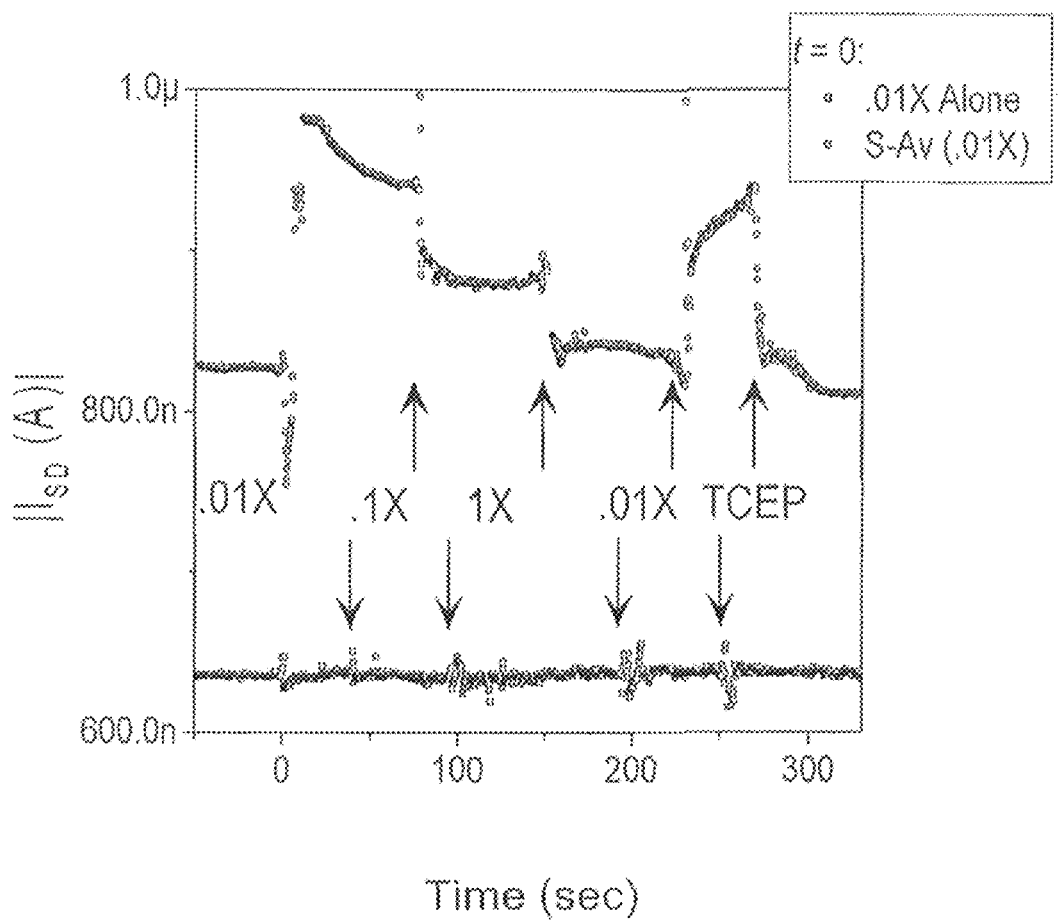
FIG. 16 shows biotin-functionalized sensor response ($|I_{SD}|$ vs. time) to varying buffer ionic concentrations with, and without, streptavidin addition at time=0.

Next, the effect of increasing buffer ionic strengths (decreasing Debye length—$\lambda_D$) on device recognition sensitivity was determined. A NW-FET device, of the present invention, was functionalized with a cleavable biotin molecule and, after establishing a baseline current in 0.01×PBS, 10 nM streptavidin was added in the same buffer. The binding of streptavidin, a negative protein with an isoelectric point (pI) of approximately 5.6, to the biotinylated device resulted in an increased $I_{SD}$ of the p-type device (FIG. 2B). The ionic strength of this buffer yields a $\lambda_D$ of approximately 7.3 nm. Thus the majority of the protein's charge is unscreened at the NW-FET surface (FIG. 16B). A ten-fold increase in the ionic strength of the buffer (0.1×PBS, $\lambda_D$ approximately 2.3 nm) partially screens streptavidin's intrinsic charge and a further ten-fold increase in buffer ionic strength (1×PBS, $\lambda_D$ approximately 0.7 nm) effectively screens most of the protein's charge, returning the $I_{SD}$ approximately to its baseline value (FIG. 16B). The device current level begins to recover to its 0.01×PBS value after a subsequent decrease in ionic strength by solution exchange with this buffer. The addition of the reducing agent tris(2-carboxyethyl)phosphine hydrochloride (TCEP), which cleaves the biotin linker and, thus, removes streptavidin from the sensor surface, returns $|I_{SD}|$ to its original baseline level, see FIG. 16B. As a control, the same series of solution exchanges was applied to a nominally identical biotinylated device using streptavidin-free buffers (FIG. 16B). The absence of a change in signal demonstrates that the NW-FET response is independent of Ionic strength (e.g., $\lambda_D$).

Figure 17A:
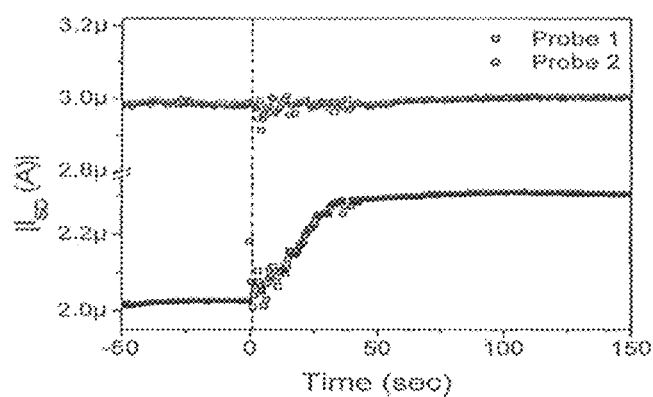
FIG. 17A shows the response of NW-FETs functionalized with the Probe 1 DNA strands to the addition of 10 pM solutions of target DNA strands. Solution exchange occurs at time=0, highlighted by the dashed line.
Figure 17B:
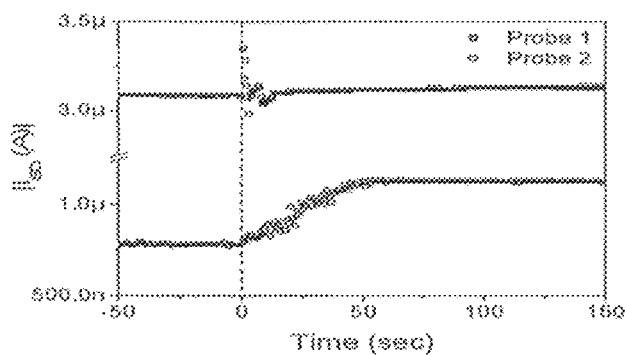
FIG. 17B shows the response of NW-FETs functionalized with the Probe 2 DNA strands to the addition of 10 pM solutions of target DNA strands. Solution exchange occurs at time=0, highlighted by the dashed line.

For yet other certain preferred embodiments, cross-comparison assays were performed to determine device suitability for specific ssDNA strand recognition. For example, two exemplary NW-FET devices were functionalized with the DNA-P(1) sequence and two devices with the DNA-P(2) sequence. All such devices having a Debye length ($\lambda_D$) of about 3.3 nm relative to the NW-FET sensor surface. Under active measurement conditions ($V_{SD}$=−2V, $V_{GD}$=−35V) and after the establishment of a baseline signal in 0.05×PBS, the solution was exchanged with 10 pM solutions of target DNA, either DNA-T(1) or DNA-T(2), in the same buffer. FIGS. 17A and 17B show the responses of the DNA-P(1)- and DNA-P(2)-functionalized devices, respectively, to DNA-T(1) and DNA-T(2). In both cases, complementary pairing results in an increase in $|I_{SD}|$, as expected for a p-type device, while the noncomplementary negative controls show little change in signal, indicating a buffer with an optimal $\lambda_D$. The near-negligible signal of the negative controls indicates the $\lambda_D$ of about 3.3 nm effectively screens unbound DNA.

These results demonstrate the importance of selecting a buffer with an appropriate $\lambda_D$ to ensure proper NW-FET sensing. Careful control of the solution Debye length ($\lambda_D$) ensures that specific binding of macromolecules contribute to sensor response. An autonomous system for analyte detection must properly take these issues into account, such as employing ionic strength feedback control. This demonstration also profiles an application where charge distribution may enable unique measurements of the configuration of surface-bound species.

Figure 18:
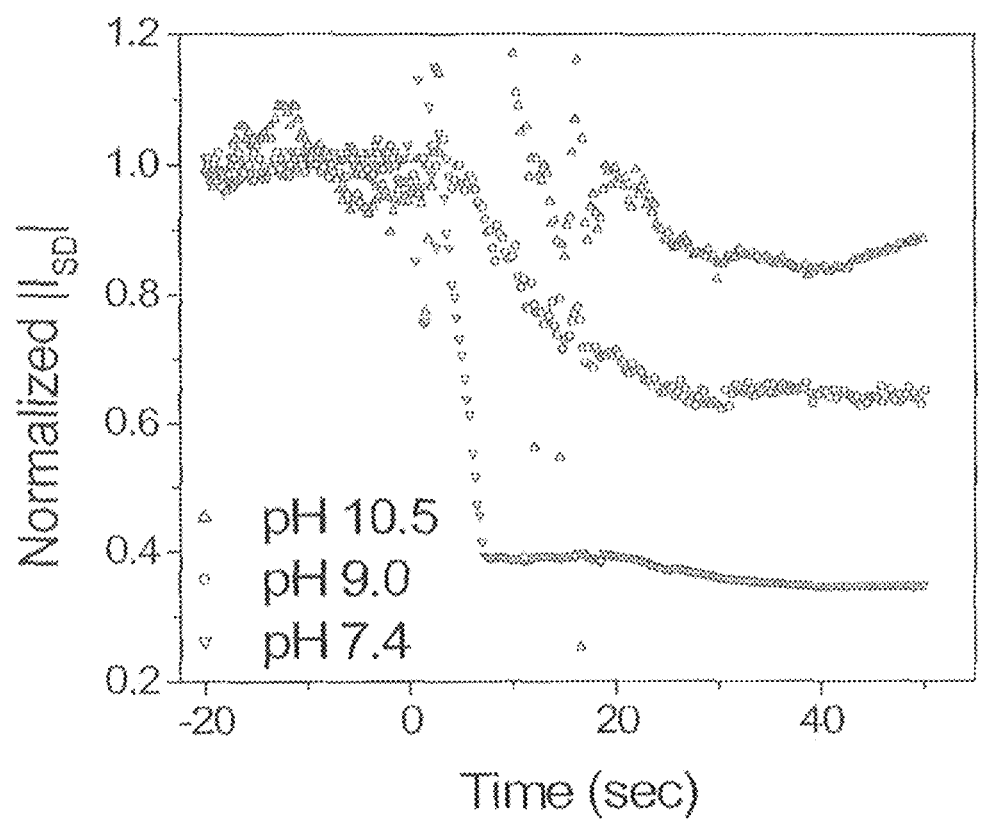
FIG. 18 demonstrates device sensitivity of biontin-functionalized p-type sensors to the addition of advin solutions with varying pH.

Protein sensing ability of the functionalized nanosensor devices may be optimized with regard to its sensitivity to protein charge and concentration, according to another embodiment of the invention. This determination is made based on measured conductivity response resulting from the introduction of three solutions with varying pH to a biotinylated nanosensor, where each solution includes 1 nM of avidin and an appropriate pH buffer. Even though avidin is positive in neutral solutions due to its high isoelectric point (pI about 10.5), its effective charge may be decreased by the increase in solution pH. FIG. 18 demonstrates decreased device sensitivity in correlation to increased solution pH.

Hence, the value of |pH$_{solution}$−pI| needs to be maximized to optimize protein sensing. In other implementations, protein sensing is optimized by the use of a linear solution pH gradient to determine unknown protein pIs.

In general, 0.1×PBS having pH of 7.4 may be utilized for biotin-streptavidin/avidin sensing, where the 0.1×PBS has a Debye screening length ($\lambda_D$) of about 2.2 nm. Despite the fact that calculating the actual amount of protein captured and sensed has inherent uncertainties, about 7 fg of protein is estimated to bind to a single sensor, assuming that the sensor has a cross-sectional width of about 100 nm to and a cross-sectional thickness of about 40 nm, and the protein concentration is about 1 avidin molecule/25 nm$^2$. In addition, Biotinylation may be performed with N-hydroxysulfosuccinimide (sulfo-NHS)-biotin, sulfo-NHS-SS-biotin, or sulfo-NHS-LC-biotin (Pierce Chemical) at pH of 10.5.

Figure 19A:
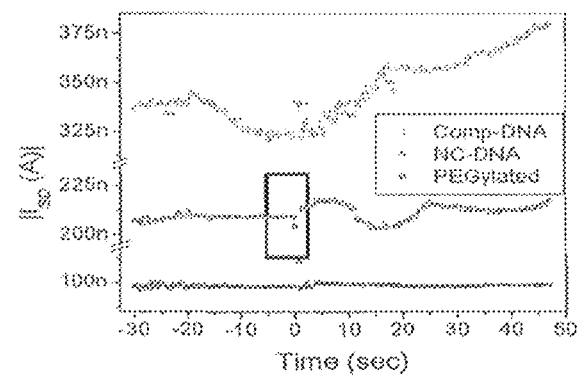
FIG. 19A illustrates current responses in DNA-functionalized p-type sensors to the addition of a complementary and a non-complementary 15-mer concentration.

Selectively functionalized sensor devices may also be utilized in the detection of complementary DNA, as shown in FIG. 19A. In particular, two exemplary sensor devices are functionalized with a 20-mer, 5'-thiol ss-DNA, with subsequent introduction of either a complementary or a non-complementary 15-mer at a 100 fM concentration on each device. The sensor response to complementary strand addition is observed to be more than the non-complementary strand addition.

Figure 19B:
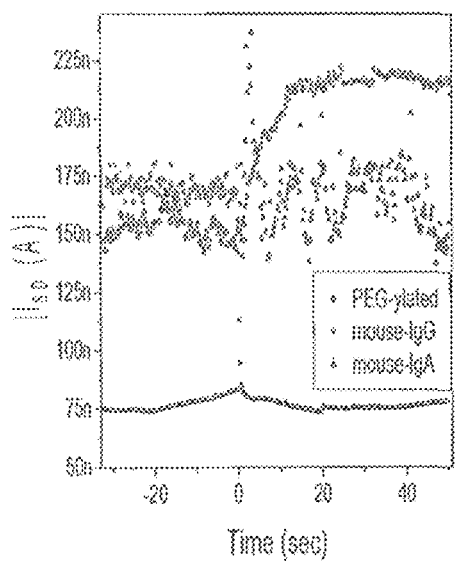
FIG. 19B and FIG. 19C illustrate current responses in a goat-α-mouse IgG functionalized p-type sensor and a goat-α-mouse IgA functionalized p-type sensor to the introduction of mouse IgG and mouse IgA, respectively.
Figure 19C:
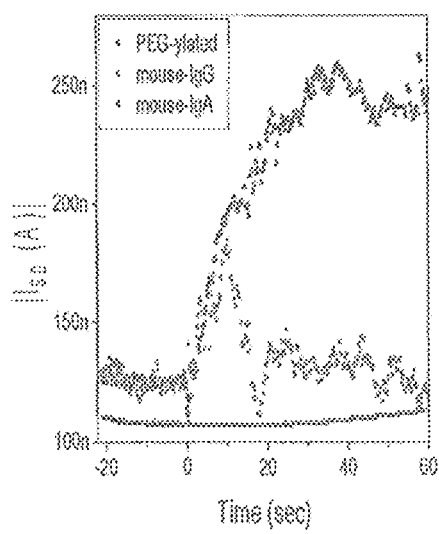

In another embodiment as shown in FIGS. 19B and 19C, a protein assay is performed by functionalizing two devices with goat-α-mouse IgG and two additional devices with goat-α-mouse IgA. One device from each group is used to sense the presence of mouse IgG and the other mouse IgA, where both solutions have about 100 fM concentrations. Sensing is subsequently performed at pH of 8.5 to maximize protein charge while maintaining protein conformation. As seen in FIGS. 19B and 19C, the appropriate ligand is detected in each case, while current in non-immune devices remained relatively constant. Thus, the ability of this functionalization approach for the detection of antibodies at less than about 100 fM concentrations is demonstrated. In certain examples, the captured antibodies are bound using NHS/ethylene dicarbodiimide coupling techniques. The sensing may be performed in a 1 mM sodium bicarbonate buffer, having pH of 8.4 and Debye screening length ($\lambda_D$) of about 6.8 nm.

The functionalized nanostructure sensors used in the aforementioned implementations may be nominally similar, with, in one embodiment, device cross-sectional thickness about 40 nm and device cross-sectional width varies from about 50 nm to about 150 nm.

According to another aspect of the invention, the nanosensor devices, whether functionalized or unfunctionalized, are used for complementary sensing. N-type inversion-mode devices may be fabricated on the same wafer as p-type accumulation-mode devices to support the complementary sensing ability. An $I_{SD}(V_{SD})$ dependence plot, with $V_{GD}$ varying from 0 to 40V in 1V increments, is shown in FIG. 6B for an exemplary n-type sensor device having a width of about 50 nm and a thickness of about 40 nm. The $I_{SD}(V_{GD})$ dependence plot for $V_{SD}$=1V is shown in the inset of FIG. 6B. As with the p-type $I_{SD}(V_{GD})$ behavior illustrated in FIG. 6A, the small hysteresis between forward and reverse $I_{SD}(V_{GD})$ slopes in the inset in FIG. 6B suggests minimal defect-induced charge trapping in the n-type nanowire sensor device. The observed n-type behavior is possibly due to the polarity of the contacts to the device, which may be controlled by contact implantation or physical definition. For simplicity, surface accumulation charge caused by RIE pattern definition may be used, which is sufficient to invert the contact, thereby decreasing the contact resistance and enabling inversion-mode behavior. This results in ambipolar behavior, as evident in the inset of FIG. 6B. The n-type and p-type nanostructure sensors may be incorporated into an integrated electronic system to perform functions such as on-chip signal processing, error detection, and complementary error detection for the purpose of avoiding false positives.

Figure 20A:
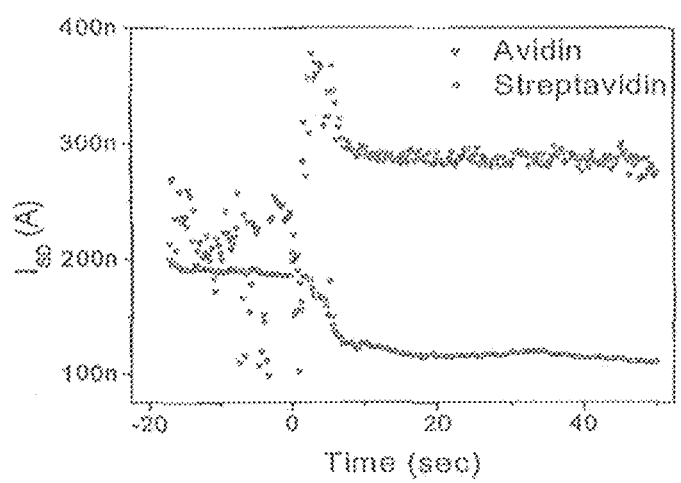
FIG. 20A illustrates conduction current responses in biotin-functionalized n-type sensors to the introduction of streptavadin and avidin.
Figure 20B:
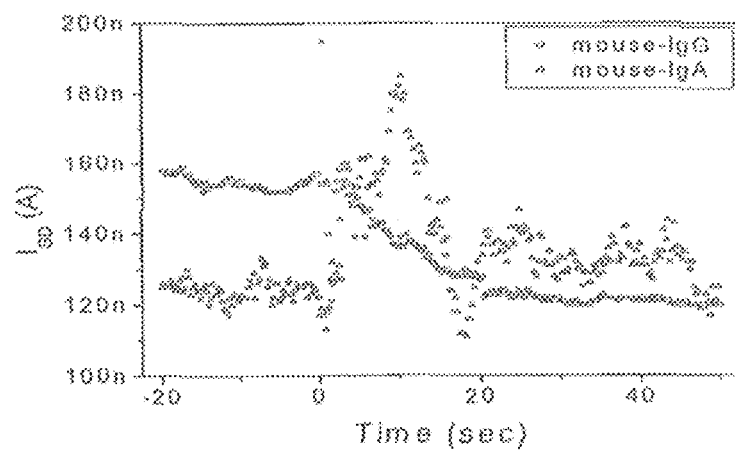
FIG. 20B illustrates current responses in a goat-α-mouse IgG functionalized n-type sensor to the addition of mouse IgG.

In certain embodiments, the response of a biotinylated n-type inversion-mode device to 1 nM streptavidin and avidin, introduced at time=0, is shown in FIG. 20A. These devices react with the opposite sense of the p-type accumulation-mode device shown in FIG. 15A. Additionally, two p-type nanostructure sensors are functionalized with goat-α-mouse IgG and demonstrate appropriately inverted and null responses to the presence of mouse IgG and mouse IgA, respectively. The mouse IgG and mouse IgA are at about 100 fM concentrations when introduced to the functionalized device at time t=0. The resulting conduction responses, as depicted in FIG. 20B, show opposite sense from the reaction of a p-type accumulation-mode device. Thus, the complementary sensing ability of the nanostructure sensors of the current invention has also been demonstrated for the detection of antibodies at less than about 100 fM concentration.

In certain implementations, measurements of current response may be taken at 0.25-second intervals with $V_{SD}$ and $V_{GD}$ held constant. For implementations involving macromolecule addition, time=0 may be defined as the onset of protein/DNA addition. In addition, functionalization processes may run for about 100 seconds.

In certain exemplary configurations, a mixing device, such as the solution chamber of FIG. 6, is used to continuously mix solutions of interest after they are injected into a nanosensor device. The volume of liquid in the solution chamber may be about 10 µL which includes 10 µL of buffer at the onset of each sensing run that is displaced by 100 µL of protein/DNA solution of which 10 µL remains.

The aforementioned nanostructure sensors have important medical diagnostic applications. For example, the sensors may be used to differentiate between healthy cells and diseased cells based on monitoring of real-time cellular responses. The efficiency of this technique lays in its label-free detection approach according to which cells being tests for pathogens do not need to be tagged with any visualization beacons or labels. In addition, the smoothness of the active surfaces of the nanostructure sensors and their large surface-to-volume ratio make these sensors highly sensitive to bound molecular charges, hence enabling accurate and efficient detection of specific label-free reagents. Moreover, the crystalline semiconductor materials used to fabricate these sensors facilitate their seamless integration into any CMOS systems, particular as a part of molecular or cellular arrays for performing wide-scaling complementary error detection and integrated signal processing.

In one aspect, the present invention relates to nanosensor devices with uniform characteristics. Reproducible fabrication of devices described herein produce devices with minimal device to device variability. The methods provided herein describe a "top-down" fabrication technique that produces minimal fluctuations between devices. Device to device variability has been problematic in the field, as it requires the need for each device to be individually calibrated. The present invention is based upon the finding that nanostructure FETs can be fabricated with very similar transport characteristics. The uniform nanosensor devices of the invention can be used as quantitative sensors for the easy quantitative detection of biological or chemical processes.

For example, the uniform nanosensor devices of the invention can be used to quantitatively detect the concentration of a biomarker in a test sample. The uniformity of the devices allows for the comparison of outputs across different devices. The uniformity of the devices of the present invention can be determined by numerous methods. For example, the devices can be examined for their similarity in threshold voltage ($V_T$), baseline current, transconductance, and the like.

In one aspect, the present invention relates to methods of fabricating a nanostructure sensor with uniform characteristics. The methods of the invention can comprise techniques known in the art, including but not limited to, TMAH wet etching, plasma etching, sputter etching, reactive-ion etching (RIE), photolithography, electron beam lithography, and the like. Exemplary fabrication procedures used to generate nanostructure sensors with uniform characteristic are provided elsewhere herein. Such procedures produce devices with similar threshold voltage, baseline current, transconductance, and the like.

Sensor Calibration

Nanowire Field Effect Transistor (FET) sensor technology, including the various nanosensors contemplated and described herein, has demonstrated tremendous potential for point-of-care (POC) applications and has been successfully used for detection of proteins (Cui et al., 2001, Science, 293: 1289-1292), oligonucleotide sequences (Zhang et al., 2008, Nano Lett, 8(4): 1066-1070), cellular function (Stern et al, 2008, Nano Lett, 8(10): 3310-3314), virus detection (Patolsky et al., 2004, Proc Natl Acad Sci, 101(39): 14017-14022) and enzymatic activity (Stern et al., 2010, Small, 6(2): 232-238). As mentioned previously, electronic label-free detection is based on nanosensor surface modification with specific receptors capable of recognizing and binding the desired target molecules. Upon binding, the nanosensor surface potential is changed due to the electric charge present on the bound molecule, which modulates the nanosensor surface potential and thus causes an Increase or decrease of carriers and device current (Bergveld, 1981, Sens Actuators, 1: 17-29).

While several qualitative studies have demonstrated the true power of this detection method, the lack of quantitative results diminishes the competitiveness of the BioFET technology with the existing state-of-the-art techniques. A number of previous experiments have been performed on "bottom-up" or chemical vapour deposition (CVD) grown nanowires, but this method suffers from large device-to-device variation in electrical parameters such as threshold voltage, mobility and transconductance (Ishikawa et al., 2009, ACS Nano, 3(12): 3969-3976). Given these fluctuations, Individual device calibration is thus required for quantitative analysis, thus eliminating one of the primary advantages of a microfabrication approach, i.e. multiplexing.

In order to minimize the variations of sensor electrical properties and sensing signal, two different approaches may be used. In one embodiment, device solution transconductance, $g_{m,sol}$ is used to normalize the total current change, Al (Ishikawa et al., 2009, ACS Nano, 3(12): 3969-3976; Stern et al., 2010, Small, 6(2): 232-238) caused by analyte binding. In another embodiment, device response is normalized by device baseline current level, $1_o$, established prior to analyte addition (Bunimovitch et al., 2006, J Am Chem Soc, 128: 16323-16331). However, all these methods use bottom-up grown nanowire, which are problematic because of their non-uniform characteristics (Stern et al., 2005, Nanotechnology 16).

In one aspect, the present invention relates to methods of calibrating nanostructure biosensors to control for variability in device characteristics. Variability in the fabrication of Individual biosensors can lead to the production of devices with slight or significant variations in their electrical parameters such as threshold voltage and transconductance. The present invention is based upon the discovery that the initial current rate, as measured by nanoribbon biosensors, scales linearly with the initial current and transconductance. Thus, these specific parameters of the individual devices can be used to internally calibrate the devices, thereby eliminating the need for calibration of each individual device to a known standard.

The methods relate to converting or calibrating the observed changes in drain source current ($I_{DS}$) after the addition of a solution comprising an analyte of interest, to provide an output that can be compared across devices. This allows straight forward quantification of the analyte concentration. Further, the methods of the invention allow for multiplexing of simultaneous detection using multiple devices on a single array.

The present methods utilize the initial current rate observed after analyte addition, rather than total change in current or endpoint detection. The initial current rate observed following analyte addition is indicative of the initial kinetic binding rates of the analyte of interest to its binding partner. Following the well-known ligand-receptor kinetics, sensor signal increases linearly with time. In addition, initial rates at low relative analyte concentrations are directly proportional to species concentration. Furthermore, saturation value of device response (i.e. total change in current) is weakly dependent on species concentration for reversible reactions with a low dissociation constant (such as antibody-antigen reactions), thus making initial rate a more reliable parameter than endpoint detection.

Figure 42:
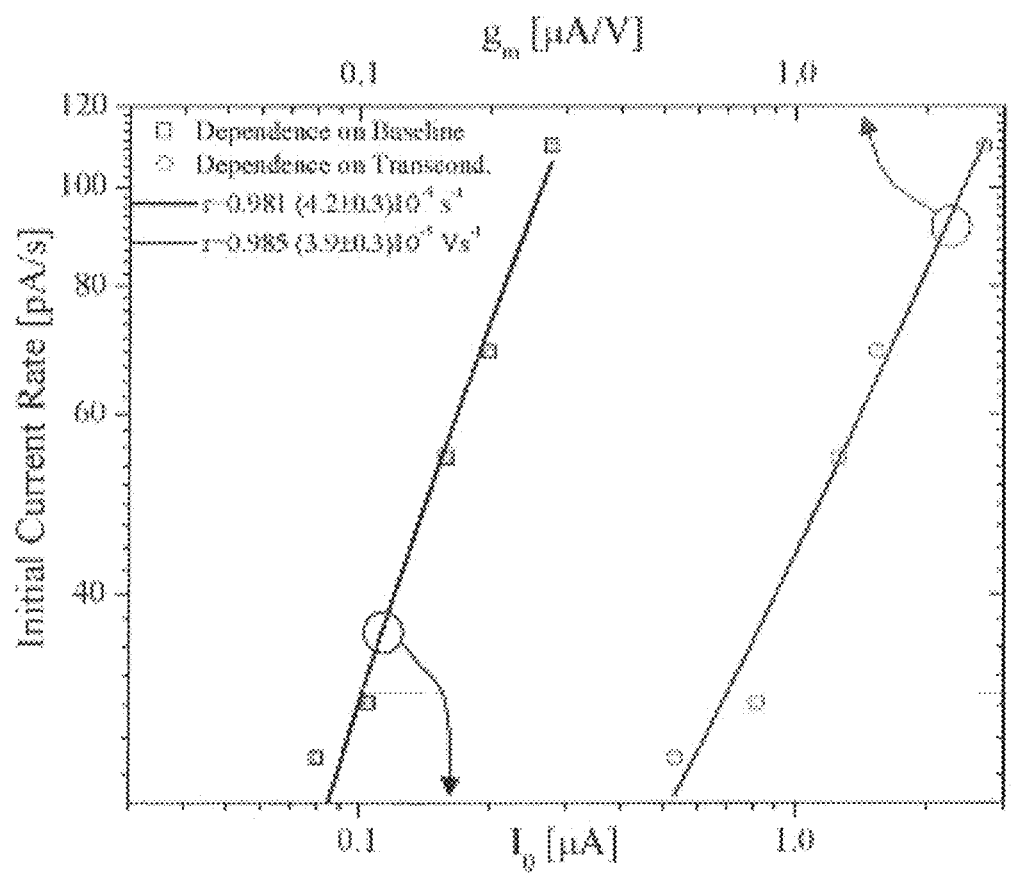
FIG. 42 depicts a plot of initial current rate of five devices shown in FIG. 41, as a function of both baseline currents and device solution transconductances at $V_{backgate}$=-3 V and $V_{sol}$=0 V. Error bars are approximately the size of the data points. The relative standard deviations for initial current rates, baseline currents and transconductances are 0.7%, 0.3% and 0.6%, respectively. Both fits are linear (y=kx), shown on a log-log scale for clarity.

As demonstrated herein, initial current rate observed after analyte addition scales linearly (y=kx) with the initial baseline current ($I_o$) of the device and transconductance ($g_m$) (FIG. 42). Therefore, the response for a given device after the addition of an analyte can be easily normalized to provide a normalized device signal. In one embodiment, the normalized device signal is given by: initial current rate divided by baseline current. Baseline current of the device is found as the observed current ($I_{DS}$) prior to analyte addition. In another embodiment, the normalized device signal is given by: initial current rate divided by transconductance. With the drain as a common ground for both the device and the gate, the transconductance of the device is found through measuring the change in current divided by the change in $V_{GS}$, with $V_{DS}$ held constant, prior to analyte addition. In one embodiment, transconductance of the device is determined by using solution gating, wherein an electrode immersed in the surrounding solution produces a change in the gate voltage.

The normalized device signals, obtained through the methods of the present invention take into account the inherent variability between fabricated devices to produce a metric that may be compared across devices. In one embodiment, for a given analyte, the normalized device signals, obtained through the methods of the present invention detected over numerous devices, vary by less than 20%. Preferably, the normalized device signals vary by less than 10%. More preferably, the normalized device signals vary by less than 5%.

The present invention also provides methods for quantifying the response of a nanostructure biosensor. In one embodiment, the present invention provides methods for quantifying the concentration of a biomarker in a solution. The methods provided herein, enable the reliable quantification from a given device without the need to calibrate the given device to a known standard. Rather, the methods provide for the determination of a calibration curve, generated by measuring the normalized device signal for at least 2 known standards, which can then be used for all devices to quantify the biomarker of interest. For example, in one embodiment, a calibration curve can be generated for which all devices on a single array can use to quantify detection, thereby allowing multiplexing. In another embodiment, all individual devices can use the same calibration curve to quantify detection. Therefore, any device can be used to quantitatively sense, regardless of the fabrication technique used to make the device or the individual device characteristics. The present methods account for variability among device parameters, thereby allowing all devices to utilize the same calibration curve. Thus, the present method allows for quicker and easier quantification from a nanostructure biosensor device.

The methods of the invention include the generation of a universal calibration curve, usable for all devices, for the reliable quantification of a given analyte or biomarker. The methods are based upon the discovery that the initial current rate after the addition of an analyte scales linearly with baseline current ($I_o$) and device transconductance ($g_m$). Therefore, in one embodiment, the generation of a universal calibration curve comprises obtaining the normalized device signal in response to the addition of a known standard. In one embodiment, the known standard is a sample with a known concentration of the given analyte. In one embodiment, the method comprises obtaining a second normalized device signal in response to the addition of a second known concentration of the analyte. With the knowledge of the normalized device signals from the known concentrations, a calibration curve can be fit between the two data points. In one embodiment, normalized device signals in response to additional known concentrations are obtained in order to provide additional data points for which the calibration curve can be fit. In one embodiment, multiple measurements of the normalized device signal are obtained for each known concentration, thereby producing a mean normalized device signal (and standard error) for each known concentration. In one embodiment, the multiple measurements are made over multiple devices. In one embodiment, the data points obtained from the detection of known concentrations are plotted such that the mean normalized device signal is along the y-axis and the analyte concentration is along the x-axis. A calibration curve can then be fit to the plotted data points. The method of the invention is not limited to the type of fit of the calibration curve to the data points. For example, the calibration curve can have linear fit, logarithmic fit, polynomial fit, and the like. In one embodiment, the normalized device signal for each data point is given by the initial current rate divided by the baseline current. In another embodiment, the normalized device signal for each data point is given by the initial current rate divided by the transconductance.

The methods of the present invention also relate to use of the generated universal calibration curve to reliable quantify an unknown concentration of an analyte in a test sample. In one embodiment, the methods include observing the current of a nanostructure biosensor in response to addition of the test sample. In one embodiment, the method includes obtaining a normalized device signal from the observed response. In one embodiment, the normalized device signal in response to the addition of the test sample is given by the initial current rate, following the addition of the test sample, divided by the baseline current. In this aspect, the universal calibration curve for the given analyte, generated by normalizing initial current rate to baseline current observed in the detection of known concentrations, is used to quantify the concentration of the analyte in the test sample. The equation of the calibration curve, fit to the data from the known concentrations, is then used to determine the concentration of the analyte in the test sample.

In another embodiment, the normalized device signal in response to the addition of the test sample is given by the initial current rate, following the addition of the test sample, divided by transconductance. In this aspect, the universal calibration curve for the given analyte, generated by normalizing initial current rate to transconductance observed in the detection of known concentrations, is used to quantify the concentration of the analyte in the test sample. The equation of the calibration curve, fit to the data from the known concentrations, is then used to determine the concentration of the analyte in the test sample.

In one embodiment, the quantification obtained through the methods of the invention differs from the actual concentration by less than 20%. Preferably, the quantification differs from the actual concentration by less than 10%. More preferably, the quantification differs from the actual concentration by less than 5%.

As would be understood by those skilled in the art, the present methods can be used for the detection of any analyte of interest. That is, the methods are not limited to the detection of any particular analyte. Further, the methods are not limited to changes in current in response to the binding of a particular biomolecule. As described elsewhere herein, nanostructure biosensors can be utilized to detect a wide range of physiological processes, including T cell activation. Therefore, the methods of the present invention also provide the ability to obtain normalized device signals and calibration curves for these assays. The methods thereby provide the ability to quantitatively detect differences as mediated by different conditions of a given assay, and to reliably compare differences measured over multiple devices.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and use the sensors of the present invention and practice the methods of nanosensor calibration. The following working examples therefore, specifically point out the preferred embodiments of the present invention, and are not to be construed as limiting in any way the remainder of the disclosure.

Example 1: Initial Rates Used to Sense Analyte Concentration in Nanoribbon Sensors Twenty-five nm-thin nanoribbon devices were fabricated according to the exemplary nanoribbon fabrication method detailed elsewhere herein, and illustrated in FIG. 21, wherein Ohmic contacts were incorporated into devices.

Figure 22A:
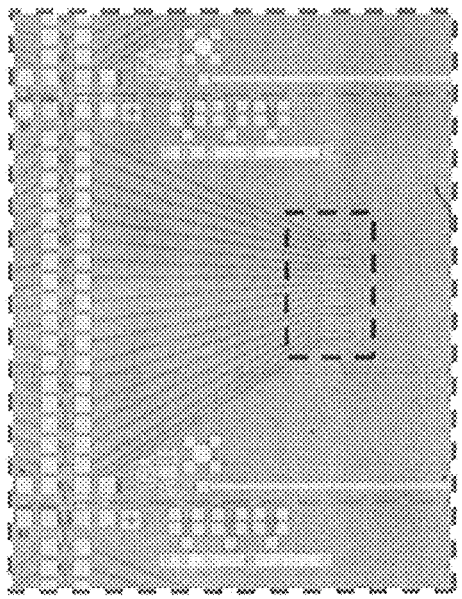
FIG. 22A through FIG. 22D, is a series of images representing optical micrographs of exemplary nanoribbon sensors.
Figure 22B:
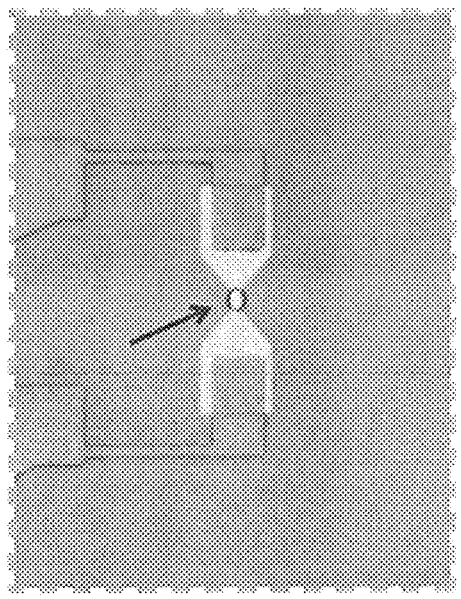
Figure 22C:
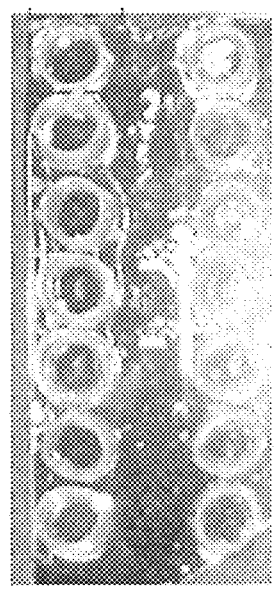
Figure 22D:
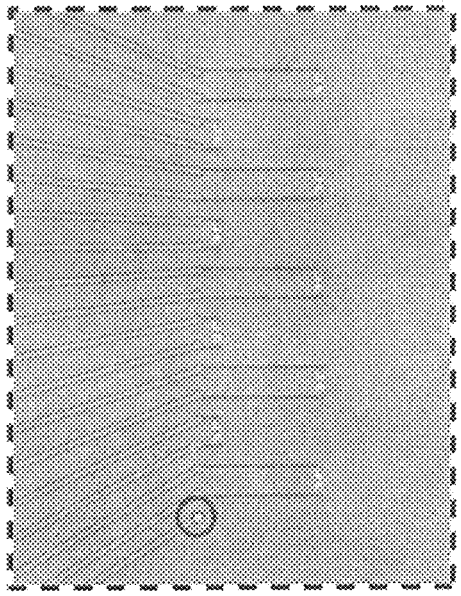
Figure 23A:
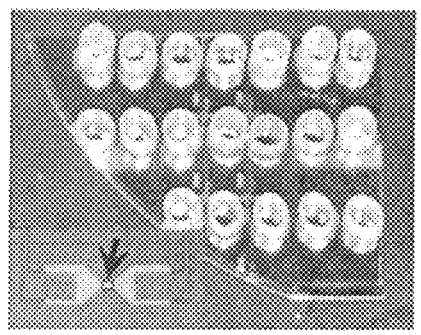
FIG. 23A through FIG. 23D, is a series of images illustrating electrical characteristics of nanosensors.
Figure 23B:
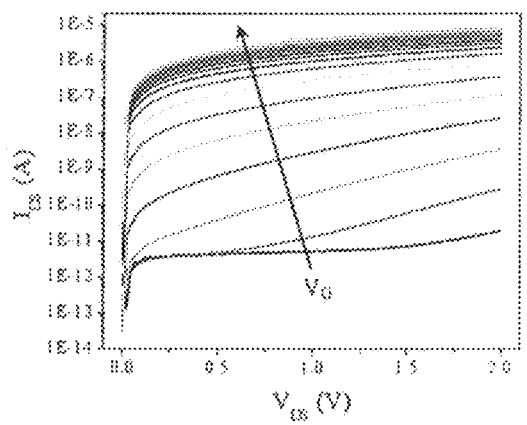
Figure 23C:
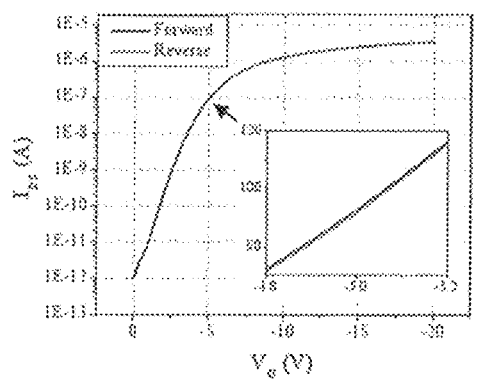
Figure 23D:
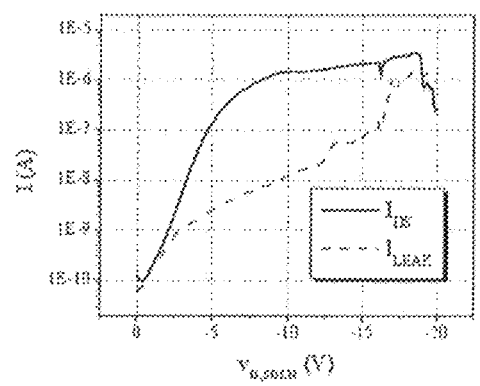

Device images are given in FIG. 22 and FIG. 23A. Electrical characterization verified that this approach produced high-quality devices, with on/off ratios of $>10^6$ (FIG. 23B) and small hystereses between forward and reverse $I_{DS}(V_G)$ sweeps (FIG. 23C). Surface functionalization did not compromise device electrical characteristics and solution gating ($V_{G,\ SOLN}$) demonstrated that $V_G=-5$ V was an optimal operating point for sensing studies (FIG. 23D).

Devices were functionalized either with anti-PSA or anti-CA15.3. As described elsewhere herein, the passivation layer was deposited by PL after APTS functionalization. Devices were diced with a glass scribe and functionalized with either anti-PSA (Accurate Chemical Co.) or anti-CA15.3 (Alpha Diagnostics) using standard EDC/sulfo-NHS chemistry (Hermanson, 1996, Bioconjugate Techniques, Elsevier Science & Technology, New York) in 1×PBS, pH 7.4. After washing with 1×PBS the surface was blocked with a 10% FBS solution and subsequently washed with 0.01×PBS. Reservoirs were filled with 5 μL of 0.01× PBS and remained filled with this volume until sensing measurements were performed.

Antibodies were immobilized to the sensor using NHS/EDC chemistry. To verify that the signal from binding proteins would not be screened by the buffer solution, direct measurements of the amount of the signal that would be unscreened were done by varying buffer salt concentration (Stern et al., 2007, Nano Lett, 7: 3405). This study indicated that approximately 50% of the signal was not screened by the buffer solution.

Figure 25A:
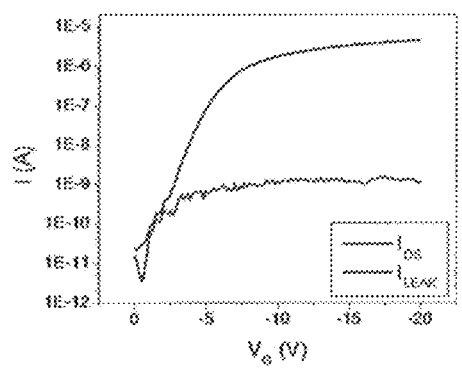
FIG. 25A through FIG. 25C, is a series of graphs illustrating the correlation of I with $V_G$.
Figure 25B:
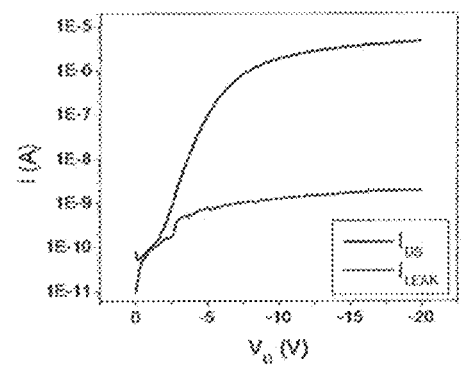
Figure 25C:
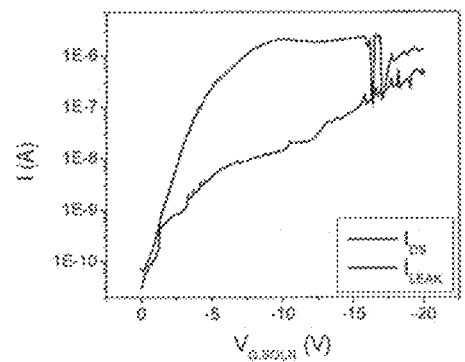

Next, these devices were applied to microfluidic purification chip (MPC)-purified whole blood samples to sense the biomarkers (Stem et al., 2010, Nat Nanotechnol, 5(2): 138). For solution phase sensing, reservoirs were created by epoxying thin-walled, PTFE tubing to the chip (Stem et al., 2007, Nature 445:519). Solution-gating was performed using an exposed electrode on the chip surface (circle, FIG. 22C). Representative devices functionalized with anti-PSA or anti-CA15.3 antibodies were gated in the presence of 10 μL of sensing buffer in the reservoir. Anti-PSA and anti-CA15.3-functionalized device backgating (using the handle wafer) is illustrated in FIGS. 25A and 25B, respectively, and solution gating is illustrated in FIG. 23D and FIG. 25C, respectively. All devices used in these experiments were 1 μm in width and had a 2 μm length exposed to the sensing solution (FIG. 22D). For the solution phase sensing measurements, a 1 mM bicarbonate buffer solution was used, which has a Debye screening length of $\mu_D$=9.6 nm. To verify that the signal from binding proteins would not be screened by the buffer solution, direct measurements of the amount of the signal that would be unscreened were carried out by varying buffer salt concentration (Stem et al., 2007, Nano Lett. 7:3405). After protein injection and stabilization in the 1 mM bicarbonate buffer ($\lambda_D$=9.6 nm), the solution was then changed to a low ion concentration buffer (0.1 mM bicarbonate), which should extend the Debye length to ~30 nm. The signal was observed to increase, to its maximum unscreened value. A high salt concentration was then added (10 mM NaCl, $\lambda_D$~3 nm), and the signal was observed to decrease far below the initial (absorbed protein) value, and close to baseline. Nine devices for CA15.3 gave an average of 61% unscreened (1.6% SEM-standard error of the mean, 1 mM bicarbonate buffer). Twenty PSA devices gave a slightly lower value of unscreened (46%, 2.6% SEM, 1 mM bicarbonate buffer).

For all sensing measurements the SPA was used in sampling mode, measuring $I_{DS}$ at 0.5 sec intervals, and mixing was performed with manual pipetting. As observed previously, injection transient noise was present in all measurements (Stern et al., 2007, Nature 445:519) and devices required 1-5 mins for current stabilization in sensing buffer (Stem et al., 2007, Nano Lett. 7:3405). The sensing reservoir was filled with 5 μL of pure sensing buffer and, after device current stabilization, the solution to be sensed was added. For consistency, solution addition is defined as occurring at time=0. For all pure buffer sensing measurements, 5 μL of the sample was added to the reservoir.

Figure 24A:
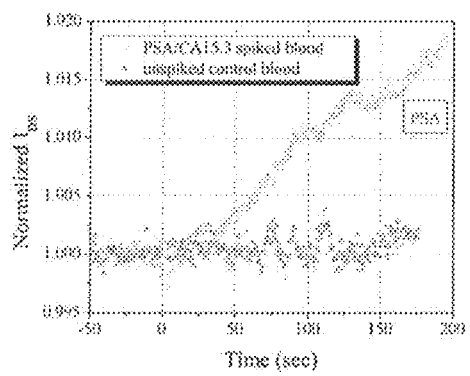
FIG. 24A through FIG. 24D, is a series of graphs illustrating sensing measurements using the label-free sensing. All sensing measurements were performed at $V_{DS}$=1V and $V_G$=−5V and all sample introductions occurred at time=0. Normalizations were performed by dividing device currents by the pre-addition (t<0) current level average. $V_{DS}$ corresponds to drain-source voltage.
Figure 24B:
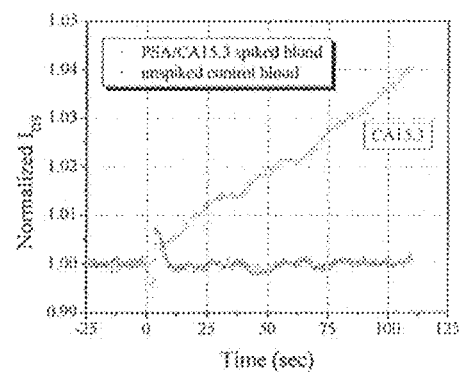

The normalized responses of these same devices to MPC-purified, antigen-spiked blood samples containing both 2.5 ng/mL PSA and 30 U/mL CA15.3 (as well as negative controls) are shown in FIG. 24A and FIG. 24B, respectively. After the injection transient noise subsides (Stem et al., 2007, Nature, 445: 519-522), device current levels were increased by antigen binding due to the negative charge conferred to the antigens by the basic sensing buffer. Similar signals were obtained with a PSA/CA15.3 spiked sensing buffer positive control, and no device response was observed with an unspiked, MPC-purified blood negative control. To reduce potential transient electrical signals upon injection, buffer salt concentrations of the functionalized devices and the MPC-purifies samples are kept the same. The positive signal is observed to increase linearly in time, following well-known ligand-receptor kinetics, (Cantor et al., 1980, Biophysical Chemistry: Part III: the Behavior of Biological Macromolecules, Freeman) in which initial rates at low relative analyte concentrations are directly proportional to the species concentration (Homola, 2003, Anal Bioanal Chem, 337: 528-539). In fact, the asymptotic saturation value of the device response is weakly dependent on the concentration for reversible reactions with a low dissociation constant (Cantor et al., 1980, Biophysical Chemistry: Part III: the Behavior of Biological Macromolecules, Freeman) which is the case for the antigen-antibody interactions. Thus, the initial kinetic reaction rates were focused upon instead of endpoint detection (Homola, 2003, Anal Bioanal Chem, 337: 528-539).

Figure 24C:
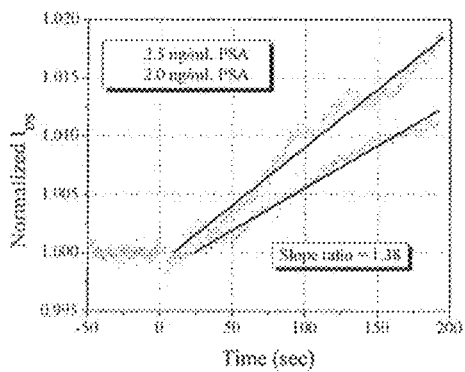
Figure 24D:
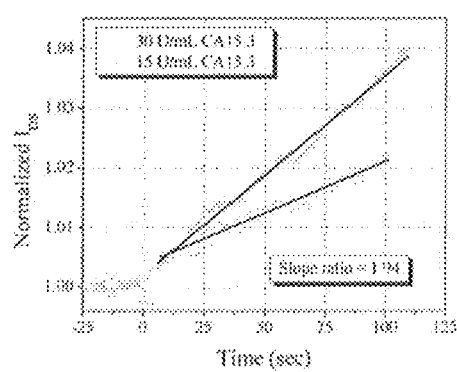

Using these rates, a quantification of analyte concentrations (against a known) can be made, as shown in FIG. 24C and FIG. 24D. Whole blood samples spiked with 2 ng/mL PSA and 15 U/mL CA15.3 were MPC purified and sensed with anti-PSA and anti-CA15.3 functionalized devices. Using the slope of the normalized device temporal response, it was found that slope ratios of both the PSA and CA15.3 responses agree quite well with the initial spiked whole biomarker concentrations. For PSA, the slope ratio is 1.38, compared with a concentration ratio of 1.25; for CA15.3, the slope ratio is 1.94, versus a concentration ratio of 2.0. It should be noted that this quantification occurs in the presence of another species, demonstrating selectivity as well.

Further details of the above experiments are provided in International Patent Application PCT/US10/25412, the entire contents of which are incorporated by reference in their entirety.

Example 2: Series a Fabrication Process—Nanoribbon BioFETs

Described herein is an exemplary fabrication method used to construct nanoribbon sensors (bioFETs) that have uniform characteristics.

Eight inch silicon-on-insulator wafers with 70 nm active and 145 nm buried oxide (BOX) layer were purchased from SOITEC. The doping in the active and handle wafers was boron at $10^{15}$ cm$^{-3}$. The wafers were laser-cut to 4-inch diameters by Silicon Quest International. Processing was performed in part at the Cornell Nanoscale Science and Technology Facility and the Yale Center for Microelectronic Materials and Structures. All photolithography steps were performed using Shipley S1808, S1813, or S1827 photoresist and an EV Group 620 mask aligner. All masks were 5" and were purchased from PhotoSciences, Inc. The active layer was thinned to 25-50 nm (depending on the Intended application) by thermal growth of oxide at 1100° C. using an MRL Industries furnace after MOS cleaning. The oxide thickness was determined using a Woollam Variable Angle Spectroscopic Ellipsometer.

Figure 26:
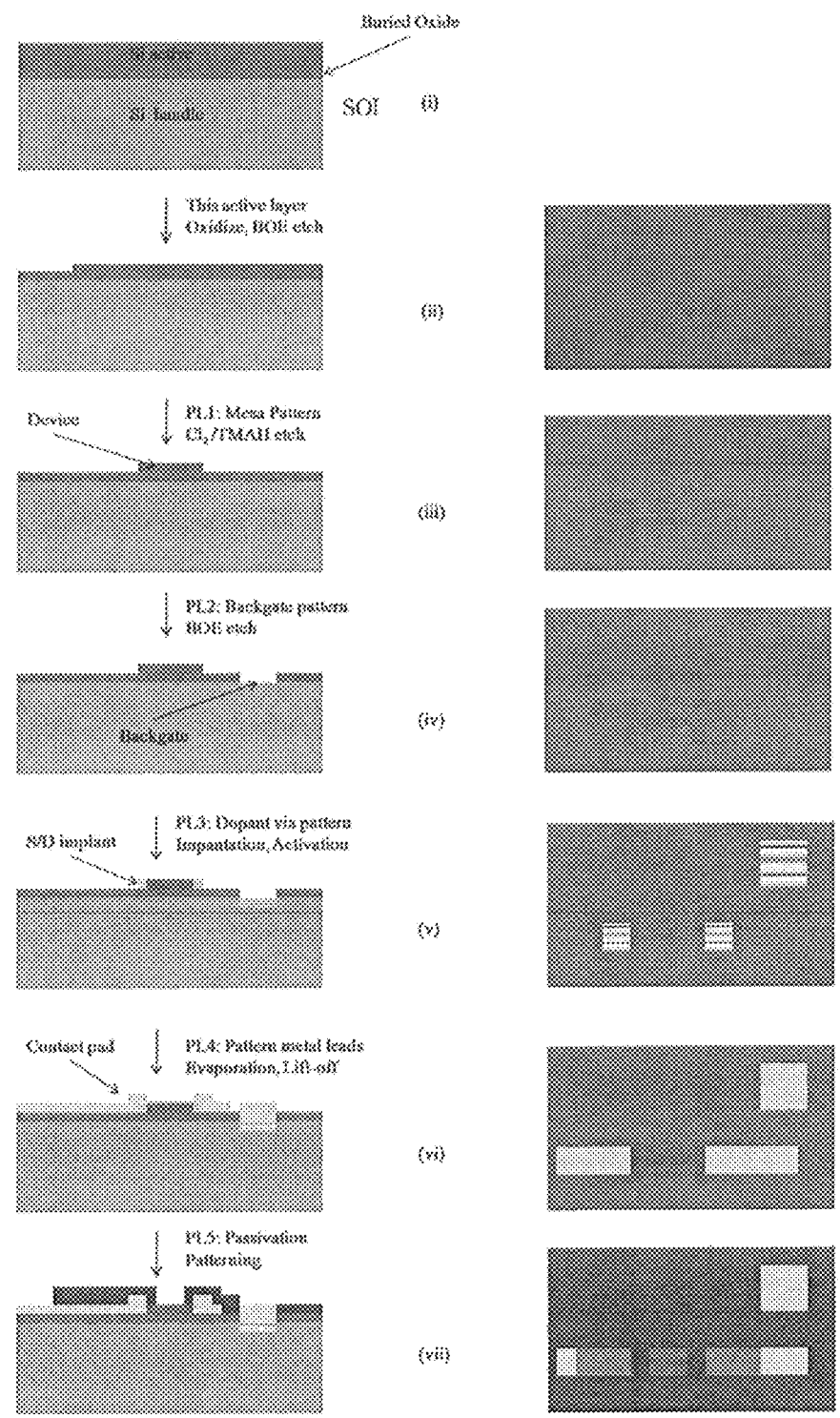
FIG. 26 illustrates the fabrication of top-down silicon bio-field effect transistors (bioFETs) using only optical lithography.

As shown in FIG. 26(iii) the active parts of the sensor (mesas) were patterned in the first lithography step followed by a chlorine reactive-ion etching (RIE, Oxford PlasmaLab 100). Chlorine chemistry was used because it does not etch silicon oxide, thus the BOX serves as an etch-stop. Photoresist was stripped by ozone plasma using a Mercator Control System Inc. HF-6 barrel asher.

The second PL step (FIG. 26(iv)) is used to pattern contacts to the silicon handle wafer which serves as an electronic backgates for device characterization. Vias through the BOX to the backgate were etched using 10:1 buffered oxide etch (BrandNu Labs) and photoresist was stripped using acetone and isopropanol (BrandNu Labs).

The third PL step (FIG. 26(v)) patterned degenerate doping regions for contacts to device and backgate contacts. A Boron implant dose of $5\times10^{15}$ cm$^{-2}$ at 8 KeV was performed at a 7° tilt by Core Systems. In FIG. 26(v), the doped regions are shown as graded pattern. Photoresist was then stripped by ashing, followed by wafer exposure to piranha. The dopant was activated by annealing the wafers at 900° C. in nitrogen in a MRL Industries furnace after MOS cleaning.

The fourth PL step (FIG. 26(vi)) patterned metal leads, pads, and contacts. A 145 nm Al (99.99%, Kurt J. Lesker Co.)/5 nm TiW (90/10, w/w, Kurt J. Lesker Co.) liftoff evaporation was performed by electron-beam deposition in a Kurt J. Lesker EJ1800 Thin Film Deposition System. After liftoff, achieved by wafer sonication in acetone, the wafers were rapid-thermal annealed (RTA) for 1 min at is 450° C. in a Surface Sciences Integration Solaris 150 RTA. Sequential RTA/electrical characterization steps dictated that these conditions were required in order to form Ohmic contacts to devices.

Figure 27:
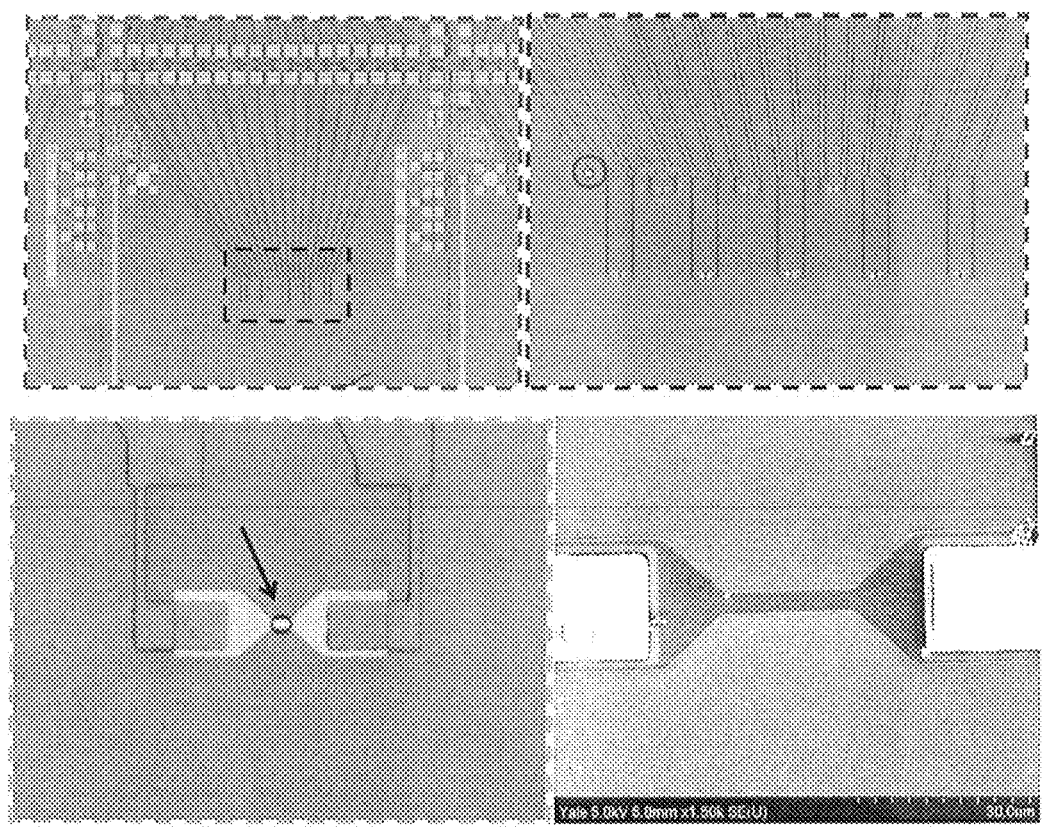
FIG. 27 depicts optical and SEM micrographs of bioFETs. The arrow points to the sensing area of the device exposed to solution.

The fifth PL step (FIG. 26(vii)) patterned S1808 photoresist as a passivating layer across the chip to prevent leakage. Exposed surfaces included contacts and active device regions. The photoresist was hardbaked for 1 hr at 140° C. Note that this step was performed after 3-aminopropyltriethoxysilane (APTES) functionalization as resist is dissolved by the organic solvents required for that process. In such case the whole wafer was immersed in the 20% (v/v) toluene solution of APTES. Optical and Scanning Electron (SEM) micrographs of completed devices are shown in the inset in FIG. 27.

Example 3: Series A BioFET Electrical Characterization

Upon fabrication but before sensing experiments it is important to explore the quality of fabricated devices. Typical methods are similar to the ones used for MOSFETs and include I-V characteristics, threshold voltage distribution and mobility extraction. These parameters carry important information about the uniformity and quality of fabrication process. Without a good control over device parameters and due to device-to device variation, the application of bioFETs as a quantitative sensor is practically impossible.

In order to understand how device response is related to its electrical characteristics it is necessary to characterize device prior to and after the functionalization. Device electrical characteristics were assessed by simultaneous measurement of $I_{DS}$–$V_{GS}$ characteristics of up to 8 devices on a given die. To understand the uniformity of our fabrication process the variation of the threshold voltage as a function of its position on the wafer was investigated. For a group of 106 devices used for this experiment, the average for threshold voltage $<V_T>=-2.3$ V was obtained. The standard deviation for the sample was calculated to be $\sigma_{VT}=0.15$ and the standard error of the mean $\sigma_{<VT>}=0.014$ V.

Figure 28:
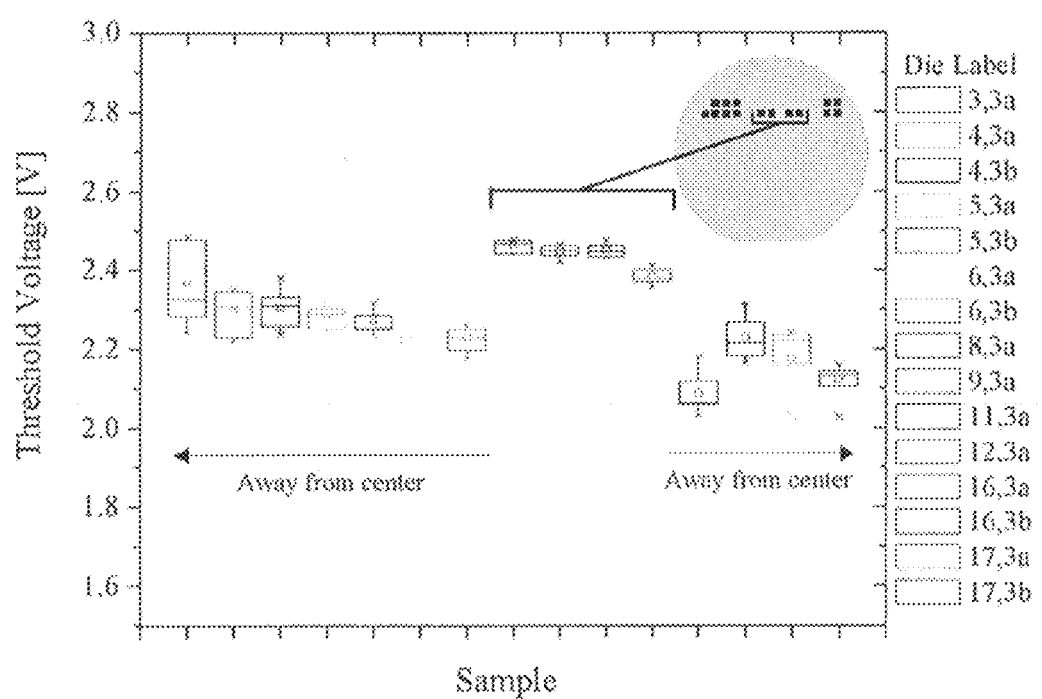
FIG. 28 is a graph depicting the threshold voltage distribution of nanoribbon devices across a 4" wafer. Each data point is a 5×5 mm die containing up to 8 devices. The inset shows approximate die positions on the wafer. Notation a) and b) in the die label refers to the lower and the upper half of a 10×5 mm die. (10,3) is a center column die.

The distribution of threshold voltages is dominated by the nonuniform thickness of the active silicon layer (70±10(3σ) nm) and variations in the thickness of the dry oxide used for thinning of active region (estimated to be around 7-8% across the 4" wafer). FIG. 28 shows the variations of threshold voltage for a series of dies, and the corresponding wafer map (inset). In regions with minimal thickness fluctuations (wafer center), threshold voltage variation of 8 mV, in terms of standard error of the mean, was obtained.

The off current of dry devices is measured to be on the order of 1 fA to 100 fA which yields good on/off ration of approximately 5-6 orders of magnitude. The average backgated subthreshold swing is (630±30) mV/dec which corresponds to the thickness of 145 nm of buried oxide layer between the active and the handle (backgate). The average drift mobility obtained from peak transconductance is calculated to be (93±17) cm$^2$/Vs which is in agreement with previously obtained values measured on fully depleted SOI RIE defined devices (Stern et al., 2007, Nature, 519-522; Sun et al., 1980, IEEE Journal of Solid-State Currents, 15: 562-573; Habicht et al., 2010, Solid-State Device Research Conference (ESSDERC), Sevilla, pp. 372-375).

Figure 29:
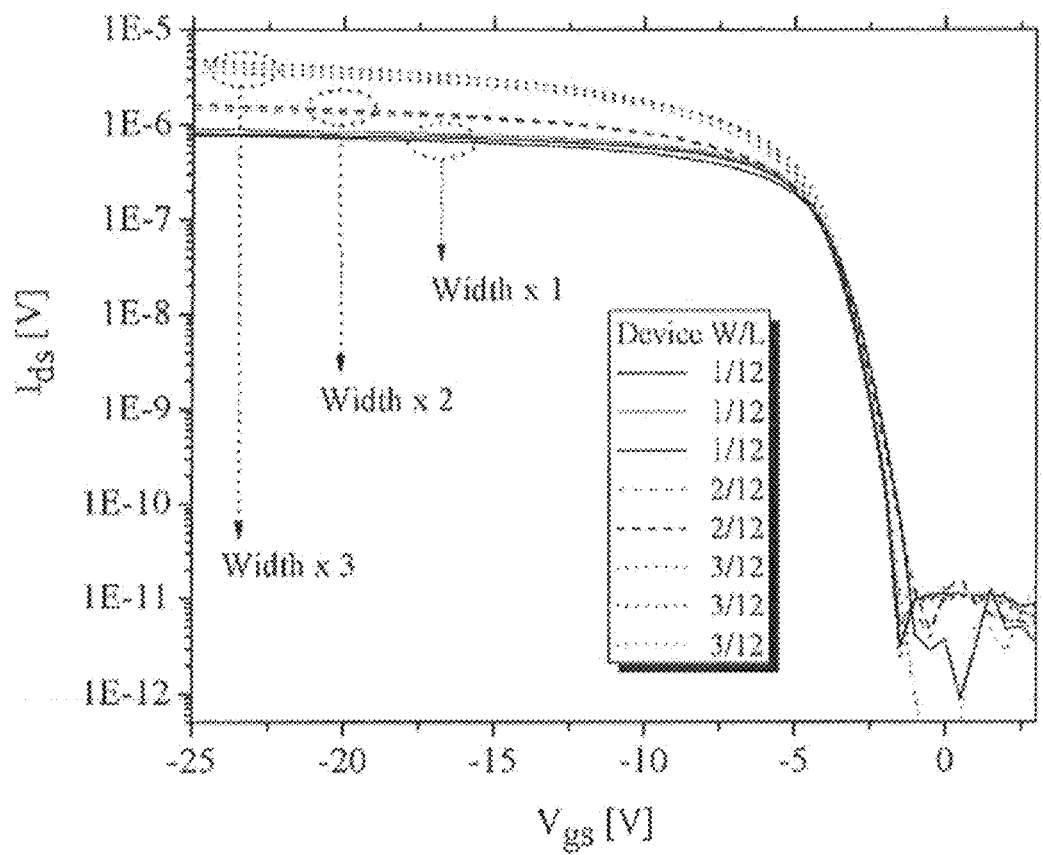
FIG. 29 is a graph depicting the I-V characteristics of 8 devices on the same chip scanned using a multiplexing system. Device sizes are purposely varied to explore the scaling effects. The floor for leakage current (1-10 pA) is limited by the leakage current of operational amplifiers used in the transresistance amplifiers.

FIG. 29 shows I-V characteristics for 8 devices on the same chip. As expected from a p-type accumulation mode device, it exhibits negative threshold voltages, $V_T=(-2.43\pm0.09)$V. The average subthreshold swing is calculated to be 700 mV/dec which is in agreement with the backgate oxide thickness of 145 nm. The relation between the subthreshold swing and oxide capacitance $C_{ox}$ is given by (Muller et al., 2003, Device Electronics for Integrated Circuits, John Wiley & Sons):

$$S = 2.3\frac{kT}{q}\frac{(C_{ox}+C_{it}+C_d)}{C_{ox}} \qquad (4)$$

where $C_{it}$ is an interface trap capacitance, $C_d$ is a capacitance of the depletion region, $k_b$ is the Boltzman constant and T is absolute temperature. Assuming that there are no interface traps (for rough estimate only) the lower boundary value for the subtreshold swing is then:

$$S = 2.3\frac{k_B T}{q}\left(1+\frac{C_d}{C_{ox}}\right) \approx 60\frac{mV}{dec}\left(1+\frac{t_{ox}}{x_d}\frac{\epsilon_{si}}{\epsilon_{ox}}\right) = 580\frac{mV}{dec} \qquad (5)$$

Figure 30:
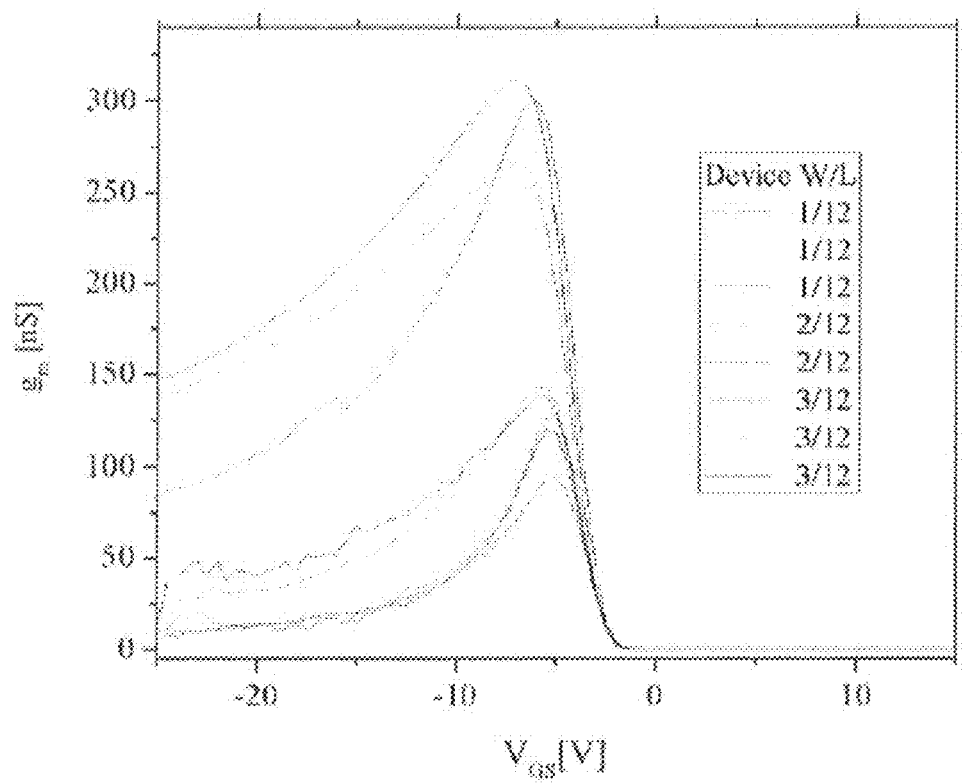
FIG. 30 is a graph depicting transconductance of bioFETs as a function of backgate voltage.

Another parameter that describes the quality of bioFETs is the transconductance $g_m$ and carrier mobility p. One can extract the value of the field effect mobility from the peak transconductance. FIG. 30 shows gate voltage $V_G$ dependence of transconductance $g_m$ for devices having various widths and fixed length of 12 μm. Using the relation between the transconductance and mobility $$\mu_{FE} = \frac{L}{W} \frac{g_m}{C_{ox} V_{ds}} \quad (6)$$

one estimates the average mobility for bioFETs to be (80±20) cm$^2$ V$^{-1}$ s$^{-1}$ which is in good agreement with the other work on p-type SOI RIE-defined devices (Habicht et al., 2010, Solid-State Device Research Conference (ESSDERC), Sevilla, pp. 372-375).

Example 4: Series B Fabrication Process—Nanoribbon/Nanowire BioFET

Described herein is another exemplary fabrication procedure for the construction of nanostructure sensors (bioFETs) which have uniform characteristics.

The second generation of bioFETs uses several additional steps in the fabrication process in order to improve overall device quality and allow electron beam lithography as well as on chip pseudo-reference electrode. One of the major shortcomings of the first generation bioFETs was the insulator, native oxide, used as the sensing surface. Due to the high porosity of native oxide the life-time of bioFETs was relatively short and varied from 15 min to 2 hours. Some of the Series A devices have shown significant drift and/or leakage current in solutions (Jamasb et al., 1998, Sens Actuators R: Chemical, 49: 146-155).

Figure 31:
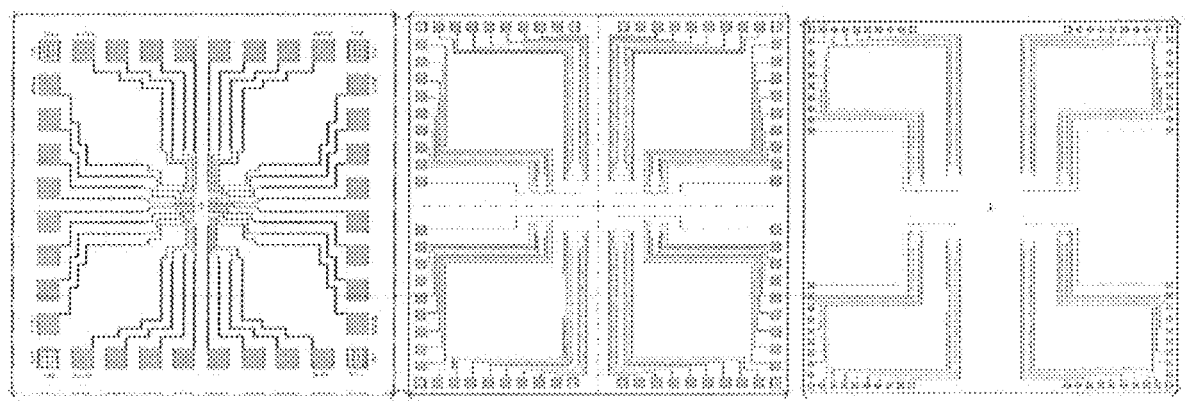
FIG. 31 depicts the layout of Series B bioFETs illustrating three different die sizes and chip layouts. The die sizes from left to right are 3.3×3.3, 6.6×6.6, and 10×10 nm.

In addition to changes in fabrication process, the overall layout of the chips was changed to accommodate more devices for multiplexed sensing and microfluidic integration. Three die sizes were designed: the 3.3 mm by 3.3 mm (16 devices total), 6.6 mm by 6.6 mm (32 devices), and 10 mm by 10 mm (32 devices) (FIG. 31). The latter two have staggered devices (4 columns each having 8 devices) which will allow for simultaneous sensing of up to four different biomarkers.

The active silicon layer of the SOI wafers was thinned down using thermal oxidation.

Figure 32:
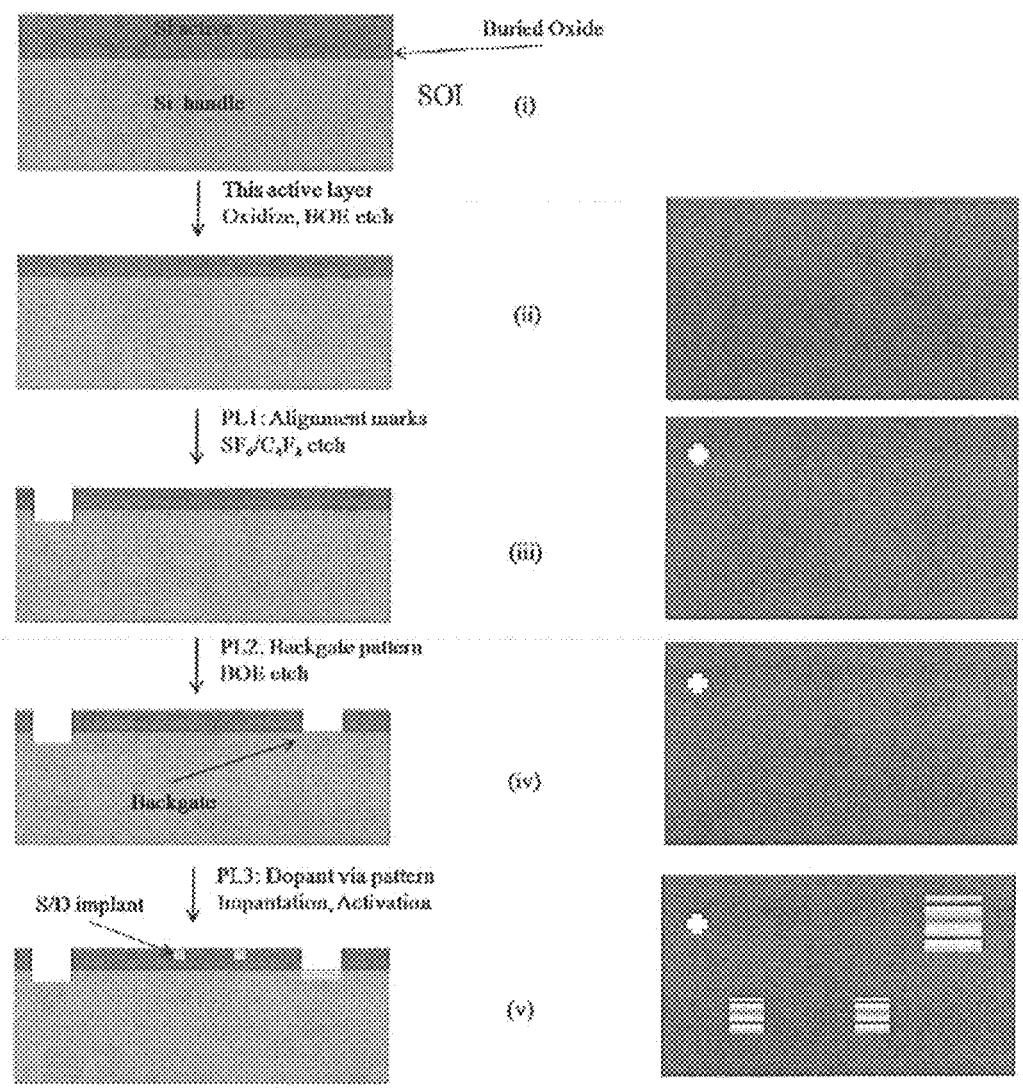
FIG. 32 depicts an exemplary Series B bioFET fabrication process.
Figure 32:
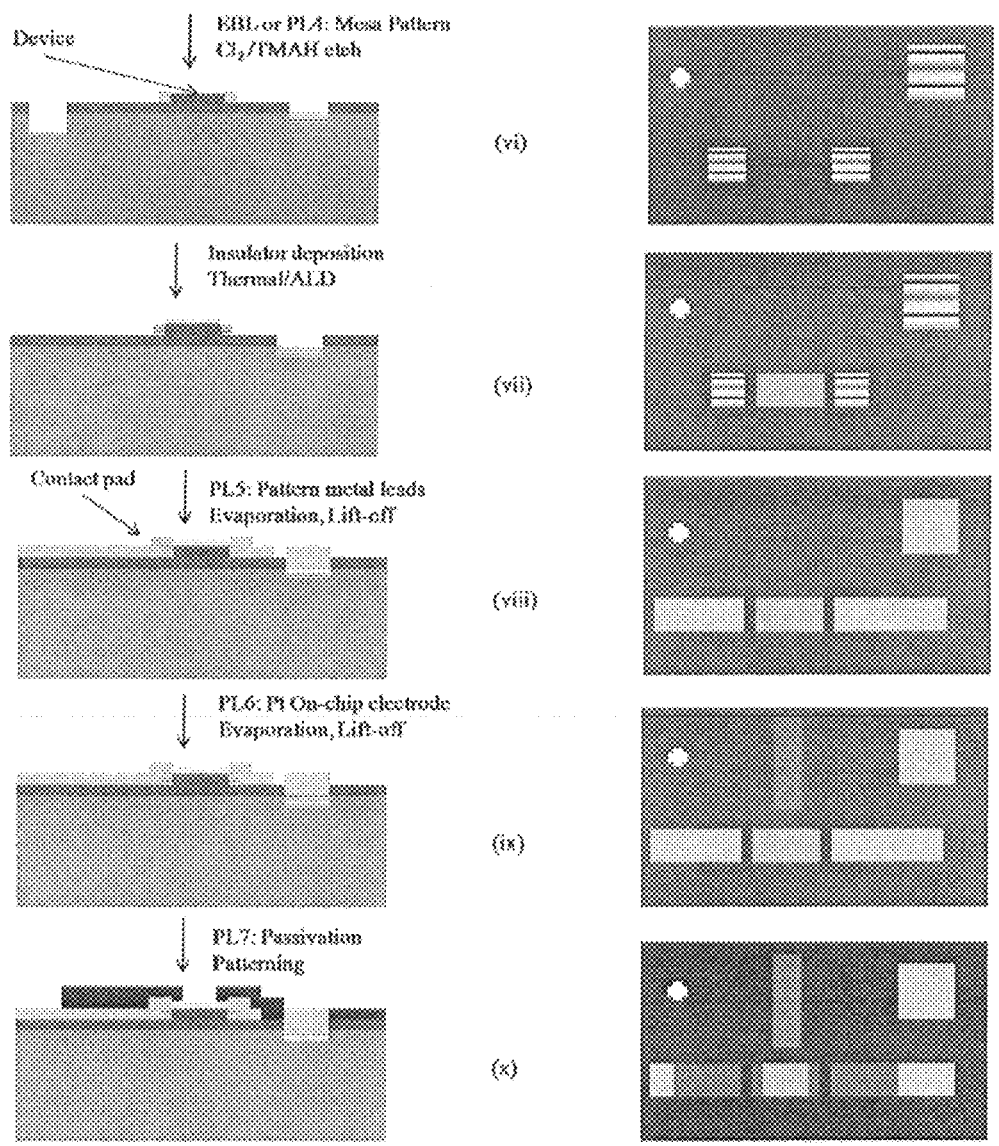

In the 1st PL step (FIG. 32(*iii*)) alignment marks were patterned and etched using SF$_6$/C$_4$F$_8$ chemistry. This allows both optical and electron-beam lithographic definition of mesas. Shipley 1827 photoresist was used as a masked. A 5-minute etch step yielded 2 μm deep alignment marks. This is sufficient enough to achieve good contrast in the electron beam writer (Vistec 5000+) and maintain the overall edge quality of both optical and e-beam alignment marks. The etch process was in-house designed to imitate the standard Bosch process for deep RIE etching of silicon—SF$_6$ is utilized for etching of silicon (300 nm/min) and silicon oxide (50 nm/min), while C$_4$F$_8$ serves for passivation layer formation by forming a polymer on the surface and thus preventing the sidewall etch (Abdolvand et al., 2008, Sens and Actuators A: Physical, 144: 109-116).

The second PL step (FIG. 32(*iv*)) includes backgate via etch using BOE, followed by the third PL step (FIG. 32(*v*)) to form implantation regions. In this process BF$_2^+$ at 8 keV was used as a dopant instead of boron (Sakurai et al., 2006, Fully-depleted SOI CMOS Circuits and Technology for Ultra-Low Power Applications, Springer). The heavier BF$_2^+$ has lower range and is used for shallow implantation. The dopant is then activated using rapid thermal annealing (RTA) at 1000° C. for 30 seconds instead of thermal activation to prevent redistribution.

The next step (FIG. 32(*vi*)) involves mesa definition by either photolithography (smallest feature 1 mm) or electron-beam lithography (smallest feature 10 nm). In case of electron beam lithography hydrogen silsesquioxane (HSQ) based photoresist was used (Henschel et al., 2003, J Vac Sci Technol B, 21: 2018-2025). When exposed to the electron beam HSQ converts into amorphous silicon dioxide-like structure and can be used as an etch mask. Its crystallinity is further improved by annealing in O$_2$ atmosphere at 700-800° C. (Holzwarth et al., 2007, J Vac Sci Technol B, 25: 2658-2661). The wafer is then briefly etched (5 seconds) in Oxford 100 RIE using CF$_4$ chemistry to remove the oxide layer formed during the annealing step. Mesas are then etched using 22% TMAH solution (v/v, H$_2$O in water) at 60° C. for 90 seconds (Tabata et al., 1992, Sens Actuators A: Physical, 34: 51-57).

Following the mesa definition step, an insulator deposition step is performed (FIG. 32(*vii*)). This step is crucial since it serves to prolong device life in electrolyte solution and improve overall electrical characteristics. The insulator formation can be performed in two ways: a) by thermal growth (dry oxide) b) atomic layer deposition (ALD).

In the fifth PL step (FIG. 32(*viii*)) contact vias are etched using 10:1 BOE followed by a metal deposition and lift-off. Total of 145 nm Al/5 nm Ti was evaporated. For the lift-off process, LOR5A/S1808 bilayer was used in N-methylpirilidone (NMP).

In the 6th PL step (FIG. 32(*ix*)) Pt was evaporated and similar lift-off process was performed to form on-chip reference electrode.

Finally in the seventh PL step (FIG. 32(*x*)), passivation layer is deposited and patterned. Two types of passivation layer are used—traditional photoresist and more chemically resistive SU-8 polymer. The latter one allows better compatibility with Polydimethylsiloxane (PDMS) based microfluidics.

Figure 33:
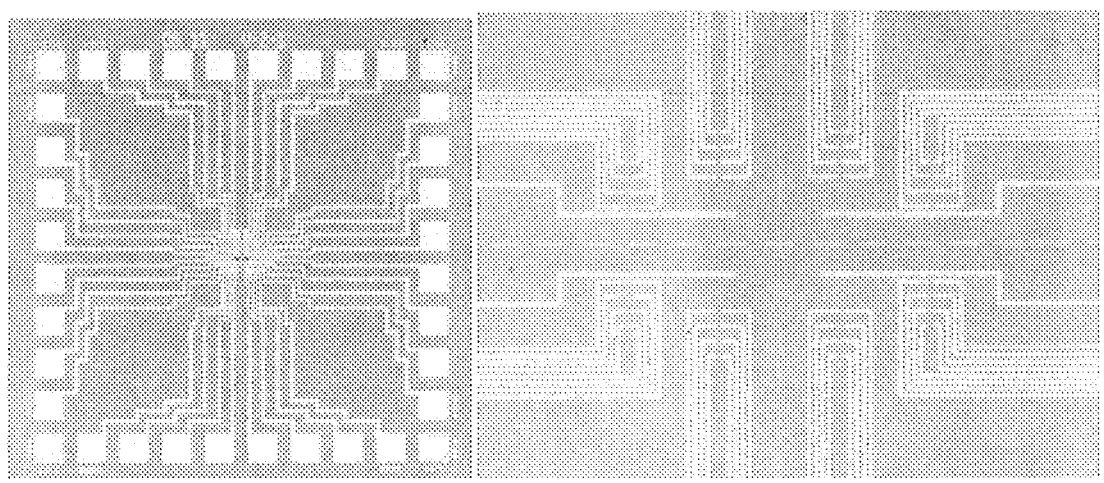
FIG. 33 depicts the geometry of exemplary sensors of the invention. The depicted geometry allows easy microfluidic integration and multiplexing.

The new layout is compatible with the Microcascade Autoprobe System which allows automated I-V screening (FIG. 33). In addition several Matlab programs were developed to allow automated data analysis to extract relevant electrical parameters.

Figure 34:
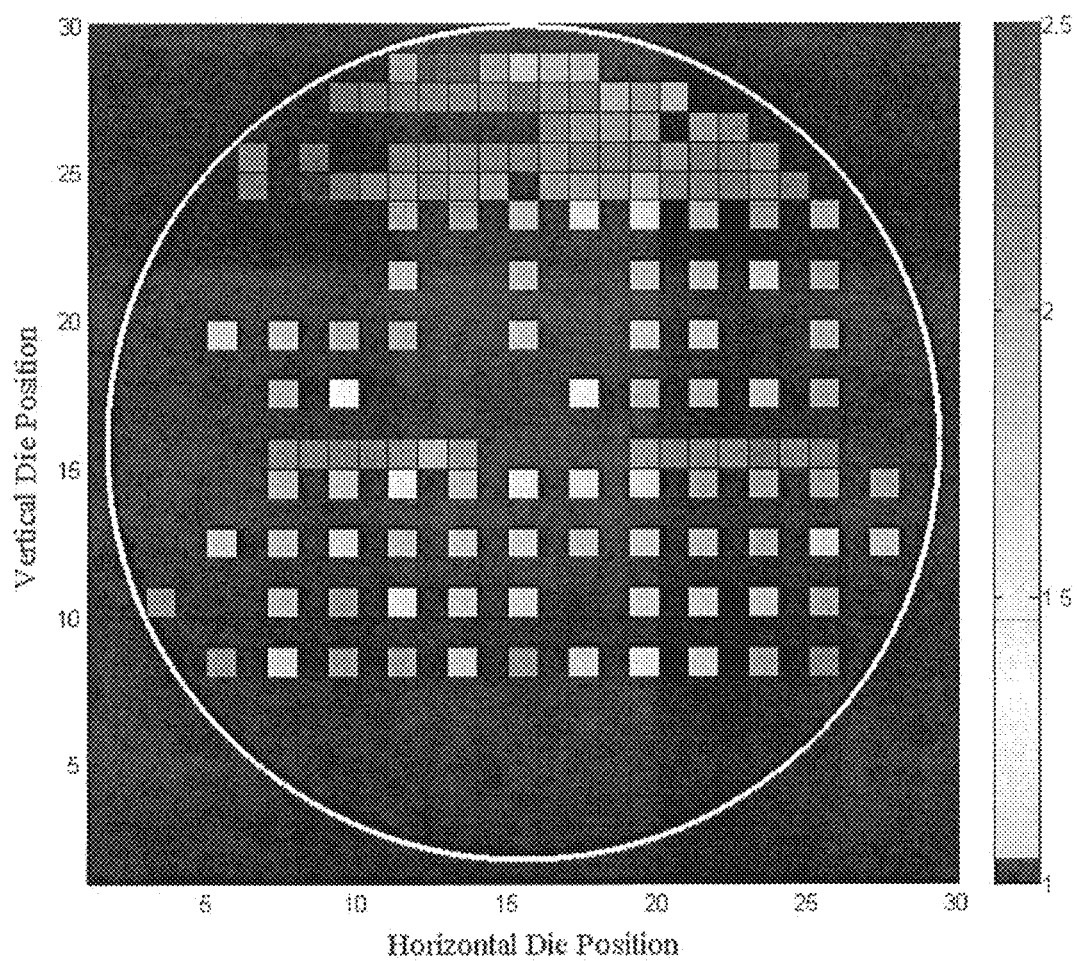
FIG. 34 is depicts an illustration demonstrating the threshold voltage distribution on a wafer scale for 144 dies. The threshold voltage for each die represents a mean value for, on average, 6 devices. Regions without color represent dies that were not measured.
Figure 35:
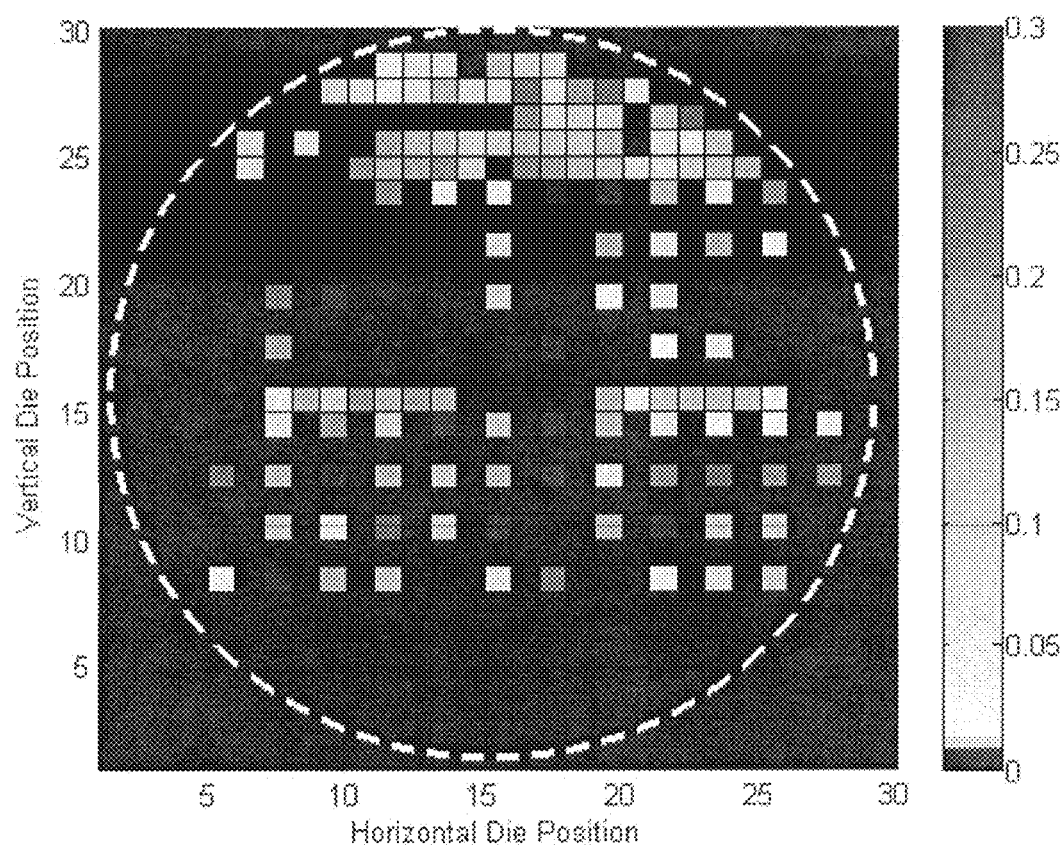
FIG. 35 depicts an illustration demonstrating the wafer scale distribution of threshold voltage standard deviation. Each die represents a set of up to 13 devices.
Figure 36:
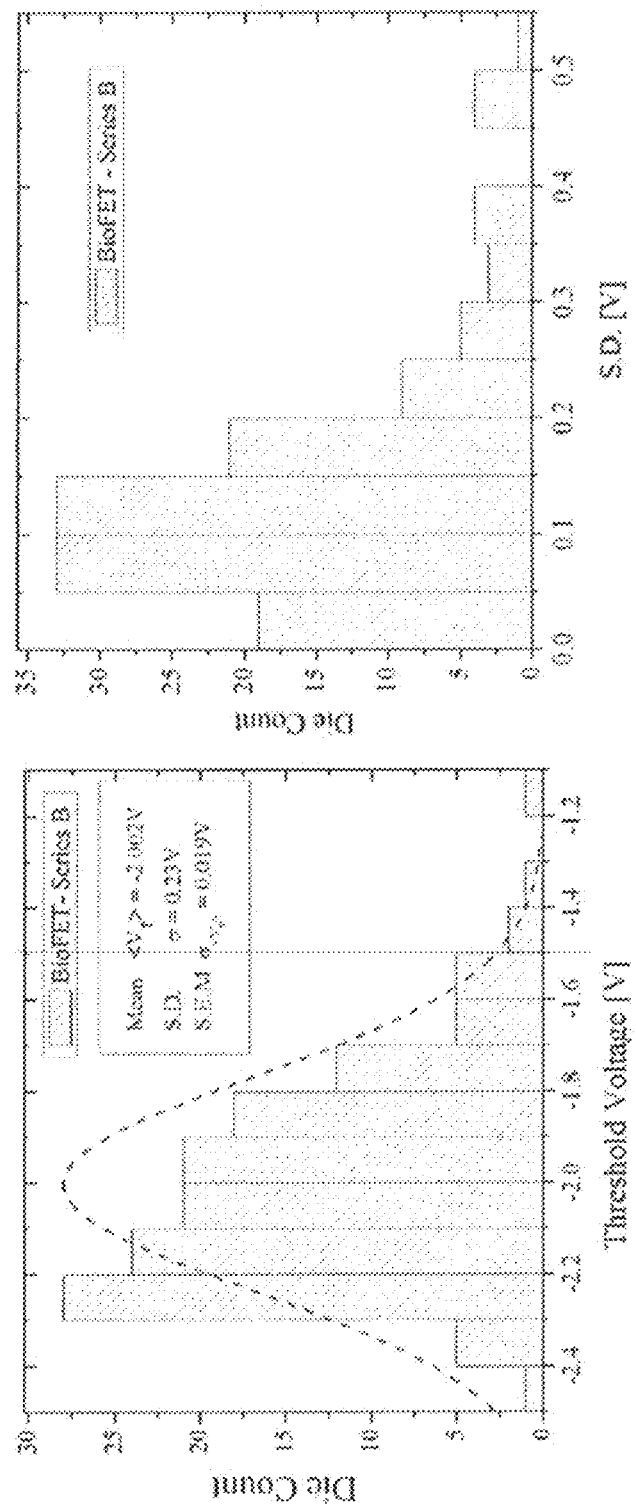
FIG. 36 depicts graphs showing the threshold voltage distribution and standard deviation of 144 dies with approximately 1100 bioFET devices.
Figure 37:
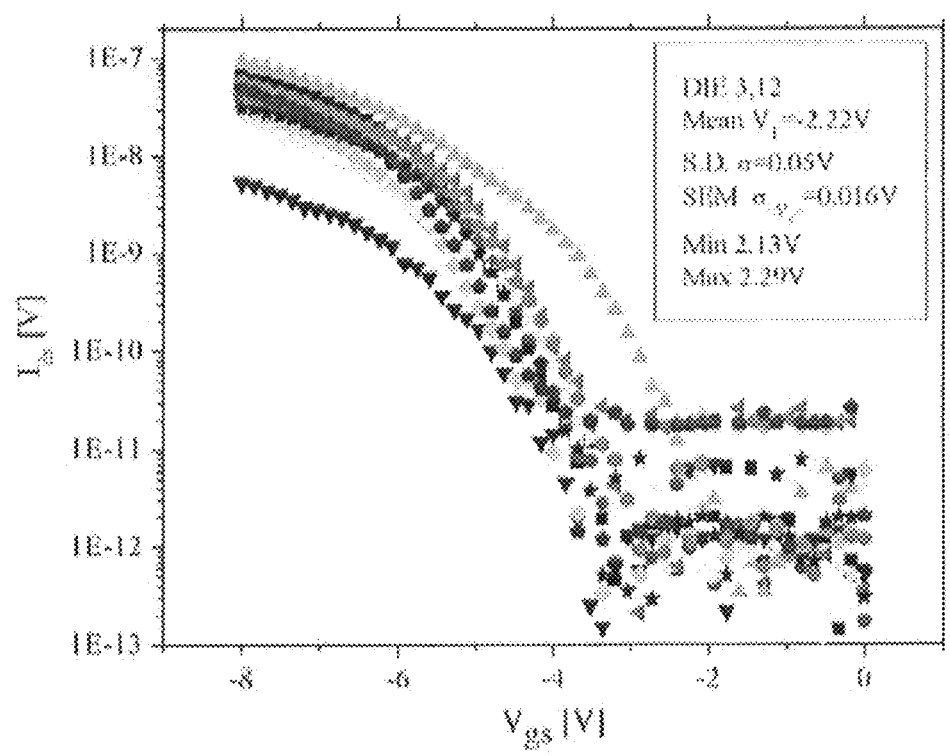
FIG. 37 is a graph depicting the $I_{DS}$-$V_{GS}$ characteristics of 8 devices on the same die.

To understand the distribution of threshold voltages on a larger scale, its' dependence as a function of die position was investigated, as illustrated in FIG. 34. For each die, color represents average threshold voltage of up to 13 devices. The variation in threshold voltages is due to the initial non-uniformity of the active silicon layer (70±10 nm) in addition to the wafer scale variation in dry oxidation process which contributes to addition 5% variation. There are total 144 dies measured, with a total of approximately 1100 devices. Similarly, FIG. 35 shows standard deviation of threshold voltage per each chip. As mentioned before each chip represents an average of up to 13 devices. FIG. 36 shows the distribution of the average die threshold voltage and its standard deviation. FIG. 37 shows I-V characteristics of 10 devices on the same 3.3 mm by 3.3 mm chip. The average voltage is calculated to be $<V_T>=-2.22$ V with the standard deviation of $\sigma=0.05$V and standard error of the mean $\sigma_{<VT>}=0.016$V.

Figure 38:
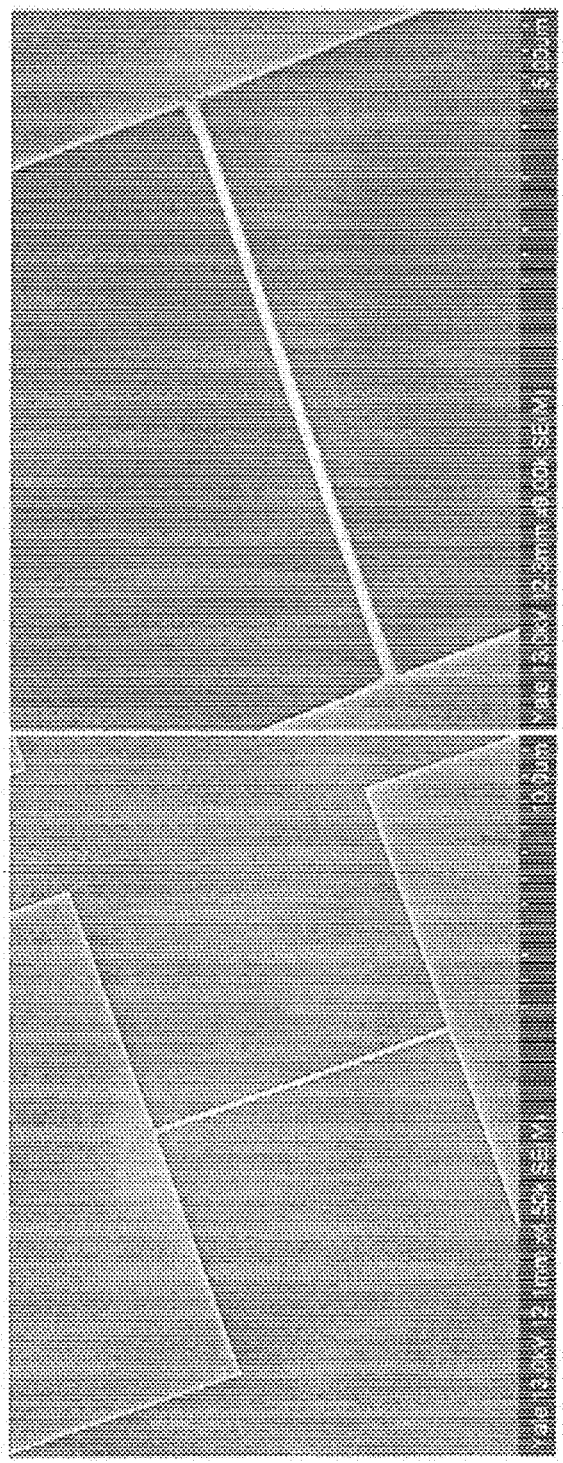
FIG. 38 depicts scanning electron micrographs of nanowire mesas obtained by TMAII etching using HSQ as an etch mask.

Series B fabrication process allows for electron beam lithography (EBL) defined devices. Instead of using optical photoresist (e.g. S1808) in PL4 step described in FIG. 32-*vi* one call use a hydrogen silsesquioxane (HSQ) to pattern the mesas. Using this method, devices were fabricated with widths ranging from 60 nm to 2000 nm on the same die. Sample scanning electron micrograph is shown in FIG. 38.

To explore the quality of fabricated devices it is necessary to record the $I_{DS}$–$V_{GS}$ characteristics, as shown in FIG. 39A. Typical leakage current is measured to be between 10-100 fA. More importantly this fabrication process demonstrated good control over device threshold voltages and subthreshold swings (FIG. 39B).

Example 5: Multiplexed SOI BioFETs

Nanoscale Field Effect Transistors have emerged as a promising technology for ultrasensitive, unlabeled diagnostic applications. However, their use as quantitative sensors has been problematic because of the need for individual sensor calibration. An internal calibration scheme for multiplexed nanoribbon field effect sensors by utilizing the initial current rates rather than end point detection is demonstrated herein. A linear response is observed consistent with initial binding kinetics. Moreover, it is shown that top-down fabrication techniques yield reproducible device results with minimal fluctuations, enabling internal calibration.

Multiplexed sensing of cancer antigens and calibration of Silicon-On-Insulator (SOI) nanoribbon BioFETs fabricated using traditional lithographic methods is demonstrated herein. The top-down method accounts for the uniformity of device electrical characteristics which gives sensing repeatability and reproducibility. This aspect enables multiplexing, which allows for simultaneous data acquisition with better statistical analysis. The nanosensor surface is modified with capture antibodies which allow specific recognition of target biomarkers. Instead of using end-point detection to quantify device response, initial rate was instead measured, which has been shown using surface plasmon resonance (SPR) for antigen-antibody interactions to be linearly dependent on the analyte concentration (Homola, 2003, Anal Bioanal Chem, 377: 528-539). Furthermore, it is shown that initial current rate scales linearly with both device baseline current and solution transconductance, supporting the claim of using device electrical parameters for sensor calibration and suppression of device-to-device variation. Using the disclosed method, universal calibration curve for device response were demonstrated, for a given biomarker. Further, a blind test measurement performed to demonstrate the validity of the internal calibration standard is presented.

The materials and methods employed in these experiments are now described.

Figure 40A:
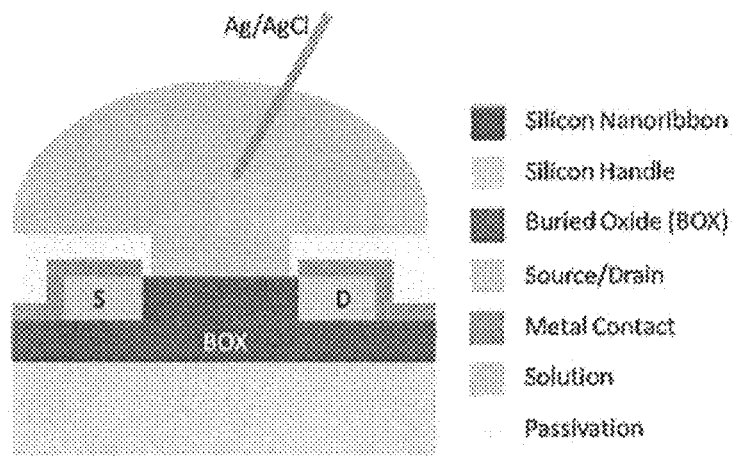
FIG. 40A through FIG. 40C, depicts the device schematic and plots which demonstrate the characteristics of exemplary devices.

Silicon nanoribbon devices are fabricated from Silicon-on-Insulator (SOI) wafers in a process similar to the one previously described (Stern et al., 2010, Nat Nanotechnol, 5: 138-142). Nanosensor mesas were defined by chlorine reactive ion etching of 4" (100) SOI wafers with 25-35 nm of active Si layer (resistivity 1-10 Ωcm) and 145 nm of buried oxide and silicon handle used as a backgate. Following the backgate etch and $BF_2^+$ implantation (Core Systems, Inc., dose $5\times10^{15}$ $cm^{-2}$, energy 8 keV, tilt 7°), devices were annealed using a Rapid Thermal Processor (RTP) at 1000° C. for 30 s for dopant activation. Metal contacts were formed by electron beam deposition of Ti/Al stack (5 nm/145 nm) and ohmic contacts were formed by an RTP annealing at 450° C. for 1 min with $N_2$ purge. Devices were protected using hard baked S1813 photoresist. A schematic of a device is shown in FIG. 40A. Dies (5 mm×5 mm) were packaged using 28-pin ceramic headers (Spectrum Semiconductor Materials, Inc., model CSB02892). Multiplexed I-V and DC time measurements were done using custom made system using a National Instruments Data Acquisition Card and Keithley 2636 Dual Source Measure Unit.

Prior to protection layer deposition, devices were functionalized with 3-aminopropyltriethoxy silane (APTES) functionalization by immersing in 5% (v/v) solution of APTES in toluene in an inert atmosphere for 2 h. The devices were then baked in a vacuum oven for 4 h at 180° C.

Antibody functionalization was performed after I-V screening. Prostate specific (PSA) and breast cancer antigens (CA15.3) were chosen for multiplexed detection and calibration. Receptors, anti-PSA and anti-CA15.3 were bound to the nanoribbon surface using N-hydroxysulfosuccinimide/1-ethyl-3-(3-dimethylaminopropyl)carbodiimide hydrochloride (NHS/EDC) chemistry in 1× phosphate buffer saline (PBS, Sigma) at pH 7.4 for 2 h (Selo et al., 1996, J Immunol Methods, 199: 127-138). Samples were then washed with 1×PBS and a blocking step was performed with 10% fetal bovine serum (FBS) for 30 min, followed by washing with sensing buffer (1 mM bicarbonate buffer at pH 9).

Sensing experiments were done in direct current (DC) regime with gate-source and drain-source voltages being $V_{gs}=-3$ V and $V_{ds}=0.2$ V, respectively, reference Ag/AgCl electrode grounded and a sampling time of $t_s=0.5$ s between DC current measurements. In each sensing experiment devices were first measured in 5 μl of buffer solution to confirm a stable baseline current, followed by the addition of 5 μl of analyte solution, upon which the current was observed and recorded.

The results of the experiments are now described.

Figure 40B:
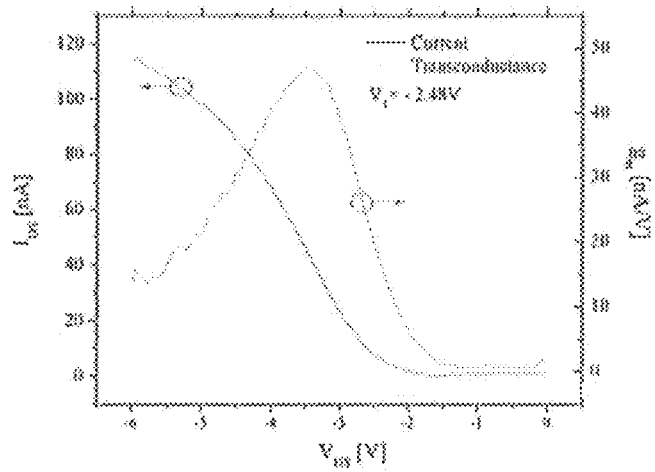
Figure 40C:
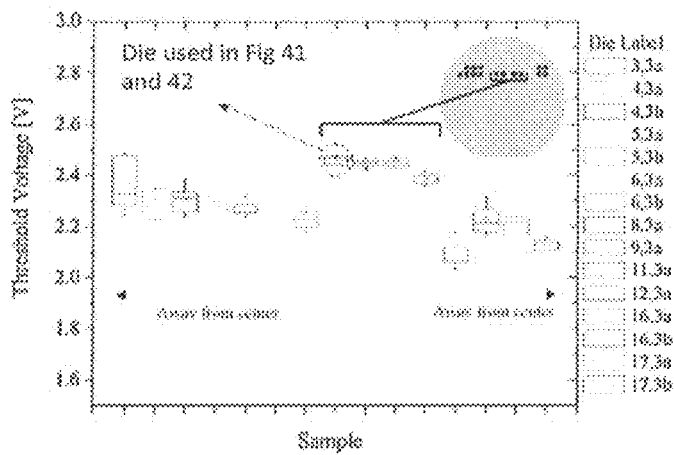

Device characteristics were assessed by simultaneous measurement of up to 8 devices on a given die. FIG. 40B shows the $I_{DS}$–$V_{GS}$ characteristics of a representative p-type accumulation mode device. Devices showed relatively narrow threshold voltage distribution, with average $V_T=-2.3$ V, standard deviation of 0.15 V and standard error of the mean of 0.014 V for sample of 106 devices. The distribution in threshold voltages was dominated by the non-uniform thickness of the active silicon layer (70±10(3σ) nm) and variations in the thickness of the thinning dry oxide (up to 5%). FIG. 40C shows the variation of threshold voltage for a series of dies, and the corresponding wafer map. Even with the variations of threshold voltage across the entire wafer, results with less than 10% error were demonstrated (see below). In regions with minimal thickness fluctuations (wafer center), threshold voltage variations of 8 mV, standard error of the mean, were obtained. The off current of dry devices was measured to be on the order 1-100 fA which yields good on/off current ratios of approximately 5-6 orders of magnitude. The average subthreshold swing was (630±60) mV/dec which is the consequence of 145 m thick buried oxide layer between the active silicon layer and the backgate. The average drift mobility obtained from peak transconductance was calculated to be (93±17) $cm^2/Vs$ which is in agreement with previously obtained values measured on fully depleted SOI RIE defined devices (Habicht et al., 2010, Solid-State Device Research Conference (ESSDERC), Sevilla, pp. 372-375).

Figure 41:
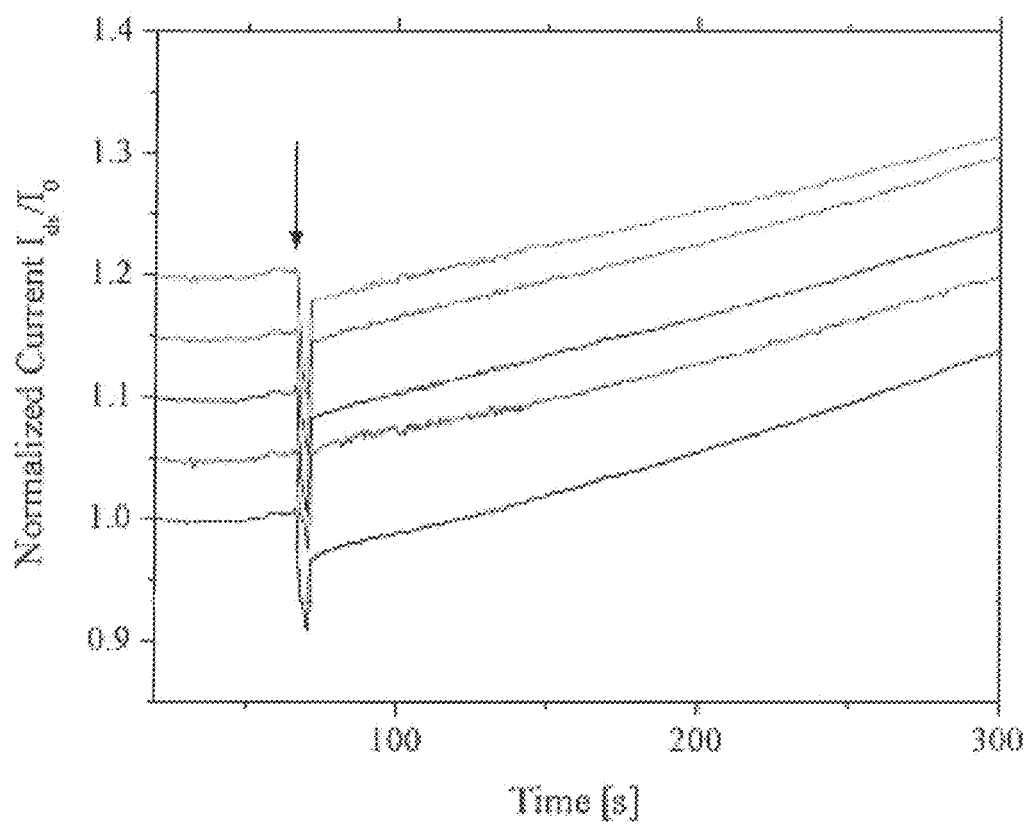
FIG. 41 depicts a plot demonstrating the normalized current response of 5 functionalized devices on the same chip upon the addition of CA15.3, measured simultaneously. $I_0$ is the baseline current for a given device prior to analyte addition. The arrow indicates injection of the analyte solution. Time traces are intentionally offset by 0.05 along they-axis for visual clarity.

Bonded chips integrated with a fluidic mixing chamber (Stern et al., 2007, Nature, 445: 519-522) were functionalized with CA15.3 and PSA specific antibodies (anti-CA15.3 and anti-PSA, respectively) using NHS/EDC chemistry. Prior to analyte addition (CA15.3 or PSA), 5 μl of sensing buffer was left in the mixing chamber and a baseline current $I_0$ was measured. This was followed by the addition of 5 μl of analyte solution upon which the current $I_{ds}$ was recorded as a function of time. Current rate was calculated numerically from recorded data after data acquisition. Next initial current rates were measured, which are directly proportional to the analyte concentration. FIG. 41 shows normalized simultaneous responses of 5 devices on the same chip upon the addition or 5 μl solution of 9.5 U/ml CA15.3. Device signals were normalized using their baseline currents established prior to analyte injection. FIG. 42 shows that initial current rates are, as expected, linearly proportional to device electrical parameters, i.e. baseline current, therefore confirming the validity of the method.

FET current and transconductance are given by $$i_{ds} = \begin{cases} k(v_g - v_T)v_{ds}, & \text{linear region} \\ \frac{k}{2}(v_g - v_T)^2, & \text{saturation region} \end{cases} \quad (7)$$

and $$g_m = \frac{\partial id}{\partial v_{gs}} = \begin{cases} kv_{ds}, & \text{lin. reg.} \\ k(v_{gs} - v_T), & \text{sat. reg.} \end{cases} \quad (8)$$

respectively, where v is the reference gate potential and $v_T$ is the device pre-sensing threshold voltage. The baseline current $I_{ds0}$ and transconductance $g_{m0}$ prior to analyte addition are linearly related by $$i_{ds0} = \alpha(v_g - v_T)g_{m0}, \quad (9)$$

where, $$\alpha = \begin{cases} 1, & \text{lin. reg.} \\ 1/2, & \text{sat. reg.} \end{cases} \quad (10)$$

which implies that normalizations by device baseline current $i_{ds0}$ and by transconductance go would yield the same results if the term $v_g - v_T$ does not change significantly between devices. In prior work (Ishikawa et al., 2009, ACS Nano, 3(12): 3969-3976) it was found that the scaling was better for transconductance normalization versus baseline current normalization. This is because, in this prior work, the initial current normalization is given by $$\Delta I/I_{ds} = \Delta v_T/(v_{gs} - v_T), \quad (11)$$

where ΔI is the current change caused by the equivalent gating potential Δv of the absorbed biomolecules, and $v_T$ is the threshold voltage of the device. Similarly, the transconductance scaling is given by $$\Delta I/(dI_{ds}/dV_g) = \Delta v_T. \quad (12)$$

In the approach presented here the variation of $v_T$ is insignificant (14 mV SEM with $|v_T|$=2.3 V, or <1%), and thus initial current rate or transconductance scaling gives equivalent results.

Figure 43A:
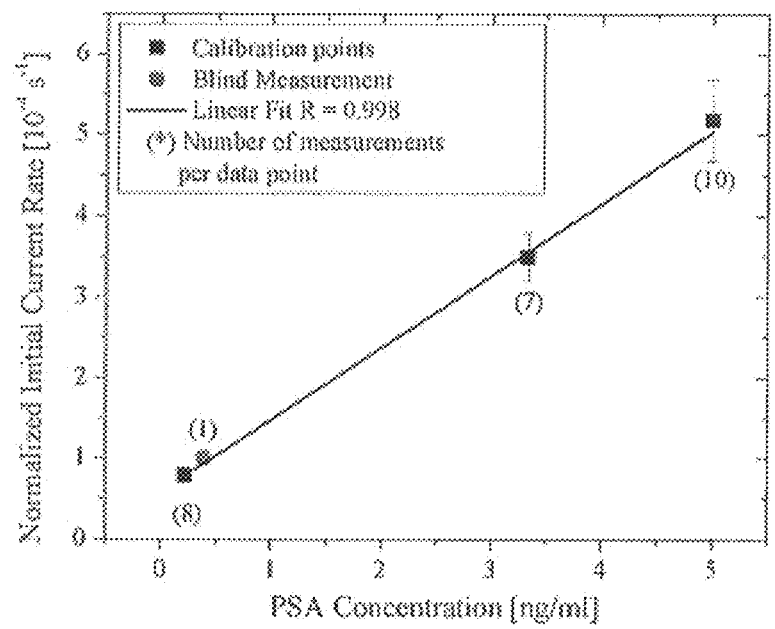
FIG. 43A and FIG. 43B, depicts calibration curves generated by the methods of the invention.
Figure 43B:
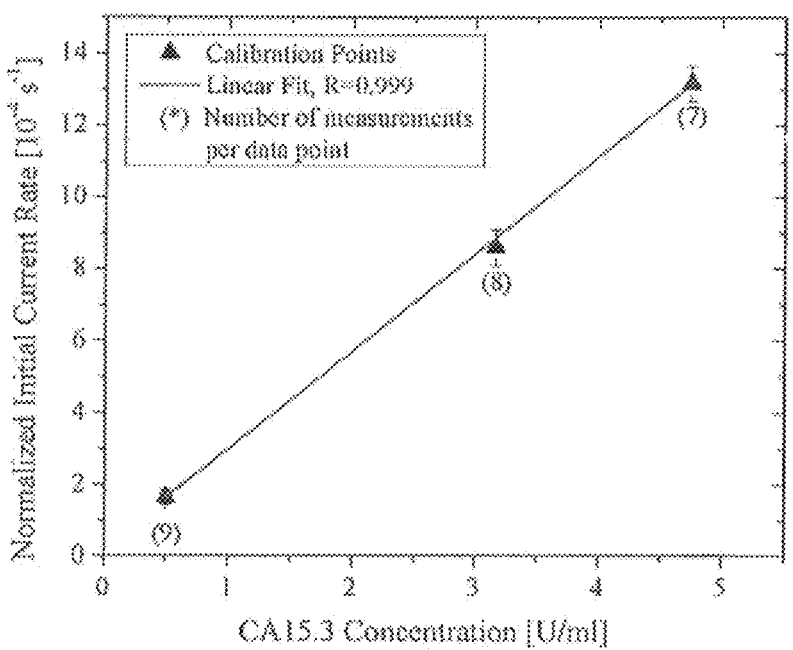

Measurements were repeated multiple times on different dies using different dilutions of the 9.5 U/ml stock solution. A similar procedure was repeated for PSA detection using the serial dilutions of 10 ng/ml. Applying the described normalizing method for the three analyte concentrations one can plot calibrations curves, as shown in FIG. 43A and FIG. 43B, for PSA and CA15.3, respectively. The device response was linear in the clinically relevant concentration range (1-10 ng/ml for PSA, 1-10 U/in for CA15.3) (Vizearra et al., 1996, Breast Cancer Res Treat, 3(37): 209-216; Wu et al., 2001, Nat Biotechnol, 19: 856-860). Even though the absolute errors of the stock solution concentrations, as determined by ELISA, were relatively large (15-20% for PSA and 40% for CA15.3), the variation of device responses was less than 10% (in terms of the standard error of the mean, SEM). Each data point represents an average over multiple (7-10) devices. Both fits had correlation coefficients R>0.98. Table 1 summarizes the calibration results obtained for PSA and CA15.3 and demonstrates the relative standard error of the mean to be less than 10%.

TABLE 1

Calibration points for PSA and CA15.3 obtained on multiple devices demonstrating the relative standard error of the mean to be below 10%.

| | Number of devices | Normalized device signal, average ($s^{-1}$) | Standard error of the mean ($s^{-1}$) | % Error |
|---|---|---|---|---|
| PSA concentration (ng/ml) | | | | |
| 3.3 ± 0.7 | 7 | $3.225 \times 10^{-4}$ | $2.9 \times 10^{-5}$ | 8.8 |
| 5.0 ± 1.0 | 10 | $5.179 \times 10^{-4}$ | $5.1 \times 10^{-5}$ | 9.9 |
| 0.22 ± 0.04 | 8 | $7.869 \times 10^{-5}$ | $7.5 \times 10^{-6}$ | 9.6 |
| CA 15.3 concentration (U/ml) | | | | |
| 4.75 ± 1.8 | 7 | $1.32 \times 10^{-3}$ | $5 \times 10^{-5}$ | 3.8 |
| 3.2 ± 1.2 | 8 | $8.6 \times 10^{-4}$ | $5 \times 10^{-5}$ | 5.8 |
| 0.5 ± 0.2 | 9 | $1.65 \times 10^{-4}$ | $1 \times 10^{-5}$ | 6 |

In addition, the calibration method was tested using a blind measurement on a single device and a different measurement setup (circle, FIG. 43A), which was compared to the calibrated data. Upon introducing a concentration of (0.4±0.08) ng/ml of PSA (determined by conventional ELISA) a normalized current rate of $1.0054 \times 10^{-4}$ $s^{-1}$ was measured. Using the calibration curve shown in FIG. 43A the expected value to be (0.46±0.06) ng/ml was calculated. This measurement deviated from the concentration obtained using conventional ELISA by approximately 15%.

Here a novel method for internal calibration of nanoscale FETs is demonstrated. This method was used for quantification of clinically relevant analytes, i.e. cancer biomarkers PSA and CA15.3. This approach is enabled by the ability of the CMOS-compatible fabrication approach developed to produce devices with very similar transport characteristics. Initial kinetic rates were used, which are directly proportional to the analyte concentrations (assuming an initial unused sensor) rather than the endpoint detection. Measured calibration curves showed a linear response in the relevant concentration ranges as well as good agreement with a blind measurement. In addition, it is demonstrated that calibration by baseline current normalization was equivalent to that obtained by transconductance normalization. Results presented herein demonstrate that nanosensors fabricated by conventional CMOS compatible processes yield reproducible results traceable to a calibration standard. It is believed that this approach will make nanoscale FET sensor technology a step closer to commercial point-of-care applications.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A system for quantitative detection of an analyte in a sample, the system comprising a solution chamber, a sensor, and a signal processor,
wherein the solution chamber is fluidically connected to the sensor, and the sensor is connected to the signal processor,
the sensor comprising one or more nanostructures etched on a substrate and having uniform electrical characteristics,
the signal processor comprising integrated signal processing electronics, wherein
the signal processor internally calibrates the sensor based on the electrical characteristic of each one of the one or more nanostructures when the sample is applied to the sensor to provide a normalized device response for the quantitative detection of the analyte;
wherein the sensor is calibrated by
obtaining at least one characteristic of the sensor;
applying a test sample to the sensor;
measuring an initial response rate by the one or more nanostructures of the sensor in response to the application of the test sample; and
normalizing the measured initial response rate by the obtained characteristic.

2. The system of claim 1, wherein the initial response rate is an initial current rate.

3. The system of claim 2, wherein each of the one or more nanostructures forms an electrically conducting pathway between at least a first contact and a second contact, wherein at least one of the baseline current, transconductance, and threshold voltage are uniform.

4. The system of claim 3, wherein the substrate is selected from the group consisting of a semiconductor substrate and a semiconductor-on-insulator (SOI) substrate.

5. The system of claim 3, wherein each of the one or more nanostructures is selected from the group consisting of a nanowire and a nanoribbon.

6. The system of claim 3, wherein the first and second contacts form a source and a drain contact, respectively.

7. The system of claim 3, wherein a gate contact is applied to the sensor.

8. The system of claim 5, wherein the gate contact is a solution gate.

9. The system of claim 3, wherein the solution chamber is coupled to the sensor for mixing a plurality of fluids and supplying the mixed fluids to the sensor for liquid-phase electrical response characterization.

10. The system of claim 3, wherein the sensor detects the presence of a specific analyte and wherein the surface of the nanostructure is functionalized with receptor molecules that bind to the specific analyte.

11. The system of claim 3, wherein the current conducted by each of the one or more nanostructures is altered by the presence of a parameter to be sensed.

12. The system of claim 3, wherein the initial current rate of the current conducted by each of the one or more nanostructures is indicative of the presence of a parameter to be sensed.

13. The system of claim 12, wherein the response of the sensor is calibrated by normalizing the initial current rate by the characteristic of the sensor.

14. The system of claim 13, wherein the characteristic of the sensor is at least one selected from the group consisting of baseline current, voltage, and transconductance.

15. The system of claim 14, wherein transconductance is solution transconductance.

16. The system of claim 13, wherein calibration allows quantification of a parameter to be sensed.

17. The system of claim 1, wherein the system generates a calibration curve for the analyte to be detected by:
obtaining at least one characteristic of the sensor;
applying a first sample comprising a first known concentration of the analyte to the sensor;
measuring the initial response rate conducted by the one or more nanostructures of the sensor in response to the application of the first sample;
normalizing the measured initial response rate by the obtained characteristic, thereby providing a first known normalized device signal;
applying a second sample comprising a second known concentration of the analyte to the sensor;
measuring the initial response rate conducted by the one or more nanostructures of the sensor in response to the application of the second sample;
normalizing the measured initial response rate by the obtained characteristic, thereby providing a second known normalized device signal;
plotting a first known data point, wherein the first known data point comprises the first known concentration of the analyte and the corresponding first known normalized device signal, and a second known data point, wherein the second known data point comprises the second known concentration of the analyte and the corresponding second known normalized device signal, on a graph; and fitting a calibration curve between the first known data point and the second known data point.

18. The system of claim 1, wherein the system quantitatively detects the concentration of the analyte in the test sample by obtaining a measured normalized device signal when normalizing the measured initial response rate by the obtained characteristic; and
calculating the concentration of the analyte using the measured normalized device signal and a calibration curve specific for the analyte.

19. The system of claim 1, wherein the system comprises signal processing, error detection, complementary detection, or a combination thereof.

20. The system of claim 1, wherein the sensor is a multiplexed sensor comprising a plurality of nano structures.

21. The system of claim 20, wherein the multiplexed sensor provides simultaneous detection of the analyte from the plurality of the nanostructures.

22. The system of claim 1, wherein the calibration of the sensor provides a normalized device signal for each of the one or more nanostructures of the sensor.

23. The system of claim 22, wherein the normalized device signals for the nanostructures vary by less than 20%.

* * * * *